United States Patent
Ferrone et al.

(10) Patent No.: US 11,091,547 B2
(45) Date of Patent: Aug. 17, 2021

(54) ANTI-CHONDROITIN SULFATE PROTEOGLYCAN 4 ANTIBODIES AND USES THEREOF

(71) Applicants: Memorial Sloan Kettering Cancer Center, New York, NY (US); The General Hospital Corporation, Boston, MA (US)

(72) Inventors: Soldano Ferrone, Boston, MA (US); Nai-Kong V. Cheung, New York, NY (US); Ming Cheng, Ridgefield, CT (US)

(73) Assignees: Memorial Sloan Kettering Cancer Center, New York, NY (US); The General Hospital Corporation, Boston, MA (US)

( * ) Notice: Subject to any disclaimer, the term of this patent is extended or adjusted under 35 U.S.C. 154(b) by 764 days.

(21) Appl. No.: 15/526,309

(22) PCT Filed: Nov. 12, 2015

(86) PCT No.: PCT/US2015/060465
§ 371 (c)(1),
(2) Date: Nov. 20, 2017

(87) PCT Pub. No.: WO2016/077638
PCT Pub. Date: May 19, 2016

(65) Prior Publication Data
US 2017/0342151 A1  Nov. 30, 2017

Related U.S. Application Data

(60) Provisional application No. 62/078,849, filed on Nov. 12, 2014.

(51) Int. Cl.
*C07K 16/00* (2006.01)
*C07H 21/04* (2006.01)
*C12N 5/12* (2006.01)
*C07K 16/28* (2006.01)
*C07K 16/30* (2006.01)
*C07K 16/44* (2006.01)
*A61K 39/00* (2006.01)

(52) U.S. Cl.
CPC ...... *C07K 16/2809* (2013.01); *C07K 16/3053* (2013.01); *C07K 16/44* (2013.01); *A61K 2039/505* (2013.01); *C07K 2317/24* (2013.01); *C07K 2317/31* (2013.01); *C07K 2317/34* (2013.01); *C07K 2317/622* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 5,869,045 | A * | 2/1999 | Hellstrom | A61K 47/6851 424/130.1 |
| 2013/0183288 | A1 | 7/2013 | Reff et al. | |
| 2013/0216528 | A1* | 8/2013 | Cheung | C07K 16/46 424/133.1 |
| 2013/0259865 | A1 | 10/2013 | Wang et al. | |
| 2013/0259873 | A1 | 10/2013 | Ferrone et al. | |
| 2014/0004124 | A1 | 1/2014 | Ferrone et al. | |
| 2014/0242079 | A1 | 8/2014 | Bacac et al. | |
| 2015/0119555 | A1* | 4/2015 | Jung | C07K 16/2803 530/387.3 |

FOREIGN PATENT DOCUMENTS

| | | |
|---|---|---|
| JP | 2012-503203 A | 2/2012 |
| JP | 2013-505732 A | 2/2013 |
| WO | WO-2010/033866 A2 | 3/2010 |
| WO | WO-2011/009090 A1 | 1/2011 |
| WO | WO-2011/039126 A1 | 4/2011 |
| WO | WO-2013/092001 A1 | 6/2013 |
| WO | WO-2013/102123 A2 | 7/2013 |
| WO | WO-2013/173820 A2 | 11/2013 |
| WO | WO-2014/131712 A1 | 9/2014 |
| WO | WO-2014/138306 A1 | 9/2014 |
| WO | WO-2014/165644 A2 | 10/2014 |

OTHER PUBLICATIONS

Asano, R. and Kumagai, I., Development of highly functional bispecific antibodies using protein engineering], Seikagaku Journal of Japanese Biochemical Society, 86(4)469-473 (2014). [Includes Machine Translation from Japanese to English].

Brown, M. et al, Tolerance to Single, but Not Multiple, Amino Acid Replacements in Antibody $V_H$ CDR2: A Means of Minimizing B Cell Wastage from Somatic Hypermutation?, The Journal of Immunology, 156(9): 3285-3291 (1996).

Andrade, D., et al, Engraftment of peripheral blood mononuclear cells from systemic lupus erythematosus and anti-phospholipid syndrome patient donors into BALB-RAG-2-/-IL-2Rgamma-/- mice: a promising model for studying human disease, Arthritis Rheum., 63(9):2764-2673 (2011).

Barritt, D.S., et al, The multi-PDZ domain protein MUPP1 is a cytoplasmic ligand for the membrane-spanning proteoglycan NG2, J. Cell Biochem., 79:213-224 (2000).

Bluemel, C., et al, Epitope distance to the target cell membrane and antigen size determine the potency of T cell-mediated lysis by BiTE antibodies specific for a large melanoma surface antigen, Cancer Immunol. Immunother., 59:1197-1209 (2010).

(Continued)

*Primary Examiner* — Mark Halvorson
(74) *Attorney, Agent, or Firm* — Choate, Hall & Stewart LLP; Brenda Herschbach Jarrell; Tracy L. Vrablik

(57) ABSTRACT

Described herein are antibodies that bind chondroitin sulfate proteoglycan 4 (CSPG4) and, in particular, chimeric and humanized anti-CSPG4 antibodies and fragments thereof. Also provided herein are methods of using individual humanized antibodies or compositions thereof for the detection, prevention, and/or therapeutic treatment of CSPG4-related diseases, in particular, melanoma.

20 Claims, 13 Drawing Sheets

Specification includes a Sequence Listing.

(56) References Cited

OTHER PUBLICATIONS

Bradbury, E.J., et al, Chondroitinase ABC promotes functional recovery after spinal cord injury, Nature, 416:636-640 (2002).
Bruland, O.S., et al, Hematogenous micrometastases in osteosarcoma patients, Clin. Cancer Res., 11(13):4666-4673 (2005).
Burns, W.R., et al, A high molecular weight melanoma associated antigen-specific chimeric antigen receptor redirects lymphocytes to target human melanomas, Cancer Res., 70(8):3027-3033 (2010).
Campoli, M., et al, Functional and clinical relevance of chondroitin sulfate proteoglycan 4, Adv. Cancer. Res., 109:73-121 (2010).
Campoli, M.R., et al, Human high molecular weight-melanoma-associated antigen (HMW-MAA): a melanoma cell surface chondroitin sulfate proteoglycan (MSCP) with biological and clinical significance, Crit. Rev. Immunol., 24(4):267-296 (2004).
Chang, C.C., et al, Immunotherapy of melanoma targeting human high molecular weight melanoma-associated antigen: potential role of nonimmunological mechanisms, Ann. N. Y. Acad. Sci., 1028:340-350 (2004).
Chatterjee, N., et al, Interaction of syntenin-1 and the NG2 proteoglycan in migratory oligodendrocyte precursor cells, J. Biol. Chem., 283(13):8310-8317 (2008).
Cheng, M., et al., Structural design of disialoganglioside GD2 and CD3-bispecific antibodies to redirect T cells for tumor therapy, Int. J. Cancer, 136(2): 476-86 (2014).
Cheung, N.K., et al, Ganglioside GD2 specific monoclonal antibody 3F8: a phase I study in patients with neuroblastoma and malignant melanoma, J. Clin. Oncol., 5(9):1430-1440 (1987).
Cheung, N.K., et al, Humanizing murine IgG3 anti-GD2 antibody m3F8 substantially improves antibody-dependent cell-mediated cytotoxicity while retaining targeting in vivo, OncoImmunol., 1(4):477-486 (2012).
Coloma et al., Design and production of novel tetravalent bispecific antibodies, Nat. Biotechnol., 15:159-63 (1997).
Del Vecchio, S., et al, Local distribution and concentration of intravenously injected 131I-9.2.27 monoclonal antibody in human malignant melanoma, Cancer Res., 49:2783-2789 (1989).
Eisenmann, K.M., et al, Melanoma chondroitin sulphate proteoglycan regulates cell spreading through Cdc42, Ack-1 and p130cas, Nat. Cell Biol., 1:507-513 (1999).
Geiser, M., et al., Identification of the human melanoma-associated chondroitin sulfate proteoglycan antigen epitope recognized by the antitumor monoclonal antibody 763.74 from a peptide phage library, Cancer Res., 59:905-910 (1999).
Geldres, C., et al, T lymphocytes redirected against the chondroitin sulfate proteoglycan-4 control the growth of multiple solid tumors both in vitro and in vivo, Clin. Cancer Res., 20(4):962-971 (2014).
Godal, A.,et al, Immunotoxins directed against the high molecular-weight melanoma-associated antigen. Identification of potent antibody-toxin combinations, Int. J. Cancer, 52:631-635 (1992).
Houghton, A.N. et al, Mouse monoclonal IgG3 antibody detecting GD3 ganglioside: a phase I trial in patients with malignant melanoma, Proc. Natl. Acad. Sci. U.S.A., 82:1242-1246 (1985).
Hwang, K.M., et al., Radiolocalization of xenografted human malignant melanoma by a monoclonal antibody (9.2.27) to a melanoma-associated antigen in nude mice, Cancer Res., 45:4150-4155 (1985).
Idusogie, E. E., et al, Mapping of the C1q Binding State on Rituxan, a Chimeric Antibody with a Human IgG1 Fc, The Journal of Immunology, 164: 4178-4184 (2000).
Iida, J., et al, Melanoma chondroitin sulfate proteoglycan regulates matrix metalloproteinase-dependent human melanoma invasion into type I collagen, J. Biol. Chem., 276(22):18786-18794 (2001).
International Search Report for PCT/US2015/060465, 5 pages (dated Feb. 23, 2016).
Jefferis, R., Glycosylation as a strategy to improve antibody-based therapeutics, Nat. Rev. Drug Discov., 8:226-234 (2009).
Kantor, R.R. et al, Analysis of the NIH workshop monoclonal antibodies to human melanoma antigens, Hybridoma, 1(4):473-82 (1982).
Kirsch, M., et al, Metastasis and angiogenesis, Cancer Treat. Res., Chapter 17, 285-304 (2004).
Klinger, M. et al, Immunopharmacologic response of patients with B-lineage acute lymphoblastic leukemia to continuous infusion of T cell-engaging CD19/CD3-bispecific BiTE antibody blinatumomab, Blood, 119(26): 6226-33 (2012).
Koo, G.C., et al, Use of humanized severe combined immunodeficient mice for human vaccine development, Expert Rev. Vaccines, 8(1):113-120 (2009).
Kusama, M., et al, Characterization of syngeneic anti-idiotypic monoclonal antibodies to murine anti-human high molecular weight melanoma-associated antigen monoclonal antibodies, J. Immunol., 143(11):3844-3852 (1989).
Law, C.L., et al, Expression and characterization of recombinant soluble human CD3 molecules: presentation of antigenic epitopes defined on the native TCR-CD3 complex, Int. Immunol., 14(4):389-400 (2002).
Luo, W., et al, Differential immunogenicity of two peptides isolated by high molecular weight-melanoma-associated antigen-specific monoclonal antibodies with different affinities, J. Immunol., 174:7104-7110 (2005).
Mayayo, S.L., et al, Chondroitin sulfate proteoglycan-4: a biomarker and a potential immunotherapeutic target for canine malignant melanoma, Vet. J., 190:e26-30 (2011).
Meier, F., et al., The adhesion molecule L1 (CD171) promotes melanoma progression, Int. J. Cancer, 119:549-555 (2006).
Mittelman, A, et al, Kinetics of the immune response and regression of metastatic lesions following development of humoral anti-high molecular weight-melanoma associated antigen immunity in three patients with advanced malignant melanoma immunized with mouse anti-idiotypic monoclonal antibody MK2-23, Cancer Res., 54:415-421 (1994).
Mittelman, A., et al, Human high molecular weight melanoma associated antigen mimicry by mouse anti-idiotypic monoclonal antibody MK2-23: modulation of the immunogenicity in patients with malignant melanoma, Clin. Cancer Res., 1:705-713 (1995).
Mittelman, A., et al, Human high molecular weight melanoma-associated antigen (HMW-MAA) mimicry by mouse anti-idiotypic monoclonal antibody MK2-23: Induction of humoral anti-HMW-MAA immunity and prolongation of survival in patients with stage IV melanoma, Proc. Natl. Acad. Sci. U.S.A., 89:466-470 (1992).
Mittelman, A., et al, Identification of monoclonal anti-HMW-MAA antibody linear peptide epitope by proteomic database mining, J. Invest. Dermatol., 123:670-675 (2004).
Natali, P.G., et al, Analysis of the antigenic profile of uveal melanoma lesions with anti-cutaneous melanoma-associated antigen and anti-HLA monoclonal antibodies, Cancer Res., 49:1269-1274 (1989).
Novak-Hofer, I., The L1 cell adhesion molecule as a target for radioimmunotherapy, Cancer Biother. Radiopharm., 22(2):175-184 (2007).
Oldham, R.K., et al, Monoclonal antibody therapy of malignant melanoma: in vivo localization in cutaneous metastases after intravenous administration, J. Clin. Oncol., 2(11):1235-1244 (1984).
Orcutt, K.D. et al., A modular IgG-scFv bispecific antibody topology, Protein Eng. Des. Sel., 23(4):221-8 (2010).
Raja, C., et al, Interim analysis of toxicity and response in phase 1 trial of systemic targeted alpha therapy for metastatic melanoma, Cancer Biol. Ther., 6:846-852 (2007).
Reichert, J. M., Marketed therapeutic antibodies compendium, mAbs, 4(3): 413-415 (2012).
Reinhold, U., et al, Specific lysis of melanoma cells by receptor grafted T cells is enhanced by anti-idiotypic monoclonal antibodies directed to scFv domain of the receptor, J. of Invest. Dermatol., 112:744-750 (1999).
Riccardo, F., et al, CSPG4-Specific Immunity and Survival Prolongation in Dogs with Oral Malignant Melanoma Immunized with Human CSPG4 DNA, Clin. Cancer Res., 20:3753-3762 (2014).
Rivera, Z., et al, CSPG4 as a target of antibody-based immunotherapy for malignant mesothelioma, Clin. Cancer Res., 18(19):5352-5363 (2012).

(56) References Cited

OTHER PUBLICATIONS

Scott, A. M., et al, Antibody therapy of cancer, Nature, 12: 278-287 (2012).

Stallcup, W.B. and Huang, F.J., A role for the NG2 proteoglycan in glioma progression, Cell Adh. Migr., 2:192-201 (2008).

Stegmuller, J., et al, AN2, the mouse homologue of NG2, is a surface antigen on glial precursor cells implicated in control of cell migration, J. Neurocytol., 31:497-505 (2002).

Torisu-Itakura, H., et al, Redirected lysis of human melanoma cells by a MCSP/CD3-bispecific BiTE antibody that engages patient-derived T cells, J. Immunother., 34(8):597-605 (2011).

Wagner, S., et al, Vaccination with a human high molecular weight melanoma-associated antigen mimotope induces a humoral response inhibiting melanoma cell growth in vitro, J. Immunol., 174:976-982 (2005).

Wang, X., et al, CSPG4 in cancer: multiple roles, Curr. Mol. Med., 10:419-429 (2010).

Wang, X., et al, CSPG4 protein as a new target for the antibody-based immunotherapy of triple-negative breast cancer, J. Natl. Cancer Inst., 102(19):1496-1512 (2010).

Wang, X., et al, Functional characterization of an scFv-Fc antibody that immunotherapeutically targets the common cancer cell surface proteoglycan CSPG4, Cancer Res., 71(24):7410-7422 (2011).

Weinstein, J.N. and Van Osdol, W., Early intervention in cancer using monoclonal antibodies and other biological ligands: micropharmacology and the "binding site barrier", Cancer Res., 52:2747s-2751s (1992).

Written Opinion for PCT/US2015/060465, 16 pages (dated Feb. 23, 2016).

Yang J., et al, Melanoma chondroitin sulfate proteoglycan enhances FAK and ERK activation by distinct mechanisms, J. Cell Biol., 165:881-891 (2004).

Dondelinger, M. et al., Understanding the Significance and Implications of Antibody Numbering and Antigen-Binding Surface/Residue Definition, Frontiers in Immunology, 9(16):1-15 (2018).

\* cited by examiner

TARGETING OF $^{124}$I-LABELLED HUMANIZED 763 ANITIBODIES TO SKMEL-28 XENOGRAFTS

| | % ID/gm | | | | | | | | TUMOR TO NON-TUMOR RATIO | | | | | | | |
|---|---|---|---|---|---|---|---|---|---|---|---|---|---|---|---|---|
| | MOUSE h763 | | hu763-IgG1 | | hu763-IgG4 | | hu763-IgG1n | | MOUSE h763 | | hu763-IgG1 | | hu763-IgG4 | | hu763-IgG1n | |
| N | 4 | | 6 | | 8 | | 6 | | 4 | | 6 | | 8 | | 6 | |
| ORGAN | MEAN | SEM | MEAN | SEM | MEAN | SEM | MEAN | SEM | MEAN | SEM | MEAN | SEM | MEAN | SEM | MEAN | SEM |
| SKIN | 3.96 | 0.87 | 2.91 | 0.94 | 1.85 | 0.45 | 1.51 | 0.33 | 7.15 | 0.70 | 3.67 | 0.89 | 5.44 | 0.42 | 7.78 | 1.48 |
| LIVER | 5.33 | 1.10 | 3.12 | 1.07 | 1.77 | 0.41 | 1.52 | 0.31 | 5.26 | 0.58 | 3.49 | 0.66 | 5.84 | 0.94 | 7.44 | 1.10 |
| SPLEEN | 3.30 | 0.78 | 1.62 | 0.41 | 0.99 | 0.20 | 1.22 | 0.27 | 9.16 | 2.24 | 6.82 | 2.03 | 9.34 | 1.53 | 9.97 | 2.29 |
| KIDNEY | 3.85 | 0.90 | 2.69 | 0.97 | 1.75 | 0.41 | 1.19 | 0.24 | 7.30 | 0.54 | 4.32 | 0.53 | 5.86 | 0.95 | 9.36 | 1.29 |
| ADRENAL | 5.37 | 1.11 | 3.27 | 1.37 | 2.23 | 0.59 | 1.74 | 0.59 | 5.55 | 1.43 | 3.09 | 1.52 | 1.56 | 3.20 | 8.46 | 1.93 |
| STOMACH | 1.85 | 0.27 | 1.51 | 0.49 | 1.28 | 0.28 | 0.76 | 0.10 | 14.84 | 1.52 | 7.34 | 2.09 | 7.44 | 1.32 | 14.47 | 2.54 |
| ST CONT | 0.89 | 0.35 | 0.56 | 0.08 | 1.17 | 0.26 | 0.64 | 0.09 | 40.38 | 12.13 | 26.51 | 10.51 | 8.30 | 1.66 | 19.09 | 5.53 |
| SM INT | 1.34 | 0.26 | 0.97 | 0.33 | 0.64 | 0.14 | 0.42 | 0.07 | 20.59 | 1.03 | 11.49 | 3.24 | 14.74 | 2.02 | 26.52 | 3.81 |
| LG INT | 1.31 | 0.11 | 1.26 | 0.36 | 0.91 | 0.22 | 0.52 | 0.11 | 20.52 | 2.02 | 8.51 | 2.47 | 11.70 | 1.95 | 22.19 | 3.26 |
| BLADDER | 3.92 | 0.62 | 2.20 | 0.83 | 1.58 | 0.42 | 1.31 | 0.28 | 7.03 | 0.64 | 2.02 | 3.60 | 7.13 | 1.65 | 8.70 | 1.23 |
| FEMUR | 1.15 | 0.28 | 0.99 | 0.36 | 0.67 | 0.17 | 0.45 | 0.11 | 25.15 | 3.80 | 11.48 | 3.21 | 15.93 | 2.70 | 25.61 | 3.61 |
| MUSCLE | 1.01 | 0.17 | 0.81 | 0.27 | 0.51 | 0.14 | 0.38 | 0.07 | 27.22 | 1.99 | 13.56 | 2.66 | 22.86 | 5.10 | 29.25 | 3.05 |
| TUMOR | 27.39 | 5.12 | 13.55 | 5.76 | 10.24 | 2.67 | 10.38 | 1.38 | 1.00 | 0.00 | 1.00 | 0.00 | 1.00 | 0.00 | 1.00 | 0.00 |
| HEART | 4.66 | 1.30 | 2.71 | 0.94 | 1.58 | 0.41 | 1.32 | 0.29 | 6.20 | 0.72 | 4.37 | 0.50 | 6.97 | 0.69 | 8.83 | 1.68 |
| LUNG | 6.27 | 1.35 | 4.63 | 1.56 | 2.46 | 0.66 | 1.96 | 0.47 | 4.49 | 0.43 | 2.53 | 0.42 | 4.72 | 0.76 | 6.14 | 1.14 |
| SPINE | 2.23 | 0.31 | 1.61 | 0.51 | 1.05 | 0.29 | 0.64 | 0.13 | 12.45 | 1.85 | 6.98 | 1.52 | 11.36 | 2.23 | 17.99 | 2.92 |
| BRAIN | 0.36 | 0.08 | 0.26 | 0.09 | 0.14 | 0.04 | 0.12 | 0.03 | 77.43 | 3.10 | 45.73 | 5.55 | 90.00 | 27.52 | 94.74 | 16.54 |
| BLOOD | 11.08 | 3.38 | 6.69 | 2.56 | 3.52 | 0.92 | 3.07 | 0.61 | 2.63 | 0.24 | 2.20 | 0.41 | 3.41 | 0.56 | 3.67 | 0.56 |

FIG. 5

ANTI-CHONDROITIN SULFATE PROTEOGLYCAN 4 ANTIBODIES AND USES THEREOF

CROSS REFERENCE TO RELATED APPLICATIONS

This application is the National Stage of International Application No. PCT/US15/60465, filed Nov. 12, 2015, which claims the benefit of U.S. Provisional Application No. 62/078,849, filed Nov. 12, 2014 the contents of both of which are hereby incorporated by reference herein in their entireties.

REFERENCE TO SEQUENCE LISTING

The specification includes a Sequence Listing in the form of an ASCII compliant text file named "Sequence Listing.txt", which was created on Dec. 16, 2015 and has a size of 92.8 kilobytes. The content of the aforementioned "Sequence Listing.txt" file is hereby incorporated by reference in its entirety.

BACKGROUND

Antibody-based therapeutics offer significant promise, particularly in cancer treatment. A variety of formats, including monoclonal, murine, chimeric, humanized, human, full-length, Fab, pegylated, radiolabeled, drug-conjugated, multi-specific, etc. are being developed. A 2012 review article, reported that 34 therapeutic antibody agents had received marketing approval in the United States or Europe (see Reichert, mAbs 4:3, 413, May/June 2012, incorporated herein by reference). Still, development of particular effective antibody agents remains a challenge.

SUMMARY OF INVENTION

The present invention provides, among other things, improved humanized antibodies that bind chondrotin sulfate proteoglycan 4 (CSPG4) and contain one or more structural features (e.g., one or more CDRs) of murine antibody 763.74 (referred to herein as 763). In some embodiments, provided antibody agents demonstrate high affinity and unusually slow $k_{off}$ rates as compared to parental murine antibody 763.74. In some embodiments, provided antibody agents have a high affinity to CSPG4 such that said antibody agents do not demonstrate affinity barrier issues.

The present invention also provides, improved multispecific binding agents that include binding moieties that interact with a particular target. In many embodiments, such binding moieties are or comprise antibody components. In some embodiments, multispecific binding agents of the present invention comprise binding elements of a humanized 763 antibody. In some embodiments, multispecific binding agents of the present invention comprise a first binding moiety based on a humanized 763 antibody and a second binding moiety that interacts with immune effector cell (e.g., a T cell). Such provided agents have improved functional characteristics as compared to parental binding agents that lack components described herein.

In some embodiments, the present invention provides a humanized or chimeric antibody or fragment thereof that binds CSPG4, wherein the humanized or chimeric antibody or fragment thereof comprises at least one, at least two, or three of the complementarity determining regions (CDRs) found in the light chain variable region of murine antibody 763 and/or at least one, at least two, or three of the CDRs found in the heavy chain variable region of murine antibody 763. In some embodiments, humanized or chimeric antibodies of the present invention comprise the three CDRs found in the light chain variable region of murine antibody 763 and the three CDRs found in the heavy chain variable region of murine antibody 763.

In some embodiments, an antibody of the present invention is humanized. In some certain embodiments, humanized antibodies of the present invention comprise a light chain variable region sequence of SEQ ID NO: 12 or SEQ ID NO: 14. In some certain embodiments, humanized antibodies of the present invention comprises a heavy chain variable region of SEQ ID NO: 8, SEQ ID NO: 10, SEQ ID NO: 16 or SEQ ID NO: 18.

In some embodiments, a humanized antibody of the present invention comprises a heavy chain variable region of SEQ ID NO: 8 and a light chain variable region of SEQ ID NO: 12. In some embodiments, a humanized antibody of the present invention comprises a heavy chain variable region of SEQ ID NO: 10 and a light chain variable region of SEQ ID NO: 14. In some embodiments, a humanized antibody of the present invention comprises a heavy chain variable region of SEQ ID NO: 16 and a light chain variable region of SEQ ID NO: 12. In some embodiments, a humanized antibody of the present invention comprises a heavy chain variable region of SEQ ID NO: 18 and a light chain variable region of SEQ ID NO: 14.

In some embodiments, a humanized antibody of the present invention comprises a heavy chain variable region of SEQ ID NO: 8 and a light chain variable region of SEQ ID NO: 14. In some embodiments, a humanized antibody of the present invention comprises a heavy chain variable region of SEQ ID NO: 10 and a light chain variable region of SEQ ID NO: 12. In some embodiments, a humanized antibody of the present invention comprises a heavy chain variable region of SEQ ID NO: 16 and a light chain variable region of SEQ ID NO: 14. In some embodiments, a humanized antibody of the present invention comprises a heavy chain variable region of SEQ ID NO: 18 and a light chain variable region of SEQ ID NO: 12.

In some embodiments, a humanized antibody of the present invention comprises the heavy chain of SEQ ID NO: 8 and the light chain of SEQ ID NO: 12. In some embodiments, a humanized antibody of the present invention comprises the heavy chain of SEQ ID NO: 10 and a light chain of SEQ ID NO: 14. In some embodiments, a humanized antibody of the present invention comprises the heavy chain of SEQ ID NO: 16 and the light chain of SEQ ID NO: 12. In some embodiments, a humanized antibody of the present invention comprises the heavy chain of SEQ ID NO: 18 and a light chain of SEQ ID NO: 14.

In some embodiments, a humanized antibody of the present invention comprises the heavy chain of SEQ ID NO: 8 and a light chain of SEQ ID NO: 14. In some embodiments, a humanized antibody of the present invention comprises the heavy chain of SEQ ID NO: 10 and a light chain of SEQ ID NO: 12. In some embodiments, a humanized antibody of the present invention comprises the heavy chain of SEQ ID NO: 16 and a light chain of SEQ ID NO: 14. In some embodiments, a humanized antibody of the present invention comprises the heavy chain of SEQ ID NO: 18 and a light chain of SEQ ID NO: 12.

In some embodiments, an antibody of the present invention is chimeric. In some certain embodiments, a chimeric antibody of the present invention comprises a light chain variable region sequence of SEQ ID NO: 6. In some certain embodiments, a chimeric antibody of the present invention comprises a heavy chain variable region of SEQ ID NO: 4. In some certain embodiments, a chimeric antibody of the present invention comprises the heavy chain of SEQ ID NO: 4 and the light chain of SEQ ID NO: 6.

In various embodiments, a humanized or chimeric antibody of the present invention is characterized in that it inhibits tumor uptake of SKMEI-28 xenographs by about 50% as compared to a reference antibody.

In various embodiments, a humanized or chimeric antibody of the present invention is glycosylated with terminal mannose, N-acetylglucose or glucose, but no fucose.

In various embodiments, a humanized or chimeric antibody of the present invention is or comprises a human IgG1 or a human IgG4.

In various embodiments, a humanized or chimeric antibody of the present invention is or comprises a human IgG1 that has a variant glycosylation. In some certain embodiments, variant glycosylation results from an amino acid substitution at residue 297 of the human IgG1 Fc. In some certain embodiments, variant glycosylation results from expression in a engineered cell line. In some embodiments, engineered cell lines include CHO cells; in some certain embodiments, engineered cell lines include GnT1-deficient CHO cells.

In some embodiments, the present invention provides an isolated nucleic acid molecule that encodes an amino acid sequence described herein. In some embodiments, isolated nucleic acid sequences of the present invention are codon-optimized. In some certain embodiments, isolated nucleic acid sequences are or comprise any one of SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19 and SEQ ID NO: 21.

In some embodiments, the present invention provides a recombinant or expression vector comprising a nucleic acid molecule as described herein.

In some embodiments, the present invention provides a host cell comprising a recombinant or expression vector as described herein.

In some embodiments, the present invention provides compositions comprising a humanized or chimeric antibody or fragment thereof as described herein.

In some embodiments, humanized or chimeric antibodies of the present invention are conjugated to a cytotoxic agent.

In some embodiments, the present invention provides a pharmaceutical composition comprising a humanized or chimeric antibody or fragment thereof as described herein or a composition as described herein and further comprise a pharmaceutically acceptable carrier or diluent.

In some embodiments, the present invention provides a method for producing a humanized or chimeric antibody or fragment thereof as described herein comprising a step of culturing a host cell as described herein in in a culture medium under conditions allowing the expression of the humanized or chimeric antibody or fragment thereof and separating the humanized or chimeric antibody or fragment thereof from the culture medium.

In some embodiments, the present invention provides a method of treating or preventing a medical condition in a subject, wherein the medical condition characterized by CSPG4 expression, the method comprising administering a therapeutically effective amount of an antibody or fragment thereof as described herein to said subject. In various embodiments, medical conditions include CSPG4-positive tumors. In various embodiments, medical conditions include melanoma, breast cancer, osteosarcoma, head and neck cancers, glioblastomas multiforme, sarcoma and/or mesothelioma.

In some embodiments, the present invention also provides a bispecific binding agent (e.g., a bispecific antibody) that comprises first and second antigen-binding sites. In many embodiments, first antigen-binding sites are or comprises antibody components derived from a humanized 763 antibody as described herein. In many embodiments, second antigen-binding sites are or comprise antibody components that bind to immune effector cells.

In some embodiments, the present invention provides a bispecific antibody comprising a first antigen-binding site derived from a humanized 763 antibody and a second antigen-binding site. In many embodiments, humanized 763 antibodies are or are based on humanized 763 antibodies described herein.

In some embodiments, first and second antigen-binding sites are or comprise single chain variable fragments (scFvs). In some embodiments, a first antigen-binding site is composed of an immunoglobulin molecule and a second antigen-binding site is composed of an scFv, scFab, Fab or Fv. In some certain embodiments, a second antigen-binding site is an scFv. In some certain embodiments, a first antigen binding site is composed of an immunoglobulin molecule and a second antigen-binding site is an scFv, wherein the scFv is linked to the C-terminal end of the heavy chain of the immunoglobulin. In some certain embodiments, a first antigen binding site is composed of an immunoglobulin molecule and a second antigen-binding site is an scFv, wherein the scFv is linked to the C-terminal end of the light chain of the immunoglobulin.

In various embodiments, a second antigen-binding site binds an immune cell selected from the group consisting of a T cell, NK cell, B cell, dendritic cell, monocyte, macrophage, neutrophil, mesenchymal stem cell and neural stem cell. In various embodiments, a second antigen binding site binds CD3.

In various embodiments, a bispecific antibody of the present invention comprise the sequence of SEQ ID NO: 20 or SEQ ID NO: 22. In some embodiments, the present invention provides an isolated nucleic acid comprising a coding sequence for part or all of a polypeptide chain of a bispecific antibody as described herein. In some certain embodiments, coding sequences are codon-optimized.

In some embodiments, the present invention provides a composition comprising a bispecific antibody as described herein.

In some embodiments, the present invention provides a pharmaceutical composition comprising a composition comprising a bispecific antibody as described herein or bispecific antibody as described herein.

In some embodiments, the present invention provides a chimeric antigen receptor comprising an antigen-binding domain of a humanized 763 antibody. In many embodiments, humanized 763 antibodies include such antibodies as described herein. In some embodiments, antigen-binding sites include scFvs.

In some embodiments, the present invention provides an immune effector cell that expresses a chimeric antigen receptor as described herein.

In some embodiments, the present invention provides use of a chimeric antigen receptor as described herein for the treatment or detection of a condition related to CSPG4 expression.

In some embodiments, the present invention provides a bispecific T-cell engaging monoclonal antibody comprising an antigen-binding site based on a humanized 763 antibody. In many embodiments, humanized 763 antibodies include such antibodies as described herein.

In some embodiments, the present invention provides a method of killing tumor cells, the method comprising the steps of contacting the tumor cells with a bispecific antibody, which bispecific antibody is composed of a first antigen-binding site based on a humanized 763 antibody and a second antigen-binding site that binds CD3, the contacting being performed under conditions and for a time sufficient that T cells to which the bispecific antibody has bound mediate killing of the tumor cells.

In some embodiments, the present invention provides a method of inhibiting tumor growth, the method comprising the steps of contacting a tumor with a bispecific antibody, which bispecific antibody is composed of a first antigen-binding site based on a humanized 763 antibody and a second antigen-binding site that binds CD3 on T cells, the contacting being performed under conditions and for a time sufficient that T cells to which the bispecific antibody has bound inhibit growth of a tumor.

In various embodiments, first and second antigen-binding sites are scFvs.

In various embodiments, a first antigen-binding site is composed of an immunoglobulin molecule and a second antigen-binding site is composed of an scFv. In some certain embodiments, an scFv is linked to the immunoglobulin molecule at the C-terminal end of the heavy chain. In some certain embodiments, an scFv is linked to the immunoglobulin molecule at the C-terminal end of the light chain.

In some embodiments, the present invention provides a bispecific antibody comprised of an immunoglobulin molecule that binds CSPG4 and an scFv that binds to CD3 on T cells, wherein the bispecific antibody is characterized by an increased efficiency to mediate T cell killing of tumor cells as compared to a reference bispecific antibody. In various embodiments, a bispecific antibody of the present invention is characterized by a high potency to kill tumor cells and a very low $EC_{50}$. In various embodiments, a bispecific antibody of the present invention is characterized by enhanced tumor $CSPG4^+$ tumor targeting as compared to a reference bispecific antibody. In various embodiments, a bispecific antibody of the present invention is characterized by no or substantially no aggregation as compared to a reference bispecific antibody. In various embodiments, a bispecific antibody of the present invention is characterized a greater binding avidity as compared to a reference bispecific antibody.

In some embodiments, an immunoglobulin molecule of a bispecific antibody of the present invention is based on murine 763 antibody.

In some embodiments, an scFv of a bispecific antibody of the present invention is based on a humanized OKT3 antibody. In some certain embodiments, an scFv is linked to the immunoglobulin molecule at the C-terminal end of the heavy or light chain.

In various embodiments, bispecific antibodies of the present invention comprise SEQ ID NO: 20 and SEQ ID NO: 14. In various embodiments, bispecific antibodies of the present invention comprise SEQ ID NO: 20 and/or SEQ ID NO: 12.

In various embodiments, bispecific antibodies of the present invention comprises SEQ ID NO: 22 and the heavy chain variable region of SEQ ID NO: 8, SEQ ID NO: 10, SEQ ID NO: 16 or SEQ ID NO: 18. In various embodiments, bispecific antibodies of the present invention comprise SEQ ID NO: 22 and one of SEQ ID NO: 8, SEQ ID NO: 10, SEQ ID NO: 16 or SEQ ID NO: 18.

In some embodiments, the present invention provides a kit comprising a humanized 763 antibody or a bispecific antibody described herein.

In some embodiments, the present invention provides use of a humanized 763 antibody or bispecific antibody described herein in the manufacture of a medicament for use in medicine. In some embodiments, the present invention provides use of a humanized 763 antibody or bispecific antibody described herein in the manufacture of a medicament for use in a diagnostic test or assay. In some embodiments, the present invention provides use of a humanized 763 antibody or bispecific antibody described herein in the manufacture of a medicament for the diagnosis of cancer. In some embodiments, the present invention provides use of a humanized 763 antibody or bispecific antibody described herein in the manufacture of a medicament for the treatment of cancer. In some embodiments, the present invention provides use of a humanized 763 antibody or bispecific antibody described herein in the manufacture of a medicament for the treatment of melanoma, breast cancer, osteosarcoma, head and neck cancers, glioblastoma multiforme, sarcoma or mesothelioma.

BRIEF DESCRIPTION OF THE DRAWING

The Drawing included herein, which is composed of the following Figures, is for illustration purposes only not for limitation.

FIG. 5 shows exemplary targeting of $^{124}I$-labelled humanized 763 antibodies to SKMEL-28 xenografts.

DEFINITIONS

Figure 1:
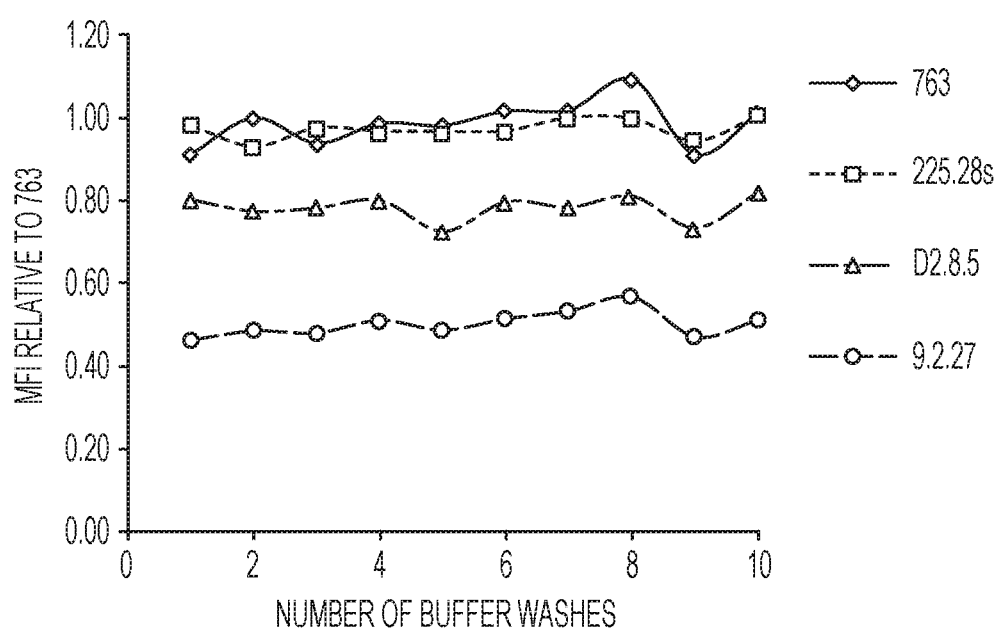
FIG. 1 shows exemplary mean fluorescence intensity for anti-CSPG4 antibody binding to $CSPG4^+$ M14 tumor cells after multiple washes with a wash buffer (PBS with 2 mM EDTA).

This invention is not limited to particular methods, and experimental conditions described, as such methods and conditions may vary. It is also to be understood that the terminology used herein is for the purpose of describing particular embodiments only, and is not intended to be limiting, since the scope of the present invention is defined by the claims.

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described. The contents of all cited references (including non-patent literature references, issued patents, published patent applications, and co-pending patent applications) cited throughout this application are hereby expressly incorporated by reference.

In order for the present invention to be more readily understood, certain terms are first defined below. Additional definitions for the following terms and other terms are set forth through the specification.

"Affinity": As is known in the art, "affinity" is a measure of the tightness with a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

"Affinity matured" (or "affinity matured antibody"), as used herein, refers to an antibody with one or more alterations in one or more CDRs thereof which result an improvement in the affinity of the antibody for antigen, compared to a parent antibody which does not possess those alteration(s). In some embodiments, affinity matured antibodies will have nanomolar or even picomolar affinities for a target antigen. Affinity matured antibodies may be produced by any of a variety of procedures known in the art. Marks et al., Bio-Technology 10:779-783 (1992) describes affinity maturation by $V_H$ and $V_L$ domain shuffling. Random mutagenesis of CDR and/or framework residues is described by: Barbas et al. Proc. Nat. Acad. Sci. U.S.A 91:3809-3813 (1994); Schier et al., Gene 169: 147-155 (1995); Yelton et al., J. Immunol. 155: 1994-2004 (1995); Jackson et al., J. Immunol. 154(7): 3310-9 (1995); and Hawkins et al., J. Mol. Biol. 226:889-896 (1992).

"Amelioration", as used herein, refers to the prevention, reduction or palliation of a state, or improvement of the state of a subject. Amelioration includes, but does not require complete recovery or complete prevention of a disease, disorder or condition (e.g., radiation injury).

"Animal", as used herein refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In certain embodiments, the animal is susceptible to infection by DV. In some embodiments, an animal may be a transgenic animal, genetically engineered animal, and/or a clone.

"Antibody", as used herein, has its art understood meaning and refers to an immunoglobulin (Ig) that binds specifically to a particular antigen. As is known by those of ordinary skill in the art, antibodies produced in nature are typically comprised of four polypeptide chains, two heavy (H) chains and two light (L) chains. Each heavy and light chain is comprised of a variable region (abbreviated herein as HCVR or $V_H$ and LCVR or $V_L$, respectively) and a constant region. The constant region of a heavy chain comprises a $C_H1$, $C_H2$ and $C_H3$ domain (and optionally a $C_H4$ domain in the case of IgM and IgE). The constant region of a light chain is comprised of one domain, $C_L$. The $V_H$ and $V_L$ regions further contain regions of hypervariability, termed complementarity determining regions (CDRs), interspersed with regions that are more conserved, which are termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgM, IgD, IgG, IgA and IgE), class (e.g., IgG1, IgG2, IgG3, IgG4, IgA1 and IgA2) or subclass.

Antibody agent: As used herein, the term "antibody agent" refers to an agent that specifically binds to a particular antigen. In some embodiments, the term encompasses any polypeptide with immunoglobulin structural elements sufficient to confer specific binding. In various embodiments, suitable antibody agents may include, but are not limited to, monoclonal antibodies, polyclonal antibodies, humanized antibodies, primatized antibodies, chimeric antibodies, human antibodies, bi-specific or multi-specific antibodies, single domain antibodies (e.g., shark single domain antibodies (e.g., IgNAR or fragments thereof)), conjugated antibodies (i.e., antibodies conjugated or fused to other proteins, radiolabels, cytotoxins), Small Modular Immuno-Pharmaceuticals ("SMIPsTM"), single chain antibodies, cameloid antibodies, antibody fragments, etc. In some embodiments, the term can refer to a stapled peptide. In some embodiments, the term can refer to an antibody-like binding peptidomimetic. In some embodiments, the term can refer to an antibody-like binding scaffold protein. In some embodiments, the term can refer to monobodies or adnectins. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain, which is homologous or largely homologous to an immunoglobulin-binding domain. In some embodiments, an antibody agent is or comprises a polypeptide that includes all CDRs found in a particular reference antibody chain or chains (e.g., heavy chain and/or light chain).

"Antibody component", as used herein, refers to a polypeptide element (that may be a complete polypeptide, or a portion of a larger polypeptide, such as for example a fusion polypeptide as described herein) that specifically binds to an epitope or antigen and includes one or more immunoglobulin structural features. In general, an antibody component is any polypeptide whose amino acid sequence includes elements characteristic of an antibody-binding region (e.g., an antibody light chain or variable region or one or more complementarity determining regions ("CDRs") thereof, or an antibody heavy chain or variable region or one more CDRs thereof, optionally in presence of one or more framework regions). In some embodiments, an antibody component is or comprises a full-length antibody. In some embodiments, an antibody component is less than full-length but includes at least one binding site (comprising at least one, and preferably at least two sequences with structure of known antibody "variable regions"). In some embodiments, the term "antibody component" encompasses any protein having a binding domain, which is homologous or largely homologous to an immunoglobulin-binding domain. In particular embodiments, an included "antibody component" encompasses polypeptides having a binding domain that shows at least 99% identity with an immunoglobulin binding domain. In some embodiments, an included "antibody component" is any polypeptide having a binding domain that shows at least 70%, 75%, 80%, 85%, 90%, 95% or 98% identity with an immunoglobulin binding domain, for example a reference immunoglobulin binding domain. An included "antibody component" may have an amino acid sequence identical to that of an antibody (or a portion thereof, e.g., an antigen-binding portion thereof) that is found in a natural source. An antibody component may be monospecific, bi-specific, or multi-specific. An antibody component may include structural elements characteristic of any immunoglobulin class, including any of the human classes: IgG, IgM, IgA, IgD, and IgE. It has been shown that the antigen-binding function of an antibody can be performed by fragments of a full-length antibody. Such antibody embodiments may also be bispecific, dual specific, or multi-specific formats specifically binding to two or more different antigens. Examples of binding fragments encompassed within the term "antigen-binding portion" of an antibody include (i) a Fab fragment, a monovalent fragment consisting of the $V_H$, $V_L$, $C_H1$ and $C_L$ domains; (ii) a F(ab')$_2$ fragment, a bivalent fragment comprising two Fab fragments linked by a disulfide bridge at the hinge region; (iii) a Fd fragment consisting of the $V_H$ and $C_H1$ domains; (iv) a Fv fragment consisting of the $V_H$ and $V_L$ domains of a single arm of an antibody, (v) a dAb fragment (Ward et al., (1989) Nature 341:544-546), which comprises a single variable domain; and (vi) an isolated complementarity determining region (CDR). Furthermore, although the two domains of the Fv fragment, $V_H$ and $V_L$, are coded for by separate genes, they can be joined, using recombinant methods, by a synthetic linker that enables them to be made as a single protein chain in which the $V_H$ and $V_L$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). In some embodiments, an "antibody component", as described herein, is or comprises such a single chain antibody. In some embodiments, an "antibody component" is or comprises a diabody. Diabodies are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al., (1993) Proc. Natl. Acad. Sci. USA 90:6444-6448; Poljak, R. J., (1994) Structure 2(12):1121-1123). Such antibody binding portions are known in the art (Kontermann and Dubel eds., Antibody Engineering (2001) Springer-Verlag. New York. 790 pp. (ISBN 3-540-41354-5). In some embodiments, an antibody component is or comprises a single chain "linear antibody" comprising a pair of tandem Fv segments ($V_H$—$C_H$1-$V_H$-$C_H$1) which, together with complementary light chain polypeptides, form a pair of antigen binding regions (Zapata et al., (1995) Protein Eng. 8(10): 1057-1062; and U.S. Pat. No. 5,641,870). In some embodiments, an antibody component may have structural elements characteristic of chimeric or humanized antibodies. In general, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some embodiments, an antibody component may have structural elements characteristic of a human antibody.

"Biological activity", as used herein, refers to an observable biological effect or result achieved by an agent or entity of interest. For example, in some embodiments, a specific binding interaction is a biological activity. In some embodiments, modulation (e.g., induction, enhancement, or inhibition) of a biological pathway or event is a biological activity. In some embodiments, presence or extent of a biological activity is assessed through detection of a direct or indirect product produced by a biological pathway or event of interest.

"Bispecific antibody", as used herein, refers to a bispecific binding agent in which at least one, and typically both, of the binding moieties is or comprises an antibody component. A variety of different bi-specific antibody structures are known in the art. In some embodiments, each binding moiety in a bispecific antibody that is or comprises an antibody component includes $V_H$ and/or $V_L$ regions; in some such embodiments, the $V_H$ and/or $V_L$ regions are those found in a particular monoclonal antibody. In some embodiments, where the bispecific antibody contains two antibody component-binding moieties, each includes $V_H$ and/or $V_L$ regions from different monoclonal antibodies. In some embodiments, where the bispecific antibody contains two antibody component binding moieties, wherein one of the two antibody component binding moieties includes an immunoglobulin molecule having $V_H$ and/or $V_L$ regions that contain CDRs from a first monoclonal antibody, and one of the two antibody component binding moieties includes an antibody fragment (e.g., Fab, F(ab'), F(ab')$_2$, Fd, Fv, dAB, scFv, etc.) having $V_H$ and/or $V_L$ regions that contain CDRs from a second monoclonal antibody.

"Bispecific binding agent", as used herein, refers to a polypeptide agent with two discrete binding moieties, each of which binds with a distinct target. In some embodiments, a bispecific binding agent is or comprises a single polypeptide; in some embodiments, a bispecific binding agent is or comprises a plurality of peptides which, in some such embodiments may be covalently associated with one another, for example by cross-linking. In some embodiments, the two binding moieties of a bispecific binding agent recognize different sites (e.g., epitopes) the same target (e.g., antigen); in some embodiments, they recognize different targets. In some embodiments, a bispecific binding agent is capable of binding simultaneously to two targets that are of different structure.

"Carrier", as used herein, refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

"CDR", as used herein, refers to a complementarity determining region within an antibody variable region. There are three CDRs in each of the variable regions of the heavy chain and the light chain, which are designated CDR1, CDR2 and CDR3, for each of the variable regions. A "set of CDRs" or "CDR set" refers to a group of three or six CDRs that occur in either a single variable region capable of binding the antigen or the CDRs of cognate heavy and light chain variable regions capable of binding the antigen. Certain systems have been established in the art for defining CDR boundaries (e.g., Kabat, Chothia, etc.); those skilled in the art appreciate the differences between and among these systems and are capable of understanding CDR boundaries to the extent required to understand and to practice the claimed invention.

"CDR-grafted antibody", as used herein, refers to an antibody whose amino acid sequence comprises heavy and light chain variable region sequences from one species but in which the sequences of one or more of the CDR regions of $V_H$ and/or $V_L$ are replaced with CDR sequences of another species, such as antibodies having murine $V_H$ and $V_L$ regions in which one or more of the murine CDRs (e.g., CDR3) has been replaced with human CDR sequences. Likewise, a "CDR-grafted antibody" may also refer to antibodies having human $V_H$ and $V_L$ regions in which one or more of the human CDRs (e.g., CDR3) has been replaced with mouse CDR sequences.

"Chimeric antibody", as used herein, refers to an antibody whose amino acid sequence includes $V_H$ and $V_L$ region sequences that are found in a first species and constant region sequences that are found in a second species, different from the first species. In many embodiments, a chimeric antibody has murine $V_H$ and $V_L$ regions linked to human constant regions. In some embodiments, an antibody with human $V_H$ and $V_L$ regions linked to non-human constant regions (e.g., a mouse constant region) is referred to as a "reverse chimeric antibody".

"Comparable", as used herein, refers to two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

"Corresponding to", as used herein designates the position/identity of an amino acid residue in a polypeptide of interest. Those of ordinary skill will appreciate that, for purposes of simplicity, residues in a polypeptide are often designated using a canonical numbering system based on a reference related polypeptide, so that an amino acid "corresponding to" a residue at position 190, for example, need not actually be the 190$^{th}$ amino acid in a particular amino acid chain but rather corresponds to the residue found at 190 in the reference polypeptide; those of ordinary skill in the art readily appreciate how to identify "corresponding" amino acids.

"Dosage form" and "unit dosage form", as used herein, the term "dosage form" refers to physically discrete unit of a therapeutic agent for a subject (e.g., a human patient) to be treated. Each unit contains a predetermined quantity of active material calculated or demonstrated to produce a desired therapeutic effect when administered to a relevant population according to an appropriate dosing regimen. For example, in some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). It will be understood, however, that the total dosage administered to any particular patient will be selected by a medical professional (e.g., a medical doctor) within the scope of sound medical judgment.

"Dosing regimen" (or "therapeutic regimen"), as used herein is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regime comprises a plurality of doses and at least two different time periods separating individual doses. In some embodiments, the therapeutic agent is administered continuously (e.g., by infusion) over a predetermined period. In some embodiments, a therapeutic agent is administered once a day (QD) or twice a day (BID). In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount In some embodiments, a dosing regimen is correlated with a desired or beneficial outcome when administered across a relevant population (i.e., is a therapeutic dosing regimen).

"Effector function" as used herein refers a biochemical event that results from the interaction of an antibody Fc region with an Fc receptor or ligand. Effector functions include but are not limited to antibody-dependent cell-mediated cytotoxicity (ADCC), antibody-dependent cell-mediated phagocytosis (ADCP), and complement-mediated cytotoxicity (CMC). In some embodiments, an effector function is one that operates after the binding of an antigen, one that operates independent of antigen binding, or both.

"Effector cell" as used herein refers to a cell of the immune system that expresses one or more Fc receptors and mediates one or more effector functions. In some embodiments, effector cells may include, but may not be limited to, one or more of monocytes, macrophages, neutrophils, dendritic cells, eosinophils, mast cells, platelets, large granular lymphocytes, Langerhans' cells, natural killer (NK) cells, T-lymphocytes, B-lymphocytes and may be from any organism including but not limited to humans, mice, rats, rabbits, and monkeys.

"Epitope", as used herein, includes any moiety that is specifically recognized by an immunoglobulin (e.g., antibody or receptor) binding component. In some embodiments, an epitope is comprised of a plurality of chemical atoms or groups on an antigen. In some embodiments, such chemical atoms or groups are surface-exposed when the antigen adopts a relevant three-dimensional conformation. In some embodiments, such chemical atoms or groups are physically near to each other in space when the antigen adopts such a conformation. In some embodiments, at least some such chemical atoms are groups are physically separated from one another when the antigen adopts an alternative conformation (e.g., is linearized).

"Excipient", as used herein, refers to a non-therapeutic agent that may be included in a pharmaceutical composition, for example to provide or contribute to a desired consistency or stabilizing effect. Suitable pharmaceutical excipients include, for example, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

"Fc ligand" as used herein refers to a molecule, preferably a polypeptide, from any organism that binds to the Fc region of an antibody to form an Fc-ligand complex. Fc ligands include but are not limited to FcγRIIA (CD32A), FcγRIIB (CD32B), FcγRIIIA (CD16A), FcγRIIIB (CD16B), FcγRI (CD64), FcγRII (CD23), FcRn, C1q, C3, staphylococcal protein A, streptococcal protein G, and viral FcγR. Fc ligands may include undiscovered molecules that bind Fc.

"Framework" or "framework region", as used herein, refers to the sequences of a variable region minus the CDRs. Because a CDR sequence can be determined by different systems, likewise a framework sequence is subject to correspondingly different interpretations. The six CDRs divide the framework regions on the heavy and light chains into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FRs within the variable region of a single, naturally occurring immunoglobulin chain. As used herein, a FR represents one of the four sub-regions, FR1, for example, represents the first framework region closest to the amino terminal end of the variable region and 5' with respect to CDR1, and FRs represents two or more of the sub-regions constituting a framework region.

"Host cell", as used herein, refers to a cell into which exogenous DNA (recombinant or otherwise) has been introduced. Persons of skill upon reading this disclosure will understand that such terms refer not only to the particular subject cell, but also to the progeny of such a cell. Because certain modifications may occur in succeeding generations due to either mutation or environmental influences, such progeny may not, in fact, be identical to the parent cell, but are still included within the scope of the term "host cell" as used herein. In some embodiments, host cells include prokaryotic and eukaryotic cells selected from any of the Kingdoms of life that are suitable for expressing an exogenous DNA (e.g., a recombinant nucleic acid sequence). Exemplary cells include those of prokaryotes and eukaryotes (single-cell or multiple-cell), bacterial cells (e.g., strains of *E. coli, Bacillus* spp., *Streptomyces* spp., etc.), mycobacteria cells, fungal cells, yeast cells (e.g., *S. cerevisiae, S. pombe, P. pastoris, P. methanolica*, etc.), plant cells, insect cells (e.g., SF-9, SF-21, baculovirus-infected insect cells, *Trichoplusia ni*, etc.), non-human animal cells, human cells, or cell fusions such as, for example, hybridomas or quadromas. In some embodiments, the cell is a human, monkey, ape, hamster, rat, or mouse cell. In some embodiments, the cell is eukaryotic and is selected from the following cells:

CHO (e.g., CHO K1, DXB-1 1 CHO, Veggie-CHO), COS (e.g., COS-7), retinal cell, Vero, CV1, kidney (e.g., HEK293, 293 EBNA, MSR 293, MDCK, HaK, BHK), HeLa, HepG2, WI38, MRC 5, Colo205, HB 8065, HL-60, (e.g., BHK21), Jurkat, Daudi, A431 (epidermal), CV-1, U937, 3T3, L cell, C127 cell, SP2/0, NS-0, MMT 060562, Sertoli cell, BRL 3 A cell, HT1080 cell, myeloma cell, tumor cell, and a cell line derived from an aforementioned cell. In some embodiments, the cell comprises one or more viral genes, e.g., a retinal cell that expresses a viral gene (e.g., a PER.C6™ cell).

"Human antibody", as used herein, is intended to include antibodies having variable and constant regions generated (or assembled) from human immunoglobulin sequences. In some embodiments, antibodies (or antibody components) may be considered to be "human" even though their amino acid sequences include residues or elements not encoded by human germline immunoglobulin sequences (e.g., include sequence variations, for example that may (originally) have been introduced by random or site-specific mutagenesis in vitro or by somatic mutation in vivo), for example in one or more CDRs and in particular CDR3.

"Humanized", as is known in the art, the term "humanized" is commonly used to refer to antibodies (or antibody components) whose amino acid sequence includes $V_H$ and $V_L$ region sequences from a reference antibody raised in a non-human species (e.g., a mouse), but also includes modifications in those sequences relative to the reference antibody intended to render them more "human-like", i.e., more similar to human germline variable sequences. In some embodiments, a "humanized" antibody (or antibody component) is one that immunospecifically binds to an antigen of interest and that has a framework (FR) region having substantially the amino acid sequence as that of a human antibody, and a complementary determining region (CDR) having substantially the amino acid sequence as that of a non-human antibody. A humanized antibody comprises substantially all of at least one, and typically two, variable domains (Fab, Fab', F(ab)$_2$, FabC, Fv) in which all or substantially all of the CDR regions correspond to those of a non-human immunoglobulin (i.e., donor immunoglobulin) and all or substantially all of the framework regions are those of a human immunoglobulin consensus sequence. In some embodiments, a humanized antibody also comprises at least a portion of an immunoglobulin constant region (Fc), typically that of a human immunoglobulin constant region. In some embodiments, a humanized antibody contains both the light chain as well as at least the variable domain of a heavy chain. The antibody also may include a $C_H1$, hinge, $C_H2$, $C_H3$, and, optionally, a $C_H4$ region of a heavy chain constant region. In some embodiments, a humanized antibody only contains a humanized $V_L$ region. In some embodiments, a humanized antibody only contains a humanized $V_H$ region. In some certain embodiments, a humanized antibody contains humanized $V_H$ and $V_L$ regions.

"Improve," "increase" or "reduce," as used herein or grammatical equivalents thereof, indicate values that are relative to a baseline measurement, such as a measurement in the same individual prior to initiation of a treatment described herein, or a measurement in a control individual (or multiple control individuals) in the absence of the treatment described herein. A "control individual" is an individual afflicted with the same form of disease or injury as the individual being treated.

"In vitro", as used herein refers to events that occur in an artificial environment, e.g., in a test tube or reaction vessel, in cell culture, etc., rather than within a multi-cellular organism.

"In vivo", as used herein refers to events that occur within a multi-cellular organism, such as a human and a non-human animal. In the context of cell-based systems, the term may be used to refer to events that occur within a living cell (as opposed to, for example, in vitro systems).

"Isolated", as used herein, refers to a substance and/or entity that has been (1) separated from at least some of the components with which it was associated when initially produced (whether in nature and/or in an experimental setting), and/or (2) designed, produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. In some embodiments, as will be understood by those skilled in the art, a substance may still be considered "isolated" or even "pure", after having been combined with certain other components such as, for example, one or more carriers or excipients (e.g., buffer, solvent, water, etc.); in such embodiments, percent isolation or purity of the substance is calculated without including such carriers or excipients. To give but one example, in some embodiments, a biological polymer such as a polypeptide or polynucleotide that occurs in nature is considered to be "isolated" when, a) by virtue of its origin or source of derivation is not associated with some or all of the components that accompany it in its native state in nature; b) it is substantially free of other polypeptides or nucleic acids of the same species from the species that produces it in nature; c) is expressed by or is otherwise in association with components from a cell or other expression system that is not of the species that produces it in nature. Thus, for instance, in some embodiments, a polypeptide that is chemically synthesized or is synthesized in a cellular system different from that which produces it in nature is considered to be an "isolated" polypeptide. Alternatively or additionally, in some embodiments, a polypeptide that has been subjected to one or more purification techniques may be considered to be an "isolated" polypeptide to the extent that it has been separated from other components a) with which it is associated in nature; and/or b) with which it was associated when initially produced.

"$K_D$", as used herein, refers to the dissociation constant of a binding agent (e.g., an antibody or binding component thereof) from a complex with its partner (e.g., the epitope to which the antibody or binding component thereof binds).

"$K_{off}$", as used herein, refers to the off rate constant for dissociation of a binding agent (e.g., an antibody or binding component thereof) from a complex with its partner (e.g., the epitope to which the antibody or binding component thereof binds).

"$K_{on}$", as used herein, refers to the on rate constant for association of a binding agent (e.g., an antibody or binding component thereof) with its partner (e.g., the epitope to which the antibody or binding component thereof binds).

"Linker", as used herein, is used to refer to that portion of a multi-element polypeptide that connects different elements to one another. For example, those of ordinary skill in the art appreciate that a polypeptide whose structure includes two or more functional or organizational domains often includes a stretch of amino acids between such domains that links them to one another. In some embodiments, a polypeptide comprising a linker element has an overall structure of the general form S1-L-S2, wherein S1 and S2 may be the same or different and represent two domains associated with one another by the linker. In some embodiments, a linker is at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, 100 or more amino acids in length. In some embodiments, a linker is characterized in that it tends not to adopt a rigid three-dimensional structure, but rather provides flexibility to the polypeptide. A variety of different linker elements that can appropriately be used when engineering polypeptides (e.g., fusion polypeptides) known in the art (see e.g., Holliger, P., et al. (1993) Proc. Natl. Acad. Sci. USA 90:6444-6448; Poljak, R. J., et al. (1994) Structure 2: 1 121-1123).

"Multivalent binding agent", as used herein, refers a binding agent capable of binding to two or more antigens, which can be on the same molecule or on different molecules. Multivalent binding agents as described herein are, in some embodiments, engineered to have the three or more antigen binding sites, and are typically not naturally occurring proteins. Multivalent binding agents as described herein refer to binding agents capable of binding two or more related or unrelated targets. Multivalent binding agents may be composed of multiple copies of a single antibody component or multiple copies of different antibody components. Such binding agents are capable of binding to two or more antigens and are tetravalent or multivalent binding agents. Multivalent binding agents may additionally comprise a therapeutic agent, such as, for example, an immunomodulator, toxin or an RNase. Multivalent binding agents as described herein are, in some embodiments, capable of binding simultaneously to at least two targets that are of different structure, e.g., two different antigens, two different epitopes on the same antigen, or a hapten and/or an antigen or epitope. In many embodiments, multivalent binding agents of the present invention are proteins engineered to have characteristics of multivalent binding agents as described herein. Multivalent binding agents of the present invention may be monospecific (capable of binding one antigen) or multispecific (capable of binding two or more antigens), and may be composed of two heavy chain polypeptides and two light chain polypeptides. Each binding site, in some embodiments, is composed of a heavy chain variable domain and a light chain variable domain with a total of six CDRs involved in antigen binding per antigen binding site.

"Nucleic acid", as used herein, in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to individual nucleic acid residues (e.g., nucleotides and/or nucleosides); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present invention. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxy guanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 20, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is single stranded; in some embodiments, a nucleic acid is double stranded. In some embodiments a nucleic acid has a nucleotide sequence comprising at least one element that encodes, or is the complement of a sequence that encodes, a polypeptide. In some embodiments, a nucleic acid has enzymatic activity.

"Operably linked", as used herein, refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism. For example, in prokaryotes, such control sequences generally include promoter, ribosomal binding site, and transcription termination sequence, while in eukaryotes, typically, such control sequences include promoters and transcription termination sequence. The term "control sequences" is intended to include components whose presence is essential for expression and processing, and can also include additional components whose presence is advantageous, for example, leader sequences and fusion partner sequences.

"Physiological conditions"", as used herein, has its art-understood meaning referencing conditions under which cells or organisms live and/or reproduce. In some embodiments, the term refers to conditions of the external or internal mileu that may occur in nature for an organism or cell system. In some embodiments, physiological conditions are those conditions present within the body of a human or non-human animal, especially those conditions present at and/or within a surgical site. Physiological conditions typically include, e.g., a temperature range of 20-40° C., atmospheric pressure of 1, pH of 6-8, glucose concentration of 1-20 mM, oxygen concentration at atmospheric levels, and gravity as it is encountered on earth. In some embodiments, conditions in a laboratory are manipulated and/or maintained at physiologic conditions. In some embodiments, physiological conditions are encountered in an organism.

"Polypeptide", as used herein, refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (i.e., a conserved region that may in some embodiments may be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a useful polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide "Prevent" or "prevention", as used herein when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

"Recombinant", as used herein, is intended to refer to polypeptides (e.g., antibodies or antibody components, or multispecific binding agents as described herein) that are designed, engineered, prepared, expressed, created or isolated by recombinant means, such as polypeptides expressed using a recombinant expression vector transfected into a host cell, polypeptides isolated from a recombinant, combinatorial human polypeptide library (Hoogenboom H. R., (1997) TIB Tech. 15:62-70; Azzazy H., and Highsmith W. E., (2002) Clin. Biochem. 35:425-445; Gavilondo J. V., and Larrick J. W. (2002) BioTechniques 29: 128-145; Hoogenboom H., and Chames P. (2000) Immunology Today 21:371-378), antibodies isolated from an animal (e.g., a mouse) that is transgenic for human immunoglobulin genes (see e.g., Taylor, L. D., et al. (1992) Nucl. Acids Res. 20:6287-6295; Little M. et al. (2000) Immunology Today 21:364-370; Kellermann S-A., and Green L. L. (2002) Current Opinion in Biotechnology 13:593-597; Murphy, A. J. et al., (2014) Proc. Natl. Acad. Sci. U.S.A. 111(14):5153-5158) or polypeptides prepared, expressed, created or isolated by any other means that involves splicing selected sequence elements to one another. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source. For example, in some embodiments, a recombinant antibody polypeptide is comprised of sequences found in the germline of a source organism of interest (e.g., human, mouse, etc.). In some embodiments, a recombinant antibody has an amino acid sequence that resulted from mutagenesis (e.g., in vitro or in vivo, for example in a transgenic animal), so that the amino acid sequences of the $V_H$ and $V_L$ regions of the recombinant antibodies are sequences that, while originating from and related to germline $V_H$ and $V_L$ sequences, may not naturally exist within the germline antibody repertoire in vivo.

"Recovering", as used herein, refers to the process of rendering an agent or entity substantially free of other previously-associated components, for example by isolation, e.g., using purification techniques known in the art. In some embodiments, an agent or entity is recovered from a natural source and/or a source comprising cells.

"Reference", as used herein describes a standard or control agent, animal, individual, population, sample, sequence or value against which an agent, animal, individual, population, sample, sequence or value of interest is compared. In some embodiments, a reference agent, animal, individual, population, sample, sequence or value is tested and/or determined substantially simultaneously with the testing or determination of the agent, animal, individual, population, sample, sequence or value of interest. In some embodiments, a reference agent, animal, individual, population, sample, sequence or value is a historical reference, optionally embodied in a tangible medium. Typically, as would be understood by those skilled in the art, a reference agent, animal, individual, population, sample, sequence or value is determined or characterized under conditions comparable to those utilized to determine or characterize the agent, animal, individual, population, sample, sequence or value of interest.

"Risk", as will be understood from context, "risk" of a disease, disorder, and/or condition comprises likelihood that a particular individual will develop a disease, disorder, and/or condition (e.g., a radiation injury). In some embodiments, risk is expressed as a percentage. In some embodiments, risk is from 0, 1, 2, 3, 4, 5, 6, 7, 8, 9, 10, 20, 30, 40, 50, 60, 70, 80, 90 up to 100%. In some embodiments risk is expressed as a risk relative to a risk associated with a reference sample or group of reference samples. In some embodiments, a reference sample or group of reference samples have a known risk of a disease, disorder, condition and/or event (e.g., a radiation injury). In some embodiments a reference sample or group of reference samples are from individuals comparable to a particular individual. In some embodiments, relative risk is 0, 1, 2, 3, 4, 5, 6, 7, 8, 9, 10, or more.

"Specific binding", as used herein, refers to a binding agent's ability to discriminate between possible partners in the environment in which binding is to occur. A binding agent that interacts with one particular target when other potential targets are present is said to "bind specifically" to the target with which it interacts. In some embodiments, specific binding is assessed by detecting or determining degree of association between the binding agent and its partner; in some embodiments, specific binding is assessed by detecting or determining degree of dissociation of a binding agent-partner complex; in some embodiments, specific binding is assessed by detecting or determining ability of the binding agent to compete an alternative interaction between its partner and another entity. In some embodiments, specific binding is assessed by performing such detections or determinations across a range of concentrations.

"Subject", as used herein, means any mammal, including humans. In certain embodiments of the present invention the subject is an adult, an adolescent or an infant. In some embodiments, terms "individual" or "patient" are used and are intended to be interchangeable with "subject". Also contemplated by the present invention are the administration of the pharmaceutical compositions and/or performance of the methods of treatment in-utero.

"Substantially": As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

"Substantial sequence homology", as used herein refers to a comparison between amino acid or nucleic acid sequences. As will be appreciated by those of ordinary skill in the art, two sequences are generally considered to be "substantially homologous" if they contain homologous residues in corresponding positions. Homologous residues may be identical residues. Alternatively, homologous residues may be non-identical residues will appropriately similar structural and/or functional characteristics. For example, as is well known by those of ordinary skill in the art, certain amino acids are typically classified as "hydrophobic" or "hydrophilic" amino acids, and/or as having "polar" or "non-polar" side chains. Substitution of one amino acid for another of the same type may often be considered a "homologous" substitution. Typical amino acid categorizations are summarized in Table 1 and 2.

TABLE 1

| Alanine | Ala | A | Nonpolar | Neutral | 1.8 |
| Arginine | Arg | R | Polar | Positive | −4.5 |
| Asparagine | Asn | N | Polar | Neutral | −3.5 |
| Aspartic acid | Asp | D | Polar | Negative | −3.5 |
| Cysteine | Cys | C | Nonpolar | Neutral | 2.5 |
| Glutamic acid | Glu | E | Polar | Negative | −3.5 |
| Glutamine | Gln | Q | Polar | Neutral | −3.5 |
| Glycine | Gly | G | Nonpolar | Neutral | −0.4 |
| Histidine | His | H | Polar | Positive | −3.2 |
| Isoleucine | Ile | I | Nonpolar | Neutral | 4.5 |
| Leucine | Leu | L | Nonpolar | Neutral | 3.8 |
| Lysine | Lys | K | Polar | Positive | −3.9 |
| Methionine | Met | M | Nonpolar | Neutral | 1.9 |
| Phenylalanine | Phe | F | Nonpolar | Neutral | 2.8 |
| Proline | Pro | P | Nonpolar | Neutral | −1.6 |
| Serine | Ser | S | Polar | Neutral | −0.8 |
| Threonine | Thr | T | Polar | Neutral | −0.7 |
| Tryptophan | Trp | W | Nonpolar | Neutral | −0.9 |
| Tyrosine | Tyr | Y | Polar | Neutral | −1.3 |
| Valine | Val | V | Nonpolar | Neutral | 4.2 |

TABLE 2

| Ambiguous Amino Acids | 3-Letter | 1-Letter |
|---|---|---|
| Asparagine or aspartic acid | Asx | B |
| Glutamine or glutamic acid | Glx | Z |

TABLE 2-continued

| Ambiguous Amino Acids | 3-Letter | 1-Letter |
| --- | --- | --- |
| Leucine or Isoleucine | Xle | J |
| Unspecified or unknown amino acid | Xaa | X |

As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al., Basic local alignment search tool, J. Mol. Biol., 215(3): 403-410, 1990; Altschul et al., Methods in Enzymology; Altschul et al., "Gapped BLAST and PSI-BLAST: a new generation of protein database search programs", Nucleic Acids Res. 25:3389-3402, 1997; Baxevanis et al., Bioinformatics: A Practical Guide to the Analysis of Genes and Proteins, Wiley, 1998; and Misener et al., (eds.), Bioinformatics Methods and Protocols (Methods in Molecular Biology, Vol. 132), Humana Press, 1999; all of the foregoing of which are incorporated herein by reference. In addition to identifying homologous sequences, the programs mentioned above typically provide an indication of the degree of homology. In some embodiments, two sequences are considered to be substantially homologous if at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or more of their corresponding residues are homologous over a relevant stretch of residues. In some embodiments, the relevant stretch is a complete sequence. In some embodiments, the relevant stretch is at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 225, at least 250, at least 275, at least 300, at least 325, at least 350, at least 375, at least 400, at least 425, at least 450, at least 475, at least 500 or more residues.

"Substantial identity", as used herein refers to a comparison between amino acid or nucleic acid sequences. As will be appreciated by those of ordinary skill in the art, two sequences are generally considered to be "substantially identical" if they contain identical residues in corresponding positions. As is well known in this art, amino acid or nucleic acid sequences may be compared using any of a variety of algorithms, including those available in commercial computer programs such as BLASTN for nucleotide sequences and BLASTP, gapped BLAST, and PSI-BLAST for amino acid sequences. Exemplary such programs are described in Altschul et al., Basic local alignment search tool, J. Mol. Biol., 215(3): 403-410, 1990; Altschul et al., Methods in Enzymology; Altschul et al., Nucleic Acids Res. 25:3389-3402, 1997; Baxevanis et al., Bioinformatics: A Practical Guide to the Analysis of Genes and Proteins, Wiley, 1998; and Misener, et al, (eds.), Bioinformatics Methods and Protocols (Methods in Molecular Biology, Vol. 132), Humana Press, 1999. In addition to identifying identical sequences, the programs mentioned above typically provide an indication of the degree of identity. In some embodiments, two sequences are considered to be substantially identical if at least 50%, 55%, 60%, 65%, 70%, 75%, 80%, 85%, 90%, 91%, 92%, 93%, 94%, 95%, 96%, 97%, 98%, 99% or more of their corresponding residues are identical over a relevant stretch of residues. In some embodiments, the relevant stretch is a complete sequence. In some embodiments, the relevant stretch is at least 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500 or more residues. In the context of a CDR, reference to "substantial identity" typically refers to a CDR having an amino acid sequence at least 80%, preferably at least 85%, at least 90%, at least 95%, at least 98% or at least 99% identical to that of a reference CDR.

"Surface plasmon resonance", as used herein, refers to an optical phenomenon that allows for the analysis of specific binding interactions in real-time, for example through detection of alterations in protein concentrations within a biosensor matrix, such as by using a BIAcore system (Pharmacia Biosensor AB, Uppsala, Sweden and Piscataway, N.J.). For further descriptions, see Jonsson, U., et al. (1993) Ann. Biol. Clin. 51: 19-26; Jonsson, U., et al. (1991) Biotechniques 11:620-627; Johnsson, B., et al. (1995) J. Mol. Recognit. 8: 125-131; and Johnnson, B., et al. (1991) Anal. Biochem. 198:268-277.

"Therapeutically effective amount", as used herein, is meant an amount that produces the desired effect for which it is administered. In some embodiments, the term refers to an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. In some embodiments, reference to a therapeutically effective amount may be a reference to an amount as measured in one or more specific tissues (e.g., a tissue affected by the disease, disorder or condition) or fluids (e.g., blood, saliva, serum, sweat, tears, urine, etc.). Those of ordinary skill in the art will appreciate that, in some embodiments, a therapeutically effective amount of a particular agent or therapy may be formulated and/or administered in a single dose. In some embodiments, a therapeutically effective agent may be formulated and/or administered in a plurality of doses, for example, as part of a dosing regimen.

"Transformation", as used herein, refers to any process by which exogenous DNA is introduced into a host cell. Transformation may occur under natural or artificial conditions using various methods well known in the art. Transformation may rely on any known method for the insertion of foreign nucleic acid sequences into a prokaryotic or eukaryotic host cell. In some embodiments, a particular transformation methodology is selected based on the host cell being transformed and may include, but is not limited to, viral infection, electroporation, mating, lipofection. In some embodiments, a "transformed" cell is stably transformed in that the inserted DNA is capable of replication either as an autonomously replicating plasmid or as part of the host chromosome. In some embodiments, a transformed cell transiently expresses introduced nucleic acid for limited periods of time.

"Vector", as used herein, refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., Molecular Cloning: A Laboratory Manual (2d ed., Cold Spring Harbor Laboratory Press, Cold Spring Harbor, N.Y. (1989)), which is incorporated herein by reference for any purpose.

DETAILED DESCRIPTION OF CERTAIN EMBODIMENTS

The present invention demonstrates the successful humanization of a murine antibody that binds an established melanoma associated tumor antigen. Thus, the present invention provides, among other things, humanized antibodies that bind to chondrotin sulfate proteoglycan 4 (CSPG4) or high molecular weight-melanoma associated antigen (HMW-MAA), also known as melanoma cell surface proteoglycan (MCSP) and neuron-glia protein 2 (NG2). The present invention specifically provides the first successful humanization of a murine anti-CSPG4 antibody, mouse 763.74 (referred to herein as mouse 763, m763 or 763), and furthermore provides multiple human IgG formats (e.g., IgG1 and IgG4) thereof.

Among other things, the present disclosure specifically demonstrates that humanized 763 antibodies described herein retain unusually slow $k_{off}$ rates, high affinity (e.g., nanomolar) and immunoreactivity after iodination as compared to the parental mouse 763 antibody. Further, the present disclosure specifically demonstrates that humanized 763 antibodies are highly efficient at targeting tumors in vivo. To give one specific example, the present disclosure demonstrates that unlike any other anti-CSPG4 antibodies, a specifically engineered variant glycoform of a humanized 763 antibody mediates efficient antibody-dependent cell-mediated cytotoxicity (ADCC).

The present inventors also demonstrate herein the first successful construction of a highly potent fully humanized bispecific antibody (referred to herein as hu763-BsAb) that retargets T cells to CSPG4$^+$ tumors and, therefore, is useful in cancer therapy. Furthermore, as described herein, bispecific antibodies of the present invention provide an improvement over existing bispecific antibodies that engage T cells and address a common problem in the field. Overstimulation of T cells resulting from engagement of CD3 by bispecific antibodies has been reported to contribute to the release of cytokines, which, in combination with Fc receptor binding and subsequent activation of complement, has a negative impact in patients resulting from a cytokine cascade. As described herein, bispecific antibodies of the present invention promote the release of cytokines by engaging CD3 on T cells only in the presence of tumor cells and, therefore, provide therapeutic bispecific antibodies with an improved safety profile.

Without wishing to be bound by theory, we note that data provided herein demonstrate that, in some embodiments, (e.g., where humanization of murine antibodies typically results in loss of affinity to antigen), detectable negative impact on affinity was not observed. Moreover, the present disclosure demonstrates, among other things, that humanization of murine 763 antibody as described herein did not negatively affect binding to the conformational epitope bound as compared to the parental murine antibody. The present disclosure also demonstrates, the design and construction of bispecific antibodies utilizing a specific format that combines bivalent binding to a tumor antigen and monovalent binding to T cells. We note that data provided herein demonstrate that, in some embodiments, (e.g., which includes variant Fc regions that do not bind FcRs and, therefore, do not activate complement), such a format provides efficient and potent targeting of T cells to CSPG4$^+$ tumors without adverse effects of cytokine cascade ("cytokine storm"). Thus, in at least some embodiments, the present disclosure embraces the selection of a bispecific antibody format that eliminates the possibility of over stimulating T cells and achieves enhanced tumor targeting, and humanized antibodies that retain the high affinity binding to a conformational epitope of the parental murine antibody.

Tumors

In some embodiments, any tumor that expresses CSPG4 can be considered a CSPG4$^+$ tumors. In some embodiments, a CSPG4+ tumor may arise from any tissue type. In some embodiments, a CSPG4+ tumor may be a solid tumor. In some embodiments, a CSPG4+ tumor may include or comprise a soft tissue sarcoma, cerebral tumor, bone tumor, breast carcinoma, squamous cell carcinoma, pancreatic tumor, stomach tumor, melanoma and/or mesothelioma. In some embodiments, a CSPG4$^+$ tumor may include or comprise a fibrosarcoma, leiomyosarcoma, pleomorphic sarcoma, liposarcoma, synovial sarcoma, chondrosarcoma, glioblastoma, chordoma, lobular breast carcinoma, TNBC breast carcinoma, ER+ breast carcinoma, HER2+ breast carcinoma, ductal breast carcinoma, oral cavity squamous cell carcinoma, pancreatic cystademona, pancreatic intraductal papillary mucinous neoplasm, pancreatic ductal malignancy, uveal melanoma, NS melanoma, acral lentiginous melanoma, nodular melanoma, superficial spreading melanoma, conjunctival melanoma, desmoplastic melanoma, sacromatoid mesotheliaoma, epithelioid mesothelioma, biphasic mesothelioma, osteosarcoma, head and neck cancer, glioblastoma multiforme, sarcoma, adenocarcinoma, or colorectal adenocarcinoma. In some embodiments, a CSPG4+ tumor is a melanoma, osteosarcoma, head and neck tumor, glioblastoma multiforme, sarcoma and/or mesothelioma.

Melanoma

The incidence of melanoma worldwide is rising rapidly with an annual increase by 3-7%. In the United States, the incidence almost tripled among males and more than doubled among females between 1973 and 1997, affecting approximately 22 per 100,000 males and 14 for 100,000 females. This translates to approximately 59,580 new diagnoses and 7770 deaths from melanoma in 2005 alone, according to the American Cancer Society. In the early stages of melanoma, surgery represents a potential curative modality. However, in nonresectable stage III or IV malignant melanoma, the prognosis remains very poor. The median survival of stage IV disease is approximately 6-10 months with only about 4-6% surviving to 5 years. As of 2010, less than 5 years ago, systemic chemotherapy is the mainstay of treatment, but it is generally considered palliative rather than curative. Until recently, few therapeutic agents have produced response rates>20%. In meta-analyses, the response to dacarbazine monotherapy ranged between 5.3% and 28.0% (with an average of 15.3%). Biochemotherapy, where high dose chemotherapy was combined with interferon or interleukin-2 (IL-2), did not improve survival. In the previous decade, of the seven completed randomized phase III adjuvant melanoma vaccine trials using self-antigens, none have shown a benefit. Induced cytotoxic T lymphocytes (CTLs) typically fail to home to the site(s) of a tumor. Moreover, since these target antigens are non-essential for melanoma, tumor escape following single target vaccine is expected.

Two recent developments have begun to change the prognosis of high-risk melanoma, namely, small molecule inhibitors (e.g. BRAF inhibitors) and immune checkpoints manipulations (e.g. anti-CTLA4, anti-PD-L1, anti-PD1). Both human anti-CTLA-4 IgG1 monoclonal antibodies ipilimumab and tremelimumab have generated durable clinical responses in melanoma and other cancers, accompanied in some by autoimmune side effects. Adoptive T-cell therapy has also received much attention recently, and when combined with myeloablative therapy has produced unusually high response rates. These human experiments have repeatedly shown the potential for T cells in controlling and/or ameliorating melanoma.

Monoclonal antibodies can induce cell death, promote blockade of signaling pathways, induce antibody dependent cellular cytotoxicity (ADCC) and complement dependent cytotoxicity (CDC). Several antibodies (R24, 9.2.27, 3F8 and CE7) have been successfully tested in the clinic against melanoma targeting GD3 (Houghton, A. N. et al. (1985) Proc. Natl. Acad. Sci. U.S.A. 82:1242-1246), HMW-MAA (or CSPG4; Raja, C. et al. (2007) Cancer Biol. Ther. 6:846-852), GD2 (Cheung, N. K. et al. (1987) Oncol. 5:1430-1440) and L1CAM (Meier, F. et al. (2006) Int. J. Cancer 119:549-555; Novak-Hofer, I. (2007) Cancer Biother. Radiopharm. 22:175-184), respectively.

Chondroitin Sulfate Proteoglycan 4

Chondroitin sulfate proteoglycan 4 (CSPG4, also known as HMW-MAA, MCSP, MCSPG, MEL-CSPG, MSK16, NG2) is a 250 kD glycoprotein that is expressed at high levels and in >85% of melanomas (Kantor, R. R. et al. (1982) Hybridoma 1:473-482), 70% of gliomas, 50% of chondromas and chondrosarcomas, 55% of acute lymphocytic leukemias (ALL), 100% of mesotheliomas (Rivera, Z. et al. (2012) Clin. Cancer Res. 18:5352-5363), 77% of invasive ductal breast carcinomas, 50% of head and neck squamous cell carcinomas (HNSCC), glioblastomas, clear cell renal carcinomas, neuroblastomas and sarcomas (Geldres, C. et al. (2014) Clin. Cancer Res. 20:962-971). Exemplary amino acid sequences of mouse and human CSPG4 are presented below (signal peptides are italicized).

Human CSPG4 (NP_001888)

(SEQ ID NO: 1)

MQSGPRPPLPAPGLALALTLTMLARLASAASFFGENHLEVPVATALTDID

LQLQFSTSQPEALLLLAAGPADHLLLQLYSGRLQVRLVLGQEELRLQTPA

ETLLSDSIPHTVVLTVVEGWATLSVDGFLNASSAVPGAPLEVPYGLFVGG

TGTLGLPYLRGTSRPLRGCLHAATLNGRSLLRPLTPDVHEGCAEEFSASD

DVALGFSGPHSLAAFPAWGTQDEGTLEFTLTTQSRQAPLAFQAGGRRGDF

IYVDIFEGHLRAVVEKGQGTVLLHNSVPVADGQPHEVSVHINAHRLEISV

DQYPTHTSNRGVLSYLEPRGSLLLGGLDAEASRHLQEHRLGLTPEATNAS

LLGCMEDLSVNGQRRGLREALLTRNMAAGCRLEEEEYEDDAYGHYEAFST

LAPEAWPAMELPEPCVPEPGLPPVFANFTQLLTISPLVVAEGGTAWLEWR

HVQPTLDLMEAELRKSQVLFSVTRGARHGELELDIPGAQARKMFTLLDVV

NRKARFIHDGSEDTSDQLVLEVSVTARVPMPSCLRRGQTYLLPIQVNPVN

DPPHIIFPHGSLMVILEHTQKPLGPEVFQAYDPDSACEGLTFQVLGTSSG

LPVERRDQPGEPATEFSCRELEAGSLVYVHRGGPAQDLTFRVSDGLQASP

PATLKVVAIRPAIQIHRSTGLRLAQGSAMPILPANLSVETNAVGQDVSVL

FRVTGALQFGELQKQGAGGVEGAEWWATQAFHQRDVEQGRVRYLSTDPQH

HAYDTVENLALEVQVGQEILSNLSFPVTIQRATVWMLRLEPLHTQNTQQE

TLTTAHLEATLEEAGPSPPTFHYEVVQAPRKGNLQLQGTRLSDGQGFTQD

DIQAGRVTYGATARASEAVEDTFRFRVTAPPYFSPLYTFPIHIGGDPDAP

VLTNVLLVVPEGGEGVLSADHLFVKSLNSASYLYEVMERPRHGRLAWRGT

QDKTTMVTSFTNEDLLRGRLVYQHDDSETTEDDIPFVATRQGESSGDMAW

EEVRGVFRVAIQPVNDHAPVQTISRIFHVARGGRRLLTTDDVAFSDADSG

FADAQLVLTRKDLLFGSIVAVDEPTRPIYRFTQEDLRKRRVLFVHSGADR

GWIQLQVSDGQHQATALLEVQASEPYLRVANGSSLVVPQGGQGTIDTAVL

HLDTNLDIRSGDEVHYHVTAGPRWGQLVRAGQPATAFSQQDLLDGAVLYS

HNGSLSPRDTMAFSVEAGPVHTDATLQVTIALEGPLAPLKLVRHKKIYVF

QGEAAEIRRDQLEAAQEAVPPADIVFSVKSPPSAGYLVMVSRGALADEPP

SLDPVQSFSQEAVDTGRVLYLHSRPEAWSDAFSLDVASGLGAPLEGVLVE

LEVLPAAIPLEAQNFSVPEGGSLTLAPPLLRVSGPYFPTLLGLSLQVLEP

PQHGALQKEDGPQARTLSAFSWRMVEEQLIRYVHDGSETLTDSFVLMANA

SEMDRQSHPVAFTVTVLPVNDQPPILTTNTGLQMWEGATAPIPAEALRST

DGDSGSEDLVYTIEQPSNGRVVLRGAPGTEVRSFTQAQLDGGLVLFSHRG

TLDGGFRFRLSDGEHTSPGHFFRVTAQKQVLLSLKGSQTLTVCPGSVQPL

SSQTLRASSSAGTDPQLLLYRVVRGPQLGRLFHAQQDSTGEALVNFTQAE

VYAGNILYEHEMPPEPFWEAHDTLELQLSSPPARDVAATLAVAVSFEAAC

PQRPSHLWKNKGLWVPEGQRARITVAALDASNLLASVPSPQRSEHDVLFQ

VTQFPSRGQLLVSEEPLHAGQPHFLQSQLAAGQLVYAHGGGGTQQDGFHF

RAHLQGPAGASVAGPQTSEAFAITVRDVNERPPQPQASVPLRLTRGSRAP

ISRAQLSVVDPDSAPGEIEYEVQRAPHNGFLSLVGGGLGPVTRFTQADVD

SGRLAFVANGSSVAGIFQLSMSDGASPPLPMSLAVDILPSAIEVQLRAPL

EVPQALGRSSLSQQQLRVVSDREEPEAAYRLIQGPQYGHLLVGGRPTSAF

-continued

SQFQIDQGEVVFAFTNFSSSHDHFRVLALARGVNASAVVNVTVRALLHVW

AGGPWPQGATLRLDPTVLDAGELANRTGSVPRFRLLEGPRHGRVVRVPRA

RTEPGGSQLVEQFTQQDLEDGRLGLEVGRPEGRAPGPAGDSLTLELWAQG

VPPAVASLDFATEPYNAARPYSVALLSVPEAARTEAGKPESSTPTGEPGP

MASSPEPAVAKGGFLSFLEANMFSVIIPMCLVLLLLALILPLLFYLRKRN

KTGKHDVQVLTAKPRNGLAGDTETFRKVEPGQAIPLTAVPGQGPPPGGQP

DPELLQFCRTPNPALKNGQYWV

Mouse CSPG4 (NP_620570)
(SEQ ID NO: 2)
MLLGPGHPLSAPALALALTLALLVRSTAPASFFGENHLEVPVPSALTRVD

LLLQFSTSQPEALLLLAAGQDDHLLLQLHSGCLQVRLALGQKELKLQTPA

DTVLSDSAPHTVVLTVSDSWAVLSVDGVLNTSAPIPRASHLKATYGLFVG

SSGSLDLPYLKGISRPLRGCLHSAILNGRNLLRPLTSDVHEGCAEEFSAG

DEVGLGFSGPHSLAAFPAWSTREEGTLEFTLTTRSQQAPLAFQAGDKRGN

FIYVDIFEGHLRAVVEKGQGTMLLRNSVPVADGQPHEVSVHIDVHRLEIS

VDQYPTRTFNRGVLSYLEPRGSLLLGGLDTEASRHLQEHRLGLAPGAANI

SLVGCIEDFSVNGRRQGLRDAWLTRDMSAGCRPEEDEYEEEVYGPYETFS

TLAPEAWPAMELPEPCIPEPGLPAVFANFTQLLTISPLVVAEGGTAWLEW

RHVQPTLDLTEAELRKSQVLFSVSQSARHGDLELDILGAQTRKMFTLLDV

VNRKARFVHDGSEDTSDQLMLEVSVTARAPVPSCLRRGQIYILPIQVNPV

NDPPRIIFPHGSLMVILEHTQKPLGPEIFQAYDPDSACEGLTFQLLGVSS

GVPVEHRDQPGEPATEFSCRELEVGDIVYVHRGGPAQDLTFRVSDGMQAS

APATLKVVAVRPAIQILHNTGLHLAQGSAAAILPANLSVETNAVGQDVSV

LFRVTGTLQFGELQKQGAGGVEGTEWWDTLAFHQRDVEQGRVRYLSTDPQ

HHTQDTVEDLILEVQVGQETLSNLSFPVTIQRATVWMLRLEPLHTQNPHQ

ETLTPAHLEASLEEEEEGSPQPHTFHYELVQAPRRGNLLLQGTRLSDGE

SFSQSDLQAGRVTYRATMRTSEAADDSFRFRVTSPPHFSPLYTFPIHIGG

DPNAPVLTNVLLMVPEGGEGVLSADHLFVKSLNSASYLYEVMEQPHHGKL

AWRDPKGKSTPVTSFTNEDLLHGRLVYQHDDSETIEDDIPFVATRQGEGS

GDMAWEEVRGVFRVAIQPVNDHAPVQTISRVFHVARGGQRLLTTDDVAFS

DADSGFSDAQLVLTRKDLLFGSIVAMEEPTRPIYRFTQEDLRKKQVLFVH

SGADHGWLQLQVSDGQHQATAMLEVQASEPYLHVANSSSLVVPQGGQGTI

DTAVLQLDTNLDIRSGNEVHYHVTAGPQWGQLLRDGQSVTSFSQRDLLDG

AILYSHNGSLSPQDTLAFSVAAGPVHTNTFLQVTIALEGPLAPLQLVQHK

KIYVFQGEAAEIRRDQLEVVQEAVLPADIMFSLRSPPNAGYLVMVSHGAS

AEEPPSLDPVQSFSQEAVNSGRVLYLHSRPGAWSDSFSLDVASGLGDPLE

GISVELEVLPTVIPLDVQNFSVPEGGTRTLAPPLVQITGPYFPTLPGLVL

QVLEPPQHGALQKEDHSQDGSLSTFSWREVEEQLIRYVHDGSETQTDAFV

LLANASEMDRQSQPVAFTITILPVNDQPPVLTTNTGLQIWEGAIVPIPPE

ALRGTDNDSGPEDLVYTIEQPSNGRIALRVAPDTEVHRFTQAQLDSGLVL

FSHRGALEGGFHFDLSDGAHTSPGHFFRVVAQKQALLSLEGTRKLTVCPE

SVQPLSSQSLSASSSTGADPRHLLYRVVRGPQLGRLLHAQQGSAEEVLVN

FTQAEVNAGNILYEHEMSSEPFWEAHDTIGLLLSSPPARDLAATLAVMVS

FDAACPQRPSRLWKNKGLWVPEGQRAKITVAALDAANLLASVPASQRSRH

DVLFQVTQFPTRGQLLVSEEPLHARRPYFLQSELAAGQLVYAHGGGGTQQ

DGFRFRAHLQGPTGTSVAGPQTSEAFVITVRDVNERPPQPQASIPLRVTR

GSRAPVSRAQLSVVDPDSAPGEIEYEVQRAPHNGFLSLAGDNTGPVTHFT

QADVDAGRLAFVANGSSVAGVFQLSMSDGASPPIPMSLAVDVLPSTIEVQ

LRAPLEVPQALGRTSLSRQQLQVISDREEPDVAYRLTQGPLYGQLLVGGQ

PASAFSQLQVDQGDVVFVFTNFSSSQDHFKVVALARGVNASATVNVTVQA

LLHVWAGGPWPQGTTLRLDPTVLDASELANRTGSMPHFRLLAGPRYGRVV

RVSQGRTESRSNQLVEHFTQRDLEEGQLGLEVGKPEGRSTGPAGDRLTLE

LWAKGVPPAVALLDFATEPYHAAKSYSVALLSVPEAVRTETEKPGRSVPT

GQPGQAASSPVPTAAKGGFLGFLEANMFSIIIPVCLILLLLALILPLLFY

LRKRNKTGKHDVQVLTAKPRNGLAGDTETFRKVEPGQAIPLITVPGQGPP

PGGQPDPELLQFCRTPNPALRNGQYWV

The biology of CSPG4 protein has been extensively annotated. CSPG4 has been reported to inhibit neurite outgrowth and growth cone collapse during axon regeneration (Bradbury, E. J. et al. (2002) Nature 416:636-640). As cell surface receptor for collagen alpha 2(VI), CSPG4 confers cells the ability to migrate on that substrate. CSPG4 binds through its extracellular N-terminus growth factors, extracellular matrix proteases modulating their activity (Stallcup, W. B. et al. (2008) Cell Adh. Migr. 2:192-201). CSPG4 also regulates MPP16-dependent degradation and invasion of type I collagen participating in melanoma cells invasion properties (Iida, J. et al. (2001) J. Biol. Chem. 276:18786-18794). CSPG4 has been reported to modulate the plasminogen system by enhancing plasminogen activation and inhibiting angiostatin (Kirsch, M. et al. (2004) Cancer Treat. Res. 117:285-304). Further, CSPG4 has been reported to function as a signal transducing protein by binding through its cytoplasmic C-terminus scaffolding and signaling proteins (Barritt, D. S. et al. (2000) J. Cell Biochem. 79:213-224; Stegmuller, J. et al. (2002) J. Neurocytol. 31:497-505; Chatterjee, N. et al. (2008) J. Biol. Chem. 283:8310-8317). CSPG4 also promotes retraction fiber formation and cell polarization through Rho GTPase activation (Campoli, M. R. et al. (2004) Crit. Rev. Immunol. 24:267-296) and stimulates alpha-4, beta-1 integrin-mediated adhesion and spreading by recruiting and activating a signaling cascade through CDC42, ACK1 and BCAR1.17 (Eisenmann, K. M. et al. (1999) Nat. Cell Biol. 1:507-513). Still others have reported that CSPG4 activates FAK and ERKVERK2 signaling cascades (Yang, J. et al. (2004) J. Cell Biol. 165:881-891).

CSPG4 is an adhesion and migration protein on melanoma and tumor activated pericytes, highly conserved throughout evolution, and highly restricted in normal tissues. CSPG4 is expressed by basal breast cancer cell lines, but not by luminal breast cancer cell lines. CSPG4 was reported to be expressed in 73% of primary triple negative breast cancer tumors and cell lines as indicated by an anti-CSPG4 antibody (mAb 225.228), which inhibited tumor growth and metastasis in vitro and in vivo (Wang, X. et al. (2010) J. Natl. Cancer Inst. 102:1496-1512). CSPG4 was found in 57% of canine malignant melanoma (Mayayo, S. L. et al. (2011) Vet. J. 190:e26-30), and a recent vaccine trial significantly prolonged overall and disease-free survival times (Riccardo, F. et al. (2014) Clin. Cancer Res. 20:3753-3762). The first antibody against human HMW-MAA (CSPG4) described was 9.2.27, which is a mouse IgG2a antibody. Up to 200 mg were infused into humans without major side effects other than fever (Oldham, R. K. et al. (1984) J. Clin. Oncol. 2:1235-1244). Subsequent studies were mainly focused in radioimaging and radioimmunotherapy where the 9.2.27 antibody was conjugated to an alpha-emitter (Del Vecchio, S. et al. (1989) Cancer Res. 49:2783-2789). Among 22 patients with stage IV/in-transit metastatic melanoma treated with intravenous $^{213}$Bi-9.2.27 (1.5-25.8 mCi; Raja, C. et al. (2007) Cancer Biol. Ther. 6:846-852), 14% had PR and 50% SD, and toxicity was negligible. Antibody 9.2.27 has also been used successfully as immunotoxin (Godal, A. et al. (1992) Int. J. Cancer 52:631-635) and for detecting osteosarcoma micrometastases (Bruland, O. S. et al. (2005) Clin. Cancer Res. 11:4666-4673). The mouse anti-CSPG4 antibody 763.74 was first described in the 1980's (Natali, P. G. et al. (1989) Cancer Res. 49:1269-1274) and shown to react with both cutaneous and uveal melanoma. The epitope of the mouse 763.74 antibody was mapped by phage display to an amino acid sequence (Luo, W. et al. (2005) J. Immunol. 174:7104-7110). An anti-idiotypic antibody to 763 has been used as a vaccine in clinic trials (Mittelman, A. et al. (1995) Clin. Cancer Res. 1:705-713). Mouse 763 antibody has been reported to significantly inhibit both basal breast tumor experimental and post-surgical lung metastases, and local tumor recurrence in mouse xenografts in mice (Wang, X. et al., supra). A chimeric antigen receptor (CAR) using an scFv constructed from the mouse 763 antibody has also been described (Reinhold, U. et al. (1999) J. Investig. Dermatol. 112:744-750). CSPG4-CAR modified T cells (derived from antibodies 225.28 or 763) have demonstrated the ability to control tumor growth in vitro and in vivo in NSG mice xenografted with human melanoma, head and neck squamous cell carcinoma (HNSCC) and breast carcinoma (Geldres, C. et al., supra; Burns, W. R. et al. (2010) Cancer Res. 70:3027-3033). A human scFv derived from a phage library (scFv-FcC21) was recently described and engineered as an scFv-Fc form showing activity in vitro and in vivo against melanoma (Wang, X. et al. (2011) Cancer Res. 71:7410-7422). An anti-CSPG4×anti-CD3 bispecific T-cell engager (BiTE) antibody has reportedly been developed (Bluemel, C. et al. (2010) Cancer Immunol. Immunother. 59:1197-1209; Torisu-Itakura, H. et al. (2011) J. Immunother. 34:597-605), however, the clinical status of this therapeutic is unknown. Currently, no bispecific antibodies derived from mouse 763.74 has been successfully developed.

As described herein, the inventors have developed humanized anti-CSPG4 antibodies based on mouse 763.74 (herein referred to as mouse 763 or m763). Twelve (12) particular such humanized anti-CSPG4 antibodies are explicitly exemplified herein. Without wishing to be bound by any particular theory, the inventors have developed humanized anti-CSPG4 antibodies provided herein on the insight that mouse 763 binds a peptide epitope (not a carbohydrate epitope) with high affinity (as described in the Examples section below), and has similar staining patterns in normal and melanoma tissue as compared to other anti-CSPG4 antibodies (see Tables 3 and 4; neg: negative, 1:positive+, 2:positive++, 3:positive+++). Among the various heavy and light chain humanized sequences generated and described herein, one $V_H$ and one $V_L$ sequence was chosen based on antigen affinity and stability in vitro. Three humanized antibody formats were successfully engineered (hu763-IgG1, hu763-IgG4 and hu763-IgG1n [a special glycoform]). We note that data provided herein demonstrate that the humanized antibodies demonstrated antigen binding comparable to mouse 763, in particular, humanized 763 antibodies demonstrated slow $k_{off}$ rates and highly favorable $K_D$s. Further, we note that unlike any of the published anti-CSPG4 antibodies or fusion proteins, humanized 763 antibodies provided herein mediate highly efficient antibody-dependent cell-mediated cytotoxicity (ADCC) against melanoma cells (e.g., hu763-IgG1n).

The present invention further provides bispecific antibodies based on humanized 763 antibody sequences, in particular, bispecific antibodies that redirect T cells to target CSPG4 on the surface of melanoma cells. To give two specific examples, the present disclosure demonstrates the successful linkage of an anti-CD3 antibody component (e.g., a humanized OKT3 scFv) to the carboxyl end of a humanized 763 heavy chain to create an anti-CSPG4×anti-CD3 bispecific antibody referred to herein as hu763-HC-OKT3 or to the carboxyl end of a humanized 763 light chain to create an anti-CSPG4×anti-CD3 bispecific antibody referred to herein as hu763-LC-OKT3. Further modifications to bispecific antibodies were made to engineer additional effector functions. For example, an N297A mutation introduced into the Fc region thereby eliminating glycosylation. This elimination of glycosylation lead to a reduced complement activation due to abolishing Fc-receptor binding, which avoids nonspecific cytokine storm that has been reported to accompany engagement of T cells. We note that data provided herein specifically demonstrates that humanized anti-CSPG4×anti-CD3 bispecific antibodies effectively activate T cells and directed T cells to lyse human tumor cell lines in vitro. Moreover, bispecific antibodies provided herein significantly inhibited tumor growth in murine melanoma xenograft models. The data provided herein confirms that humanized mono- and bispecific antibodies described herein represent cancer therapeutics characterized by improved efficacy and safety profiles.

TABLE 3

Comparison of anti-CSPG4 antibodies IHC on normal human tissues

| Name | MOPC21 (2 µg/mL) | 225.28 (1 µg/mL) | D2.8.5-C4B8 (1 µg/mL) | 9.2.2.7 (1 µg/mL) | m763 (1 µg/mL) |
|---|---|---|---|---|---|
| Cerebellum | neg | neg | neg | neg | neg |
| Frontal Lobe | neg | neg | neg | neg | neg |
| Pons | neg | neg | neg | neg | neg |
| Spinal Cord | neg | neg | neg | neg | neg |
| Muscle | neg | neg | neg | neg | neg |
| Skeletal | neg | neg | neg | neg | neg |
| Pancreas | neg | neg | neg | neg | neg |
| Liver | neg | neg | neg | neg | neg |
| Lung | neg | neg | neg | neg | neg |
| Spleen | neg | neg | neg | neg | neg |
| Thyroid | neg | neg | neg | neg | neg |
| Kidney | neg | neg | neg | neg | neg |
| Testes | neg | neg | neg | neg | neg |
| Adrenal | neg | neg | neg | neg | neg |
| Ileum | neg | 2 | 1 | 2 | 2 |
| Sigmoid Colon | neg | 2 | 1 | 2 | 2 |
| Stomach | neg | 1 | 1 | 1 | 1 |

TABLE 4

Comparison of anti-CSPG4 antibodies IHC on human melanoma tissues

| Melanoma Sample # | MOPC21 (2 µg/mL) | 225.28 (1 µg/mL) | D2.8.5-C4B8 (1 µg/mL) | 9.2.2.7 (1 µg/mL) | m763 (1 µg/mL) |
|---|---|---|---|---|---|
| 619 | neg | neg | neg | neg | neg |
| 1926 | neg | neg | neg | neg | neg |
| 2665 | neg | neg | neg | neg | neg |
| 2673 | neg | neg | neg | neg | neg |
| 524 | neg | 1 | neg to 1 | neg to 1 | 1 |
| 2003 | neg | 1 | neg to 1 | 1 | 1 |
| 2664 | neg | 1 | neg to 1 | 1 | 1 |
| 319 | neg | 3 | 2 | >2 | 3 |
| 508 | neg | 3 | 3 | 3 | 3 |
| 2655 | neg | 3 | 3 | 3 | 3 |
| 2657 | neg | 3 | 3 | 3 | 3 |
| 2658 | neg | 3 | 3 | 3 | 3 |
| 2659 | neg | 2 | 1 | 2 | 2 |
| 2667 | neg | 3 | 2 | 3 | 3 |
| 2668 | neg | 3 | 3 | 3 | 3 |
| 2669 | neg | 3 | 3 | 3 | 3 |
| 2671 | neg | 3 | 3 | 3 | 3 |
| 2715 | neg | 3 | 3 | 3 | 3 |
| 2716 | neg | 3 | 3 | 3 | 3 |

Exemplary humanized and chimeric CSPG4 antibodies of the present invention are presented in Table 5. Ch: chimeric; Hu: humanized; HC: heavy chain; LC: light chain.

TABLE 5 ch763 HC cDNA

```
CAGATCCAGTTGGTGCAGTCTGGACCTGAGCTGAAGAAGC
CTGGAGAGACAGTCAAGATCTCCTGCAAGGCTTCTGGTTAT
ACCTTCACAGACTATTCAATGCACTGGGTGAAGAAGACTCC
AGGAAAGGGTTTAAAGTGGCTGGGCTGGATAAACACTGCG
ACTGGTGAGCCAACATATGCAGATGACTTCAAGGGACGGT
TTGCCATCTCTTTGGAAACCTCTGCCAGGACTGTCTATTTGC
AGATCAATAATCTCAGAAATGAGGACACGGCTACATATTTC
TGTTTTAGTTACTACGACTACTGGGGCCAAGGCACCACTCT
CACAGTTTCCGCCTCCACCAAGGGCCCATCGGTCTTCCCCC
TGGCACCCTCCTCCAAGAGCACCTCTGGGGGCACAGCGGCC
CTGGGCTGCCTGGTCAAGGACTACTTCCCCGAACCGGTGAC
GGTGTCGTGGAACTCAGGCGCCCTGACCAGCGGCGTGCAC
ACCTTCCCGGCCGTCCTACAGTCCTCAGGACTCTACTCCCTC
AGCAGCGTGGTGACCGTGCCCTCCAGCAGCTTGGGCACCCA
GACCTACATCTGCAACGTGAATCACAAGCCCAGCAACACC
AAGGTGGACAAGAGAGTTGAGCCCAAATCTTGTGACAAAA
CTCACACATGCCCACCGTGCCCAGCACCTGAACTCCTGGGG
GGACCGTCAGTCTTCCTCTTCCCCCCAAAACCCAAGGACAC
CCTCATGATCTCCCGGACCCCTGAGGTCACATGCGTGGTGG
TGGACGTGAGCCACGAAGACCCTGAGGTCAAGTTCAACTG
GTACGTGGACGGCGTGGAGGTGCATAATGCCAAGACAAAG
CCGCGGGAGGAGCAGTACAACAGCACGTACCGTGTGGTCA
GCGTCCTCACCGTCCTGCACCAGGACTGGCTGAATGGCAAG
GAGTACAAGTGCAAGGTCTCCAACAAAGCCCTCCCAGCCC
CCATCGAGAAAACCATCTCCAAAGCCAAAGGGCAGCCCCG
AGAACCACAGGTGTACACCCTGCCCCCATCCCGGGATGAG
CTGACCAAGAACCAGGTCAGCCTGACCTGCCTGGTCAAAG
GCTTCTATCCCAGCGACATCGCCGTGGAGTGGGAGAGCAAT
GGGCAGCCGGAGAACAACTACAAGACCACGCCTCCCGTGC
TGGACTCCGACGGCTCCTTCTTCCTCTACAGCAAGCTCACC
GTGGACAAGAGCAGGTGGCAGCAGGGGAACGTCTTCTCAT
GCTCCGTGATGCATGAGGCTCTGCACAACCACTACACGCAG
AAGAGCCTCTCCCTGTCTCCGGGTAAATGA (SEQ ID NO: 3)
``` ch763 HC amino acid

```
QIQLVQSGPELKKPGETVKISCKASGYTFTDYSMHWVKKTPG
KGLKWLGWINTATGEPTYADDFKGRFAISLETSARTVYLQIN
NLRNEDTATYFCFSYYDYWGQGTTLTVSASTKGPSVFPLAPSS
KSTSGGTAALGCLVKDYFPEPVTVSWNSGALTSGVHTFPAVL
QSSGLYSLSSVVTVPSSSLGTQTYICNVNHKPSNTKVDKRVEP
KSCDKTHTCPPCPAPELLGGPSVFLFPPKPKDTLMISRTPEVTC
VVVDVSHEDPEVKFNWYVDGVEVHNAKTKPREEQYNSTYRV
VSVLTVLHQDWLNGKEYKCKVSNKALPAPIEKTISKAKGQPR
EPQVYTLPPSRDELTKNQVSLTCLVKGFYPSDIAVEWESNGQP
ENNYKTTPPVLDSDGSFFLYSKLTVDKSRWQQGNVFSCSVMH
EALHNHYTQKSLSLSPGK (SEQ ID NO: 4)
``` ch763 LC cDNA

```
GACATCAAGCTGTCCCAGTCCCCCTCCATCCTGTCCGTGAC
CCCCGGCGAGACCGTGTCCCTGTCCTGCCGGGCCTCCCAGA
CCATCTACAAGAACCTGCACTGGTACCAGCAGAAGTCCCAC
CGGTCCCCCCGGCTGCTGATCAAGTACGGCTCCGACTCCAT
CTCCGGCATCCCCTCCCGGTTCACCGGCTCCGGCTCCGGCA
CCGACTACACCCTGAACATCAACTCCGTGAAGCCCGAGGA
CGAGGGCATCTACTACTGCCTGCAGGGCTACTCCACCCCCT
GGACCTTCGGCGGCGGCACCAAGCTGGAGATCAAGCGGAC
CGTGGCCGCCCCCTCCGTGTTCATCTTCCCCCCCTCCGACGA
GCAGCTGAAGTCCGGCACCGCCTCCGTGGTGTGCCTGCTGA
ACAACTTCTACCCCCGGGAGGCCAAGGTGCAGTGGAAGGT
```

TABLE 5-continued

| | |
|---|---|
| | GGACAACGCCCTGCAGTCCGGCAACTCCCAGGAGTCCGTG<br>ACCGAGCAGGACTCCAAGGACTCCACCTACTCCCTGTCCTC<br>CACCCTGACCCTGTCCAAGGCCGACTACGAGAAGCACAAG<br>GTGTACGCCTGCGAGGTGACCCACCAGGGCCTGTCCTCCCC<br>CGTGACCAAGTCCTTCAACCGGGGCGAGTGCTAG<br>(SEQ ID NO: 5) |
| ch763 LC amino acid | DIKLSQSPSILSVTPGETVSLSCRASQTIYKNLHWYQQKSHRSP<br>RLLIKYGSDSISGIPSRFTGSGSGTDYTLNINSVKPEDEGIYYCL<br>QGYSTPWTFGGGTKLEIKRTVAAPSVFIFPPSDEQLKSGTASV<br>VCLLNNFYPREAKVQWKVDNALQSGNSQESVTEQDSKDSTY<br>SLSSTLTLSKADYEKHKVYACEVTHQGLSSPVTKSFNRGEC<br>(SEQ ID NO: 6) |
| hu763 H1 IgG1 cDNA | CAGATCCAGCTGGTGCAGTCCGGCCCCGAGGTGAAGAAGC<br>CCGGCGCCTCCGTGAAGATCTCCTGCAAGGCCTCCGGCTAC<br>ACCTTCACCGACTACTCCATGCACTGGGTGAAGAAGGCCCC<br>CGGCCAGGGCCTGGAGTGGCTGGGCTGGATCAACACCGCC<br>ACCGGCGAGCCCACCTACGCCGACGACTTCAAGGGCCGGT<br>TCACCATCACCCTGGACACCTCCGCCCGGACCGTGTACCTG<br>CAGATCAACAACCTGCGGTCCGAGGACACCGCCACCTACTT<br>CTGCTTCTCCTACTACGACTACTGGGGCCAGGGCACCCTGC<br>TGACCGTGTCCTCCGCCTCCACCAAGGGCCCATCGGTCTTC<br>CCCCTGGCACCCTCCTCCAAGAGCACCTCTGGGGGCACAGC<br>GGCCCTGGGCTGCCTGGTCAAGGACTACTTCCCCGAACCGG<br>TGACGGTGTCGTGGAACTCAGGCGCCCTGACCAGCGGCGT<br>GCACACCTTCCCGGCCGTCCTACAGTCCTCAGGACTCTACT<br>CCCTCAGCAGCGTGGTGACCGTGCCCTCCAGCAGCTTGGGC<br>ACCCAGACCTACATCTGCAACGTGAATCACAAGCCCAGCA<br>ACACCAAGGTGGACAAGAGAGTTGAGCCCAAATCTTGTGA<br>CAAAACTCACACATGCCCACCGTGCCCAGCACCTGAACTCC<br>TGGGGGGACCGTCAGTCTTCCTCTTCCCCCCAAAACCCAAG<br>GACACCCTCATGATCTCCCGGACCCCTGAGGTCACATGCGT<br>GGTGGTGGACGTGAGCCACGAAGACCCTGAGGTCAAGTTC<br>AACTGGTACGTGGACGGCGTGGAGGTGCATAATGCCAAGA<br>CAAAGCCGCGGGAGGAGCAGTACAACAGCACGTACCGTGT<br>GGTCAGCGTCCTCACCGTCCTGCACCAGGACTGGCTGAATG<br>GCAAGGAGTACAAGTGCAAGGTCTCCAACAAAGCCCTCCC<br>AGCCCCCATCGAGAAAACCATCTCCAAAGCCAAAGGGCAG<br>CCCCGAGAACCACAGGTGTACACCCTGCCCCCATCCCGGGA<br>TGAGCTGACCAAGAACCAGGTCAGCCTGACCTGCCTGGTCA<br>AAGGCTTCTATCCCAGCGACATCGCCGTGGAGTGGGAGAG<br>CAATGGGCAGCCGGAGAACAACTACAAGACCACGCCTCCC<br>GTGCTGGACTCCGACGGCTCCTTCTTCCTCTACAGCAAGCT<br>CACCGTGGACAAGAGCAGGTGGCAGCAGGGGAACGTCTTC<br>TCATGCTCCGTGATGCATGAGGCTCTGCACAACCACTACAC<br>GCAGAAGAGCCTCTCCCTGTCTCCGGGTAAATGA<br>(SEQ ID NO: 7) |
| hu763 H1 IgG1 amino acid | QIQLVQSGPEVKKPGASVKISCKASGYTFTDYSMHWVKKAPG<br>QGLEWLGWINTATGEPTYADDFKGRFTITLDTSARTVYLQINN<br>LRSEDTATYFCFSYYDYWGQGTLLTVSSASTKGPSVFPLAPSS<br>KSTSGGTAALGCLVKDYFPEPVTVSWNSGALTSGVHTFPAVL<br>QSSGLYSLSSVVTVPSSSLGTQTYICNVNHKPSNTKVDKRVEP<br>KSCDKTHTCPPCPAPELLGGPSVFLFPPKPKDTLMISRTPEVTC<br>VVVDVSHEDPEVKFNWYVDGVEVHNAKTKPREEQYNSTYRV<br>VSVLTVLHQDWLNGKEYKCKVSNKALPAPIEKTISKAKGQPR<br>EPQVYTLPPSRDELTKNQVSLTCLVKGFYPSDIAVEWESNGQP<br>ENNYKTTPPVLDSDGSFFLYSKLTVDKSRWQQGNVFSCSVMH<br>EALHNHYTQKSLSLSPGK (SEQ ID NO: 8) |
| hu763 H2 IgG1 cDNA | CAGGTGCAGCTGGTGCAGTCCGGCCCCGAGGTGAAGAAGC<br>CCGGCGCCTCCGTGAAGATCTCCTGCAAGGCCTCCGGCTAC<br>ACCTTCACCGACTACTCCATGCACTGGGTGAAGAAGGCCCC<br>CGGCCAGGGCCTGAAGTGGCTGGGCTGGATCAACACCGCC<br>ACCGGCGAGCCCACCTACGCCGACGACTTCAAGGGCCGGT<br>TCACCATCACCCTGGACACCTCCGCCCGGACCGTGTACCTG<br>GAGATCTCCTCCCTGCGGTCCGAGGACACCGCCACCTACTT<br>CTGCTTCTCCTACTACGACTACTGGGGCCAGGGCACCCTGC<br>TGACCGTGTCCTCCGCCTCCACCAAGGGCCCATCGGTCTTC<br>CCCCTGGCACCCTCCTCCAAGAGCACCTCTGGGGGCACAGC<br>GGCCCTGGGCTGCCTGGTCAAGGACTACTTCCCCGAACCGG<br>TGACGGTGTCGTGGAACTCAGGCGCCCTGACCAGCGGCGT<br>GCACACCTTCCCGGCCGTCCTACAGTCCTCAGGACTCTACT<br>CCCTCAGCAGCGTGGTGACCGTGCCCTCCAGCAGCTTGGGC<br>ACCCAGACCTACATCTGCAACGTGAATCACAAGCCCAGCA<br>ACACCAAGGTGGACAAGAGAGTTGAGCCCAAATCTTGTGA<br>CAAAACTCACACATGCCCACCGTGCCCAGCACCTGAACTCC<br>TGGGGGGACCGTCAGTCTTCCTCTTCCCCCCAAAACCCAAG<br>GACACCCTCATGATCTCCCGGACCCCTGAGGTCACATGCGT |

TABLE 5-continued

| | |
|---|---|
| | GGTGGTGGACGTGAGCCACGAAGACCCTGAGGTCAAGTTC<br>AACTGGTACGTGGACGGCGTGGAGGTGCATAATGCCAAGA<br>CAAAGCCGCGGGAGGAGCAGTACAACAGCACGTACCGTGT<br>GGTCAGCGTCCTCACCGTCCTGCACCAGGACTGGCTGAATG<br>GCAAGGAGTACAAGTGCAAGGTCTCCAACAAAGCCCTCCC<br>AGCCCCCATCGAGAAAACCATCTCCAAAGCCAAAGGGCAG<br>CCCCGAGAACCACAGGTGTACACCCTGCCCCCATCCCGGGA<br>TGAGCTGACCAAGAACCAGGTCAGCCTGACCTGCCTGGTCA<br>AAGGCTTCTATCCCAGCGACATCGCCGTGGAGTGGGAGAG<br>CAATGGGCAGCCGGAGAACAACTACAAGACCACGCCTCCC<br>GTGCTGGACTCCGACGGCTCCTTCTTCCTCTACAGCAAGCT<br>CACCGTGGACAAGAGCAGGTGGCAGCAGGGGAACGTCTTC<br>TCATGCTCCGTGATGCATGAGGCTCTGCACAACCACTACAC<br>GCAGAAGAGCCTCTCCCTGTCTCCGGGTAAATGA<br>(SEQ ID NO: 9) |
| hu763 H2 IgG1 amino acid | QVQLVQSGPEVKKPGASVKISCKASGYTFTDYSMHWVKKAP<br>GQGLKWLGWINTATGEPTYADDFKGRFTITLDTSARTVYLEIS<br>SLRSEDTATYFCFSYYDYWGQGTLLTVSSASTKGPSVFPLAPS<br>SKSTSGGTAALGCLVKDYFPEPVTVSWNSGALTSGVHTFPAV<br>LQSSGLYSLSSVVTVPSSSLGTQTYICNVNHKPSNTKVDKKVE<br>PKSCDKTHTCPPCPAPELLGGPSVFLFPPKPKDTLMISRTPEVT<br>CVVVDVSHEDPEVKFNWYVDGVEVHNAKTKPREEQYNSTYR<br>VVSVLTVLHQDWLNGKEYKCKVSNKALPAPIEKTISKAKGQP<br>REPQVYTLPPSREEMTKNQVSLTCLVKGFYPSDIAVEWESNG<br>QPENNYKTTPPVLDSDGSFFLYSKLTVDKSRWQQGNVFSCSV<br>MHEALHNHYTQKSLSLSPGK (SEQ ID NO: 10) |
| hu763 L1 Igκ cDNA | GAGATCAAGCTGACCCAGTCCCCCTCCATCCTGTCCGTGTC<br>CCCCGGCGAGACCGTGACCCTGTCCTGCCGGGCCTCCCAGA<br>CCATCTACAAGAACCTGCACTGGTACCAGCAGAAGTCCCAC<br>CGGTCCCCCCGGCTGCTGATCAAGTACGGCTCCGACTCCAT<br>CTCCGGCATCCCCGCCCGGTTCTCCGGCTCCGGCTCCGGCA<br>CCGACTACACCCTGACCATCAACTCCGTGAAGCCCGAGGAC<br>GAGGGCATCTACTACTGCCTGCAGGGCTACTCCACCCCCTG<br>GACCTTCGGCCAGGGCACCAAGCTGGAGATCAAGCGGACC<br>GTGGCCGCCCCCTCCGTGTTCATCTTCCCCCCCTCCGACGA<br>GCAGCTGAAGTCCGGCACCGCCTCCGTGGTGTGCCTGCTGA<br>ACAACTTCTACCCCCGGGAGGCCAAGGTGCAGTGGAAGGT<br>GGACAACGCCCTGCAGTCCGGCAACTCCCAGGAGTCCGTG<br>ACCGAGCAGGACTCCAAGGACTCCACCTACTCCCTGTCCTC<br>CACCCTGACCCTGTCCAAGGCCGACTACGAGAAGCACAAG<br>GTGTACGCCTGCGAGGTGACCCACCAGGGCCTGTCCTCCCC<br>CGTGACCAAGTCCTTCAACCGGGGCGAGTGCTAG<br>(SEQ ID NO: 11) |
| hu763 L1 Igκ amino acid | EIKLTQSPSILSVSPGETVTLSCRASQTIYKNLHWYQQKSHRSP<br>RLLIKYGSDSISGIPARFSGSGSGTDYTLTINSVKPEDEGIYYCL<br>QGYSTPWTFGQGTKLEIKRTVAAPSVFIFPPSDEQLKSGTASV<br>VCLLNNFYPREAKVQWKVDNALQSGNSQESVTEQDSKDSTY<br>SLSSTLTLSKADPGVRDRAGLQGLHLLPSSTLTLSKADYEKHK<br>VYACEVTHQGLSSPVTKSFNRGEC (SEQ ID NO: 12) |
| hu763 L2 Igκ cDNA | GAGATCGTGCTGACCCAGTCCCCCGCCACCCTGTCCGTGTC<br>CCCCGGCGAGACCGTGACCCTGTCCTGCCGGGCCTCCCAGA<br>CCATCTACAAGAACCTGCACTGGTACCAGCAGAAGTCCGG<br>CCTGTCCCCCGGCTGCTGATCAAGTACGGCTCCGACTCCA<br>TCTCCGGCATCCCCGCCCGGTTCTCCGGCTCCGGCTCCGGC<br>ACCGACTACACCCTGACCATCAACTCCGTGGAGCCCGAGG<br>ACGAGGGCATCTACTACTGCCTGCAGGGCTACTCCACCCCC<br>TGGACCTTCGGCCAGGGCACCAAGCTGGAGATCAAGCGGA<br>CCGTGGCCGCCCCCTCCGTGTTCATCTTCCCCCCCTCCGACG<br>AGCAGCTGAAGTCCGGCACCGCCTCCGTGGTGTGCCTGCTG<br>AACAACTTCTACCCCCGGGAGGCCAAGGTGCAGTGGAAGG<br>TGGACAACGCCCTGCAGTCCGGCAACTCCCAGGAGTCCGTG<br>ACCGAGCAGGACTCCAAGGACTCCACCTACTCCCTGTCCTC<br>CACCCTGACCCTGTCCAAGGCCGACTACGAGAAGCACAAG<br>GTGTACGCCTGCGAGGTGACCCACCAGGGCCTGTCCTCCCC<br>CGTGACCAAGTCCTTCAACCGGGGCGAGTGCTAG<br>(SEQ ID NO: 13) |
| hu763 L2 Igκ amino acid | EIVLTQSPATLSVSPGETVTLSCRASQTIYKNLHWYQQKSGLSP<br>RLLIKYGSDSISGIPARFSGSGSGTDYTLTINSVEPEDEGIYYCL<br>QGYSTPWTFGQGTKLEIKRTVAAPSVFIFPPSDEQLKSGTASV<br>VCLLNNFYPREAKVQWKVDNALQSGNSQESVTEQDSKDSTY<br>SLSSTLTLSKADYEKHKVYACEVTHQGLSSPVTKSFNRGEC<br>(SEQ ID NO: 14) |
| hu763 H1 IgG4 cDNA | CAGATCCAGCTGGTGCAGTCCGGCCCCGAGGTGAAGAAGC<br>CCGGCGCCTCCGTGAAGATCTCCTGCAAGGCCTCCGGCTAC |

TABLE 5-continued

|  |  |
|---|---|
|  | ACCTTCACCGACTACTCCATGCACTGGGTGAAGAAGGCCCC<br>CGGCCAGGGCCTGGAGTGGCTGGGCTGGATCAACACCGCC<br>ACCGGCGAGCCCACCTACGCCGACGACTTCAAGGGCCGGT<br>TCACCATCACCCTGGACACCTCCGCCCGGACCGTGTACCTG<br>CAGATCAACAACCTGCGGTCCGAGGACACCGCCACCTACTT<br>CTGCTTCTCCTACTACGACTACTGGGGCCAGGGCACCCTGC<br>TGACCGTGTCCTCCGCCTCCACCAAGGGCCCCTCCGTGTTC<br>CCCCTGGCCCCCTGCTCCCGGTCCACCTCCGAGTCCACCGC<br>CGCCCTGGGCTGCCTGGTGAAGGACTACTTCCCCGAGCCCG<br>TGACCGTGTCCTGGAACTCCGGCGCCCTGACCTCCGGCGTG<br>CACACCTTCCCCGCCGTGCTGCAGTCCTCCGGCCTGTACTC<br>CCTGTCCTCCGTGGTGACCGTGCCCTCCTCCTCCCTGGGCAC<br>CAAGACCTACACCTGCAACGTGGACCACAAGCCCTCCAAC<br>ACCAAGGTGGACAAGCGGGTGGAGTCCAAGTACGGCCCCC<br>CCTGCCCCTCCTGCCCCGCCCCCGAGTTCCTGGGCGGCCCC<br>TCCGTGTTCCTGTTCCCCCCCAAGCCCAAGGACACCCTGAT<br>GATCTCCCGGACCCCCGAGGTGACCTGCGTGGTGGTGGACG<br>TGTCCCAGGAGGACCCCGAGGTGCAGTTCAACTGGTACGTG<br>GACGGCGTGGAGGTGCACAACGCCAAGACCAAGCCCCGGG<br>AGGAGCAGTTCAACTCCACCTACCGGGTGGTGTCCGTGCTG<br>ACCGTGCTGCACCAGGACTGGCTGAACGGCAAGGAGTACA<br>AGTGCAAGGTGTCCAACAAGGGCCTGCCCTCCTCCATCGAG<br>AAGACCATCTCCAAGGCCAAGGGCCAGCCCCGGGAGCCCC<br>AGGTGTACACCCTGCCCCCCTCCCAGGAGGAGATGACCAA<br>GAACCAGGTGTCCCTGACCTGCCTGGTGAAGGGCTTCTACC<br>CCTCCGACATCGCCGTGGAGTGGGAGTCCAACGGCCAGCC<br>CGAGAACAACTACAAGACCACCCCCCCCGTGCTGGACTCC<br>GACGGCTCCTTCTTCCTGTACTCCCGGCTGACCGTGGACAA<br>GTCCCGGTGGCAGGAGGGCAACGTGTTCTCCTGCTCCGTGA<br>TGCACGAGGCCCTGCACAACCACTACACCCAGAAGTCCCTG<br>TCCCTGTCCCTGGGCAAG (SEQ ID NO: 15) |
| hu763 H1 IgG4 amino acid | QIQLVQSGPEVKKPGASVKISCKASGYTFTDYSMHWVKKAPG<br>QGLEWLGWINTATGEPTYADDFKGRFTITLDTSARTVYLQINN<br>LRSEDTATYFCFSYYDYWGQGTLLTVSSASTKGPSVFPLAPCS<br>RSTSESTAALGCLVKDYFPEPVTVSWNSGALTSGVHTFPAVLQ<br>SSGLYSLSSVVTVPSSSLGTKTYTCNVDHKPSNTKVDKRVESK<br>YGPPCPSCPAPEFLGGPSVFLFPPKPKDTLMISRTPEVTCVVVD<br>VSQEDPEVQFNWYVDGVEVHNAKTKPREEQFNSTYRVVSVL<br>TVLHQDWLNGKEYKCKVSNKGLPSSIEKTISKAKGQPREPQV<br>YTLPPSQEEMTKNQVSLTCLVKGFYPSDIAVEWESNGQPENN<br>YKTTPPVLDSDGSFFLYSRLTVDKSRWQEGNVFSCSVMHEAL<br>HNHYTQKSLSLSLGK (SEQ ID NO: 16) |
| hu763 H2 IgG4 cDNA | CAGGTGCAGCTGGTGCAGTCCGGCCCCGAGGTGAAGAAGC<br>CCGGCGCCTCCGTGAAGATCTCCTGCAAGGCCTCCGGCTAC<br>ACCTTCACCGACTACTCCATGCACTGGGTGAAGAAGGCCCC<br>CGGCCAGGGCCTGAAGTGGCTGGGCTGGATCAACACCGCC<br>ACCGGCGAGCCCACCTACGCCGACGACTTCAAGGGCCGGT<br>TCACCATCACCCTGGACACCTCCGCCCGGACCGTGTACCTG<br>GAGATCTCCTCCCTGCGGTCCGAGGACACCGCCACCTACTT<br>CTGCTTCTCCTACTACGACTACTGGGGCCAGGGCACCCTGC<br>TGACCGTGTCCTCCGCCTCCACCAAGGGCCCCTCCGTGTTC<br>CCCCTGGCCCCCTGCTCCCGGTCCACCTCCGAGTCCACCGC<br>CGCCCTGGGCTGCCTGGTGAAGGACTACTTCCCCGAGCCCG<br>TGACCGTGTCCTGGAACTCCGGCGCCCTGACCTCCGGCGTG<br>CACACCTTCCCCGCCGTGCTGCAGTCCTCCGGCCTGTACTC<br>CCTGTCCTCCGTGGTGACCGTGCCCTCCTCCTCCCTGGGCAC<br>CAAGACCTACACCTGCAACGTGGACCACAAGCCCTCCAAC<br>ACCAAGGTGGACAAGCGGGTGGAGTCCAAGTACGGCCCCC<br>CCTGCCCCTCCTGCCCCGCCCCCGAGTTCCTGGGCGGCCCC<br>TCCGTGTTCCTGTTCCCCCCCAAGCCCAAGGACACCCTGAT<br>GATCTCCCGGACCCCCGAGGTGACCTGCGTGGTGGTGGACG<br>TGTCCCAGGAGGACCCCGAGGTGCAGTTCAACTGGTACGTG<br>GACGGCGTGGAGGTGCACAACGCCAAGACCAAGCCCCGGG<br>AGGAGCAGTTCAACTCCACCTACCGGGTGGTGTCCGTGCTG<br>ACCGTGCTGCACCAGGACTGGCTGAACGGCAAGGAGTACA<br>AGTGCAAGGTGTCCAACAAGGGCCTGCCCTCCTCCATCGAG<br>AAGACCATCTCCAAGGCCAAGGGCCAGCCCCGGGAGCCCC<br>AGGTGTACACCCTGCCCCCCTCCCAGGAGGAGATGACCAA<br>GAACCAGGTGTCCCTGACCTGCCTGGTGAAGGGCTTCTACC<br>CCTCCGACATCGCCGTGGAGTGGGAGTCCAACGGCCAGCC<br>CGAGAACAACTACAAGACCACCCCCCCCGTGCTGGACTCC<br>GACGGCTCCTTCTTCCTGTACTCCCGGCTGACCGTGGACAA<br>GTCCCGGTGGCAGGAGGGCAACGTGTTCTCCTGCTCCGTGA<br>TGCACGAGGCCCTGCACAACCACTACACCCAGAAGTCCCTG<br>TCCCTGTCCCTGGGCAAG (SEQ ID NO: 17) |
| hu763 H2 IgG4 amino acid | QVQLVQSGPEVKKPGASVKISCKASGYTFTDYSMHWVKKAP<br>GQGLKWLGWINTATGEPTYADDFKGRFTITLDTSARTVYLEIS |

TABLE 5-continued

| | |
|---|---|
| | SLRSEDTATYFCFSYYDYWGQGTLLTVSSASTKGPSVFPLAPC<br>SRSTSESTAALGCLVKDYFPEPVTVSWNSGALTSGVHTFPAVL<br>QSSGLYSLSSVVTVPSSSLGTKTYTCNVDHKPSNTKVDKRVES<br>KYGPPCPSCPAPEFLGGPSVFLFPPKPKDTLMISRTPEVTCVVV<br>DVSQEDPEVQFNWYVDGVEVHNAKTKPREEQFNSTYRVVSV<br>LTVLHQDWLNGKEYKCKVSNKGLPSSIEKTISKAKGQPREPQ<br>VYTLPPSQEEMTKNQVSLTCLVKGFYPSDIAVEWESNGQPEN<br>NYKTTPPVLDSDGSFFLYSRLTVDKSRWQEGNVFSCSVMHEA<br>LHNHYTQKSLSLSLGK (SEQ ID NO: 18) |
| hu763-HC-huOKT3 cDNA | CAGGTGCAGCTGGTGCAGTCCGGCCCCGAGGTGAAGAAGC<br>CCGGCGCCTCCGTGAAGATCTCCTGCAAGGCCTCCGGCTAC<br>ACCTTCACCGACTACTCCATGCACTGGGTGAAGAAGGCCCC<br>CGGCCAGGGCCTGAAGTGGCTGGGCTGGATCAACACCGCC<br>ACCGGCGAGCCCACCTACGCCGACGACTTCAAGGGCCGGT<br>TCACCATCACCCTGGACACCTCCGCCCGGACCGTGTACCTG<br>GAGATCTCCTCCCTGCGGTCCGAGGACACCGCCACCTACTT<br>CTGCTTCTCCTACTACGACTACTGGGGCCAGGGCACCCTGC<br>TGACCGTGTCCTCCGCCTCCACCAAGGGCCCATCGGTCTTC<br>CCCCTGGCACCCTCCTCCAAGAGCACCTCTGGGGGCACAGC<br>GGCCCTGGGCTGCCTGGTCAAGGACTACTTCCCCGAACCGG<br>TGACGGTGTCGTGGAACTCAGGCGCCCTGACCAGCGGCGT<br>GCACACCTTCCCGGCCGTCCTACAGTCCTCAGGACTCTACT<br>CCCTCAGCAGCGTGGTGACCGTGCCCTCCAGCAGCTTGGGC<br>ACCCAGACCTACATCTGCAACGTGAATCACAAGCCCAGCA<br>ACACCAAGGTGGACAAGAGAGTTGAGCCCAAATCTTGTGA<br>CAAAACTCACACATGCCCACCGTGCCCAGCACCTGAACTCC<br>TGGGGGGACCGTCAGTCTTCCTCTTCCCCCCAAAACCCAAG<br>GACACCCTCATGATCTCCCGGACCCCTGAGGTCACATGCGT<br>GGTGGTGGACGTGAGCCACGAAGACCCTGAGGTCAAGTTC<br>AACTGGTACGTGGACGGCGTGGAGGTGCATAATGCCAAGA<br>CAAAGCCGCGGGAGGAGCAGTACGCCAGCACGTACCGTGT<br>GGTCAGCGTCCTCACCGTCCTGCACCAGGACTGGCTGAATG<br>GCAAGGAGTACAAGTGCAAGGTCTCCAACAAAGCCCTCCC<br>AGCCCCCATCGAGAAAACCATCTCCAAAGCCAAAGGGCAG<br>CCCCGAGAACCACAGGTGTACACCCTGCCCCCATCCCGGGA<br>TGAGCTGACCAAGAACCAGGTCAGCCTGACCTGCCTGGTCA<br>AAGGCTTCTATCCCAGCGACATCGCCGTGGAGTGGGAGAG<br>CAATGGGCAGCCGGAGAACAACTACAAGACCACGCCTCCC<br>GTGCTGGACTCCGACGGCTCCTTCTTCCTCTACAGCAAGCT<br>CACCGTGGACAAGAGCAGGTGGCAGCAGGGGAACGTCTTC<br>TCATGCTCCGTGATGCATGAGGCTCTGCACAACCACTACAC<br>GCAGAAGAGCCTCTCCCTGTCTCCGGGTAAAGGATCCGGA<br>GGAGGAGGTAGCGGAGGAGGAGGTTCTGGCGGAGGGGGTT<br>CCCAGGTGCAGCTGGTGCAGAGCGGAGGAGGAGTGGTGCA<br>GCCAGGAAGGAGCCTGCGACTGTCTTGCAAGGCTAGTGGC<br>TACACCTTCACACGATATACTATGCACTGGGTGAGGCAGGC<br>ACCTGGTAAAGGCCTGGAGTGGATCGGCTACATTAACCCCT<br>CTAGGGGATACACCAACTATAATCAGAAGTTCAAAGACAG<br>GTTCACCATCTCACGCGATAACTCCAAGAATACCGCCTTCC<br>TGCAGATGGACTCCCTGCGGCCCGAAGATACAGGCGTGTAT<br>TTTTGCGCTAGATACTATGACGATCATTACTGTCTGGACTAT<br>TGGGGACAGGGGACCCCTGTGACAGTGTCCAGCGGTGGAG<br>GAGGGTCAGGTGGAGGAGGGAGCGGTGGCGGAGGGTCTGA<br>CATCCAGATGACCCAGTCCCCATCTAGTCTGAGCGCCTCTG<br>TGGGCGATAGAGTGACTATTACCTGCAGTGCTTCATCCAGC<br>GTGAGCTACATGAACTGGTATCAGCAGACACCCGGAAAGG<br>CACCTAAACGCTGGATCTACGATACTAGCAAGCTGGCCTCT<br>GGCGTGCCCAGTCGATTCAGTGGTTCAGGCTCCGGAACCGA<br>CTATACCTTCACCATCTCTAGTCTGCAGCCTGAGGATATTG<br>CCACATACTATTGTCAGCAGTGGTCATCCAATCCATTCACT<br>TTTGGGCAGGGTACCAAACTGCAGATTACAAGGTAGGGAT<br>CCGAGCTCGGTACAAACCG (SEQ ID NO: 19) |
| hu763-HC-huOKT3 amino acid | QVQLVQSGPEVKKPGASVKISCKASGYTFTDYSMHWVKKAP<br>GQGLKWLGWINTATGEPTYADDFKGRFTITLDTSARTVYLEIS<br>SLRSEDTATYFCFSYYDYWGQGTLLTVSSASTKGPSVFPLAPS<br>SKSTSGGTAALGCLVKDYFPEPVTVSWNSGALTSGVHTFPAV<br>LQSSGLYSLSSVVTVPSSSLGTQTYICNVNHKPSNTKVDKRVE<br>PKSCDKTHTCPPCPAPELLGGPSVFLFPPKPKDTLMISRTPEVT<br>CVVVDVSHEDPEVKFNWYVDGVEVHNAKTKPREEQYASTYR<br>VVSVLTVLHQDWLNGKEYKCKVSNKALPAPIEKTISKAKGQP<br>REPQVYTLPPSRDELTKNQVSLTCLVKGFYPSDIAVEWESNGQ<br>PENNYKTTPPVLDSDGSFFLYSKLTVDKSRWQQGNVFSCSVM<br>HEALHNHYTQKSLSLSPGKGSGGGGSGGGGSGGGGSQVQLV<br>QSGGGVVQPGRSLRLSCKASGYTFTRYTMHWVRQAPGKGLE<br>WIGYINPSRGYTNYNQKFKDRFTISRDNSKNTAFLQMDSLRPE<br>DTGVYFCARYYDDHYCLDYWGQGTPVTVSSGGGGSGGGGS |

TABLE 5-continued

| | |
|---|---|
| | GGGGSDIQMTQSPSSLSASVGDRVTITCSASSSVSYMNWYQQ<br>TPGKAPKRWIYDTSKLASGVPSRFSGSGSGTDYTFTISSLQPED<br>IATYYCQQWSSNPFTFGQGTKLQITR (SEQ ID NO: 20) |
| hu763-LC-huOKT3 cDNA | GAGATCGTGCTGACCCAGTCCCCCGCCACCCTGTCCGTGTC<br>CCCCGGCGAGACCGTGACCCTGTCCTGCCGGGCCTCCCAGA<br>CCATCTACAAGAACCTGCACTGGTACCAGCAGAAGTCCGG<br>CCTGTCCCCCCGGCTGCTGATCAAGTACGGCTCCGACTCCA<br>TCTCCGGCATCCCCGCCCGGTTCTCCGGCTCCGGCTCCGGC<br>ACCGACTACACCCTGACCATCAACTCCGTGGAGCCCGAGG<br>ACGAGGGCATCTACTACTGCCTGCAGGGCTACTCCACCCCC<br>TGGACCTTCGGCCAGGGCACCAAGCTGGAGATCAAGCGGA<br>CCGTGGCCGCCCCCTCCGTGTTCATCTTCCCCCCCTCCGACG<br>AGCAGCTGAAGTCCGGCACCGCCTCCGTGGTGTGCCTGCTG<br>AACAACTTCTACCCCCGGGAGGCCAAGGTGCAGTGGAAGG<br>TGGACAACGCCCTGCAGTCCGGCAACTCCCAGGAGTCCGTG<br>ACCGAGCAGGACTCCAAGGACTCCACCTACTCCCTGTCCTC<br>CACCCTGACCCTGTCCAAGGCCGACTACGAGAAGCACAAG<br>GTGTACGCCTGCGAGGTGACCCACCAGGGCCTGTCCTCCCC<br>CGTGACCAAGTCCTTCAACCGGGGCGAGTGCACTAGTGGA<br>GGAGGAGGTAGCGGAGGAGGAGGTTCTGGCGGAGGGGGTT<br>CCCAGGTGCAGCTGGTGCAGAGCGGAGGAGGAGTGGTGCA<br>GCCAGGAAGGAGCCTGCGACTGTCTTGCAAGGCTAGTGGC<br>TACACCTTCACACGATATACTATGCACTGGGTGAGGCAGGC<br>ACCTGGTAAAGGCCTGGAGTGGATCGGCTACATTAACCCCT<br>CTAGGGGATACACCAACTATAATCAGAAGTTCAAAGACAG<br>GTTCACCATCTCACGCGATAACTCCAAGAATACCGCCTTCC<br>TGCAGATGGACTCCCTGCGGCCCGAAGATACAGGCGTGTAT<br>TTTTGCGCTAGATACTATGACGATCATTACTGTCTGGACTAT<br>TGGGGACAGGGGACCCCTGTGACAGTGTCCAGCGGTGGAG<br>GAGGGTCAGGTGGAGGAGGGAGCGGTGGCGGAGGGTCTGA<br>CATCCAGATGACCCAGTCCCCATCTAGTCTGAGCGCCTCTG<br>TGGGCGATAGAGTGACTATTACCTGCAGTGCTTCATCCAGC<br>GTGAGCTACATGAACTGGTATCAGCAGACACCCGGAAAGG<br>CACCTAAACGCTGGATCTACGATACTAGCAAGCTGGCCTCT<br>GGCGTGCCCAGTCGATTCAGTGGTTCAGGCTCCGGAACCGA<br>CTATACCTTCACCATCTCTAGTCTGCAGCCTGAGGATATTG<br>CCACATACTATTGTCAGCAGTGGTCATCCAATCCATTCACT<br>TTTGGGCAGGGTACCAAACTGCAGATTACAAGGTAGTCTAG<br>AGCTTGCCTCGAGCAGCGCTGCTCGAGAGATCTACGGGTGG<br>(SEQ ID NO: 21) |
| hu763-LC-huOKT3 amino acid | EIVLTQSPATLSVSPGETVTLSCRASQTIYKNLHWYQQKSGLSP<br>RLLIKYGSDSISGIPARFSGSGSGTDYTLTINSVEPEDEGIYYCL<br>QGYSTPWTFGQGTKLEIKRTVAAPSVFIFPPSDEQLKSGTASV<br>VCLLNNFYPREAKVQWKVDNALQSGNSQESVTEQDSKDSTY<br>SLSSTLTLSKADYEKHKVYACEVTHQGLSSPVTKSFNRGECTS<br>GGGGSGGGGSGGGGSQVQLVQSGGGVVQPGRSLRLSCKASG<br>YTFTRYTMHWVRQAPGKGLEWIGYINPSRGYTNYNQKFKDR<br>FTISRDNSKNTAFLQMDSLRPEDTGVYFCARYYDDHYCLDYW<br>GQGTPVTVSSGGGGSGGGGSGGGGSDIQMTQSPSSLSASVGD<br>RVTITCSASSSVSYMNWYQQTPGKAPKRWIYDTSKLASGVPS<br>RFSGSGSGTDYTFTISSLQPEDIATYYCQQWSSNPFTFGQGTKL<br>QITR (SEQ ID NO: 22) |

In various embodiments, a humanized anti-CSPG4 antibody according to the present invention is composed of heavy and light chain variable regions, wherein the heavy chain variable region contains at least one of the CDRs found in the heavy chain variable region of murine 763 antibody and the light chain variable region contains at least one of the CDRs found in the light chain variable region of murine 763 antibody.

In various embodiments, a humanized anti-CSPG4 antibody according to the present invention is composed of heavy and light chain variable regions, wherein the heavy chain variable region contains at least two of the CDRs found in the heavy chain variable region of murine 763 antibody and the light chain variable region contains at least two of the CDRs found in the light chain variable region of murine 763 antibody.

In various embodiments, a humanized anti-CSPG4 antibody according to the present invention is composed of heavy and light chain variable regions, wherein the heavy chain variable region contains the three CDRs found in the heavy chain variable region of murine 763 antibody and the light chain variable region contains the three CDRs found in the light chain variable region of murine 763 antibody.

In various embodiments, a humanized anti-CSPG4 antibody according to the present invention is composed of heavy and light chain variable regions, wherein the heavy chain variable region contains the three CDRs found in the heavy chain variable region of murine 763 antibody.

In various embodiments, a humanized anti-CSPG4 antibody according to the present invention is composed of heavy and light chain variable regions, wherein the heavy chain variable region contains three CDRs, which CDRs each have a sequence that is at least about 50% (e.g., at least about 55%, 60%, 65%, 70%, 75%, 80%, 85%, 90%, 95%, 96%, 97%, 98%, or 99%) identical to heavy chain CDRs that appear in Table 5.

In various embodiments, a humanized anti-CSPG4 antibody according to the present invention is composed of heavy and light chain variable regions, wherein the heavy chain variable region contains three CDRs, which CDRs each have a sequence that is identical to heavy chain CDRs that appear in Table 5.

In various embodiments, a humanized anti-CSPG4 antibody according to the present invention is composed of heavy and light chain variable regions, wherein the light chain variable region contains the three CDRs found in the light chain variable region of murine 763 antibody.

In various embodiments, a humanized anti-CSPG4 antibody according to the present invention is composed of heavy and light chain variable regions, wherein the light chain variable region contains three CDRs, which CDRs each have a sequence that is at least about 50% (e.g., at least about 55%, 60%, 65%, 70%, 75%, 80%, 85%, 90%, 95%, 96%, 97%, 98%, or 99%) identical to light chain CDRs that appear in Table 5.

In various embodiments, a humanized anti-CSPG4 antibody according to the present invention is composed of heavy and light chain variable regions, wherein the light chain variable region contains three CDRs, which CDRs each have a sequence that is identical to light chain CDRs that appear in Table 5.

In various embodiments, a humanized anti-CSPG4 antibody according to the present invention is composed of heavy and light chain variable regions, wherein the heavy chain variable region has a sequence that is at least about 50% (e.g., at least about 55%, 60%, 65%, 70%, 75%, 80%, 85%, 90%, 95%, 96%, 97%, 98%, or 99%) identical to a heavy chain variable region that appears in Table 5.

In various embodiments, a humanized anti-CSPG4 antibody according to the present invention is composed of heavy and light chain variable regions, wherein the heavy chain variable region has a sequence that is identical to a heavy chain variable region that appears in Table 5.

In various embodiments, a humanized anti-CSPG4 antibody according to the present invention is composed of heavy and light chain variable regions, wherein the light chain variable region has a sequence that is at least about 50% (e.g., at least about 55%, 60%, 65%, 70%, 75%, 80%, 85%, 90%, 95%, 96%, 97%, 98%, or 99%) identical to a light chain variable region that appears in Table 5.

In various embodiments, a humanized anti-CSPG4 antibody according to the present invention is composed of heavy and light chain variable regions, wherein the light chain variable region has a sequence that is identical to a light chain variable region that appears in Table 5.

In various embodiments, a humanized anti-CSPG4 antibody according to the present invention is composed of heavy and light chain variable regions, which heavy chain variable region has a sequence that is at least about 50% (e.g., at least about 55%, 60%, 65%, 70%, 75%, 80%, 85%, 90%, 95%, 96%, 97%, 98%, or 99%) identical to a heavy chain variable region that appears in Table 5, and which light chain variable region has a sequence that is at least about 50% (e.g., at least about 55%, 60%, 65%, 70%, 75%, 80%, 85%, 90%, 95%, 96%, 97%, 98%, or 99%) identical to a light chain variable region that appears in Table 5.

In various embodiments, a humanized anti-CSPG4 antibody according to the present invention is composed of heavy and light chain variable regions, which heavy chain variable region has a sequence that is identical to a heavy chain variable region that appears in Table 5, and which light chain variable region has a sequence that is identical to a light chain variable region that appears in Table 5.

In various embodiments, a humanized anti-CSPG4 antibody according to the present invention is composed of heavy and light chain variable regions that are selected from heavy and light chain variable region sequences that appear in Table 5.

In various embodiments, a bispecific binding agent (e.g., a bispecific antibody) according to the present invention is composed of a first binding component and a second binding component. In many embodiments, first and second binding components of a bispecific binding agent as described herein are each composed of antibody components characterized by different specificities. In many embodiments, antibody components are selected from Table 5.

In various embodiments, a bispecific binding agent according to the present invention comprises a first binding component, a second binding component. In various embodiments, a bispecific binding agent according to the present invention comprises a first binding component, a second binding component and a linker that is connected to both the first and second binding component (e.g., positioned between the first and second binding components).

In various embodiments, first and/or second binding components as described herein comprise or are antibody components. In various embodiments, first and/or second binding components as described herein comprise a linker sequence.

In various embodiments, first and/or second binding components as described herein comprise or are immunoglobulins (e.g., IgGs). In various embodiments, first and/or second binding components binding components as described herein comprise or are antibody fragments (e.g., scFvs). In various embodiments, first binding components as described herein comprise or are immunoglobulins and second binding components comprise or are antibody fragments. In some certain embodiments, first binding components are immunoglobulins and second binding components are antibody fragments. In some certain embodiments, first binding components are IgGs and second binding components are scFvs.

In some certain embodiments, a bispecific binding agent according to the present invention comprises an immunoglobulin, which immunoglobulin comprises a heavy chain and a light chain, and an scFv. In some certain embodiments, scFvs are linked to the C-terminal end of the heavy chain of the immunoglobulin. In some certain embodiments, scFvs are linked to the C-terminal end of the light chain of the immunoglobulin. In various embodiments, scFvs are linked to heavy or light chains via a linker sequence.

In some embodiments, a bispecific binding agent of the present invention comprises a sequence at least about 50% (e.g., at least about 55%, 60%, 65%, 70%, 75%, 80%, 85%, 90%, 95%, 96%, 97%, 98%, or 99%) identical to a sequence that appears in Table 5.

In some embodiments, a bispecific binding agent of the present invention comprises a sequence that is substantially identical to a sequence that appears in Table 5.

In some embodiments, a bispecific binding agent of the present invention comprises a sequence that is identical to a sequence that appears in Table 5.

In some embodiments, a bispecific binding agent of the present invention is selected from a sequence that appears in Table 5.

In various embodiments, a first binding component of a bispecific binding agent as described herein comprises an antibody component having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to an antibody component that appears in Table 5.

In various embodiments, a first binding component of a bispecific binding agent as described herein comprises an antibody component having a sequence that is identical to an antibody component that appears in Table 5.

In various embodiments, a second binding component of a bispecific binding agent as described herein comprises an antibody component having a sequence at least 50% (e.g., 50%, 55%, 60%, 65%, 70%, 75%, 80%, 85%, 90%, 91%, 92%, 93%, 94%, 95%, 96%, 97%, 98%, 99% or more) identical to an antibody component that appears in Table 5.

In various embodiments, a second binding component of a bispecific binding agent as described herein comprises an antibody component having a sequence that is identical to an antibody component that appears in Table 5.

Humanized Antibodies

In some embodiments, the antibodies provided by the present invention are monoclonal antibodies, in particular, humanized versions of cognate anti-CSPG4 antibodies derived from other species. A humanized antibody is, in some embodiments, an antibody produced by recombinant DNA technology, in which some or all of the amino acids of a human immunoglobulin light or heavy chain that are not required for antigen binding (e.g., the constant regions and the framework regions of the variable domains) are used to substitute for the corresponding amino acids from the light or heavy chain of the cognate, nonhuman antibody. By way of example, a humanized version of a murine antibody to a given antigen has on both of its heavy and light chains (1) constant regions of a human antibody; (2) framework regions from the variable domains of a human antibody; and (3) CDRs from the murine antibody. When necessary, one or more residues in the human framework regions can be changed to residues at the corresponding positions in the murine antibody so as to preserve the binding affinity of the humanized antibody to the antigen. This change is sometimes called "back mutation." Similarly, forward mutations may be made to revert back to murine sequence for a desired reason, e.g. stability or affinity to antigen. Humanized antibodies generally are less likely to elicit an immune response in humans as compared to chimeric human antibodies because the former contain considerably fewer non-human components.

Suitable methods for making humanized antibodies of the present invention are described in, e.g., Winter EP 0 239 400; Jones et al. (1986) Nature 321:522-525; Riechmann et al. (1988) Nature 332:323-327; Verhoeyen et al. (1988) Science 239:1534-1536; Queen et al. (1989) Proc. Nat. Acad. Sci. U.S.A. 86:10029; U.S. Pat. No. 6,180,370; and Orlandi et al. (1989) Proc. Natl. Acad. Sci. U.S.A. 86:3833; the disclosures of all of which are incorporated by reference herein in their entireties. Generally, the transplantation of murine (or other non-human) CDRs onto a human antibody is achieved as follows. The cDNAs encoding heavy and light chain variable domains are isolated from a hybridoma. The DNA sequences of the variable domains, including the CDRs, are determined by sequencing. The DNAs, encoding the CDRs are inserted into the corresponding regions of a human antibody heavy or light chain variable domain coding sequences, attached to human constant region gene segments of a desired isotype (e.g., γ1 for $C_H$ and κ for $C_L$), are gene synthesized. The humanized heavy and light chain genes are co-expressed in mammalian host cells (e.g., CHO or NSO cells) to produce soluble humanized antibody. To facilitate large-scale production of antibodies, it is often desirable to select for a high expressor using a DHFR gene or GS gene in the producer line. These producer cell lines are cultured in bioreactors, or hollow fiber culture system, or WAVE technology, to produce bulk cultures of soluble antibody, or to produce transgenic mammals (e.g., goats, cows, or sheep) that express the antibody in milk (see, e.g., U.S. Pat. No. 5,827,690).

Using the above-described approaches, humanized and chimeric versions of the murine 763 antibody, were generated. The cDNAs encoding the murine 763 variable regions of the light and heavy chains were used to construct vectors for expression of murine-human chimeras in which the murine 763 variable regions were linked to human IgG1 (for heavy chain) and human kappa (for light chain) constant regions, as described previously. In addition, novel forms of humanized 763 with variant glycosylation were created, in order to enhance binding to the Fc receptor and enhance antigen affinity.

In order to produce humanized 763 antibodies, the human acceptor framework domains were chosen by homology matching to human germline sequences. Using these chosen human acceptor frameworks, the light and heavy chain variable domains were designed and a number of variants/versions of each were generated and expressed, as described below in Examples.

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716, 111; and International Patent Application Publications WO 98/46645, WO 98/60433, WO 98/24893, WO 98/16664, WO 96/34096, WO 96/33735, and WO 91/10741; each of which is incorporated herein by reference in its entirety. The techniques of Cole et al., and Boerder et al., are also available for the preparation of human monoclonal antibodies (Cole et al. (1985) Monoclonal Antibodies and Cancer Therapy, ed. R. A. Reisfeld & S. Sell, pp. 77-96, New York, Alan R. Liss; Boerner et al. (1991) J. Immunol, 147(1):86-95).

Human antibodies produced using other techniques but retaining the variable regions of the anti-CSPG4 antibody of the present invention are included herein. Human antibodies can also be produced using transgenic mice which are incapable of expressing functional endogenous mouse immunoglobulins, but which can express human immunoglobulin genes (e.g., see Lonberg and Huszar (1995) Int. Rev. Immunol. 13:65-93; Taylor, L. D., et al. (1992) Nucl. Acids Res. 20:6287-6295; Kellermann S-A., and Green L. L. (2002) Current Opinion in Biotechnology 13:593-597; Little M. et al. (2000) Immunol. Today 21:364-370; Murphy, A. J. et al. (2014) Proc. Natl. Acad. Sci. U.S.A 111(14): 5153-5158). For a detailed discussion of this technology for producing human antibodies and human monoclonal antibodies and protocols for producing such antibodies, see, e.g., International Patent Application Publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,886,793; 5,916,771; 5,939,598; and 8,502,018, which are incorporated by reference herein in their entirety.

Also human monoclonal antibodies could be made by immunizing mice transplanted with human peripheral blood leukocytes, splenocytes or bone marrows (e.g., Trioma techniques of XTL). Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al. (1988) Biotechnology 12:899-903).

As used herein, an "anti-CSPG4 antibody", "anti-CSPG4 antibody portion," or "anti-CSPG4 antibody fragment" and/or "anti-CSPG4 antibody variant" and the like include any protein or peptide containing molecule that comprises at least a portion of an immunoglobulin molecule, containing at least one complementarity determining region (CDR) of a heavy or light chain or a ligand binding portion thereof derived from any of the monoclonal antibodies described herein, in combination with a heavy chain or light chain variable region, a heavy chain or light chain constant region, a framework region, or any portion thereof, of non-murine origin, preferably of human origin, which can be incorporated into an antibody of the present invention. Alternatively, the term "anti-CSPG4 antibody" shall refer collectively or individually to hu763IgG1 H1-L1, hu763IgG1 H2-L2, hu763IgG4 H1-L1, hu763IgG4 H2-L2, hu763IgG1n H1-L1, hu763IgG1n H2-L2, hu763IgG1 H1-L2, hu763IgG4 H1-L2, hu763IgG1n H1-L2, hu763IgG1 H2-L1, hu763IgG4 H2-L1, hu763IgG1n H2-L1, and combinations thereof, as well fragments and regions thereof such as single chain variable fragments of the present invention including hu763H1-L1 scFv, hu763H2-L2 scFv, hu763H1-L2 scFv, hu763H2-L1 scFv, and combinations thereof. Such humanized antibody is capable of modulating, decreasing, antagonizing, mitigating, alleviating, blocking, inhibiting, abrogating and/or interfering with at least one cell function in vitro, in situ and/or in vivo, wherein said cell expresses CSPG4. As a non-limiting example, a suitable anti-CSPG4 antibody, specified portion or variant of the present invention can bind with high affinity to an epitope, in particular a peptide epitope, of human CSPG4.

Antibody fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the $C_H1$ domain and/or hinge region of the heavy chain. The various portions of antibodies can be joined together chemically by conventional techniques, or can be prepared as a contiguous protein using genetic engineering techniques.

In some embodiments, chimeric or humanized antibodies of the present invention include those wherein the CDRs are derived from one or more of the anti-CSPG4 antibodies described herein and at least a portion, or the remainder of the antibody is derived from one or more human antibodies. Thus, the human part of the antibody may include the framework, $C_L$, $C_H$ domains (e.g., $C_H1$, $C_H2$, $C_H3$), hinge, $V_L$, $V_H$ regions which are substantially non-immunogenic in humans. The regions of the antibody that are derived from human antibodies need not have 100% identity with human antibodies. In some embodiments, as many of the human amino acid residues as possible are retained in order for the immunogenicity to be negligible, however, the human residues may be modified as necessary to support the antigen binding site formed by the CDRs while simultaneously maximizing the humanization of the antibody. Such changes or variations, in some embodiments, retain or reduce the immunogenicity in humans or other species relative to non-modified antibodies. It is pointed out that a humanized antibody can be produced by a non-human animal or prokaryotic or eukaryotic cell that is capable of expressing functionally rearranged human immunoglobulin (e.g., heavy chain and/or light chain) genes. Further, when the antibody is a single chain antibody, it can comprise a linker peptide that is not found in native human antibodies. For example, an Fv can comprise a linker peptide, such as two to about twenty glycine or other amino acid residues, preferably 8-15 glycine or other amino acid residues, which connects the variable region of the heavy chain and the variable region of the light chain. Such linker peptides are considered to be of human origin.

Antibody humanization can be performed by, for example, synthesizing a combinatorial library comprising the six CDRs of a non-human target monoclonal antibody fused in frame to a pool of individual human frameworks. A human framework library that contains genes representative of all known heavy and light chain human germline genes can be utilized. The resulting combinatorial libraries can then be screened for binding to antigens of interest. This approach can allow for the selection of the most favorable combinations of fully human frameworks in terms of maintaining the binding activity to the parental antibody. Humanized antibodies can then be further optimized by a variety of techniques.

Antibody humanization can be used to evolve mouse or other non-human antibodies into "fully human" antibodies. The resulting antibody contains only human sequence and no mouse or non-human antibody sequence, while maintaining similar binding affinity and specificity as the starting antibody.

In some embodiments, anti-CSPG4 humanized or chimeric antibodies of the present invention comprise a variant Fc region, wherein said variant Fc region comprises at least one amino acid modification relative to a wild-type Fc region (or the parental Fc region), such that said molecule has an altered affinity for an Fc receptor (e.g., an FcγR), provided that said variant Fc region does not have a substitution at positions that make a direct contact with Fc receptor based on crystallographic and structural analysis of Fc-Fc receptor interactions such as those disclosed by Sondermann et al. (2000, Nature, 406:267-273, which is incorporated herein by reference in its entirety). Examples of positions within the Fc region that make a direct contact with an Fc receptor such as an FcγR are amino acids 234-239 (hinge region), amino acids 265-269 (B/C loop), amino acids 297-299 (C'/E loop), and amino acids 327-332 (F/G) loop. In some embodiments, the anti-CSPG4 antibodies of the present invention comprising variant Fc regions comprise modification of at least one residue that makes a direct contact with an FcγR based on structural and crystallographic analysis.

In some embodiments, anti-CSPG4 antibodies of the present invention includes a humanized 763 antibody with an altered affinity for activating and/or inhibitory receptors, having variant Fc regions with one or more amino acid modifications, wherein said one or more amino acid modification is a substitution at position 297 with alanine; in some embodiments, a substitution at 239D, 330L, 332E to enhance FcR affinity. In some embodiments, anti-CSPG4 antibodies of the present invention have an Fc region with variant glycosylation as compared to a parent Fc region; in some embodiments, variant glycosylation includes absence of fucose; in some embodiments, variant glycosylation results from expression in GnT1-deficient CHO cells.

In some embodiments, the present invention includes molecules comprising a variant Fc region with additions, deletions, and/or substitutions to one or more amino acid in the Fc region of an antibody of the present invention in order to alter effector function, or enhance or diminish affinity of antibody to FcR. These mutations are within the skill of a person in the art. Therefore, the present invention includes molecules comprising variant Fc regions that bind with a greater affinity to one or more FcγRs. Such molecules preferably mediate effector function more effectively as discussed infra. In some embodiments, the present invention includes molecules comprising a variant Fc region that bind with a weaker affinity to one or more FcγRs. Reduction or elimination of effector function is desirable in certain cases for example in the case of antibodies whose mechanism of action involves blocking or antagonism but not killing of the cells bearing a target antigen. Further, elimination of effector function is desirable, in some embodiments, when making bispecific antibodies as discussed infra. Reduction or elimination of effector function would be desirable in cases of autoimmune disease where one would block FcγR activating receptors in effector cells (This type of function would be present in the host cells). Generally, increased effector function may be directed to tumor and foreign cells; in some embodiments, effector function may be directed away from tumor cells.

Fc variants of the present invention may be combined with other Fc modifications, including but not limited to modifications that alter effector function. The invention encompasses combining an Fc variant of the invention with other Fc modifications to provide additive, synergistic, or novel properties in antibodies or Fc fusions. Preferably the Fc variants of the invention enhance the phenotype of the modification with which they are combined. For example, if an Fc variant is combined with a mutant known to bind FcγRIIIA with a higher affinity than a comparable molecule comprising a wild type Fc region, the combination with the mutant results in a greater fold enhancement in FcγRIIIA affinity. In some embodiments, Fc variants of the present invention are incorporated into an antibody or Fc fusion that comprises one or more engineered glycoforms, i.e., a carbohydrate composition that is covalently attached to a molecule comprising an Fc region, wherein said carbohydrate composition differs chemically from that of a parent molecule comprising an Fc region. In some embodiments, Fc variants of the present invention are incorporated into an antibody or Fc fusion that comprises variant glycosylation. For example, antibodies may be expressed in glycosylation deficient cell line (e.g., a GnT1-deficient CHO cell) such that the antibody is produced with an Fc region lacking glycosylation as compared to a wild type Fc region, or an Fc region expressed in a cell line not deficient in glycosylation.

The present invention includes antibodies with modified glycosylation sites, preferably without altering the functionality of the antibody, e.g., binding activity CSPG4. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. For example, an Fc-glycoform, hu763-H2L2-IgG1n (or hu763-IgG1n), that lacked certain oligosaccharides including fucose and terminal N-acetylglucosamine was produced in special CHO cells and exhibited enhanced ADCC effector function.

In some embodiments, the present invention encompasses methods of modifying the carbohydrate content of an antibody of the invention by adding or deleting a glycosylation site. Methods for modifying the carbohydrate content of antibodies are well known in the art and are included within the present invention, see, e.g., U.S. Pat. No. 6,218,149; EP 0 359 096 B1; U.S. Patent Publication No. US 2002/0028486; International Patent Application Publication WO 03/035835; U.S. Patent Publication No. 2003/0115614; U.S. Pat. Nos. 6,218,149; 6,472,511; all of which are incorporated herein by reference in their entirety. In some embodiments, the present invention includes methods of modifying the carbohydrate content of an antibody of the invention by deleting one or more endogenous carbohydrate moieties of the antibody. In some certain embodiments, the present invention includes deleting the glycosylation site of the Fc region of an antibody, by modifying position 297 from asparagine to alanine.

Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTIII), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al. (1999) Nat. Biotechnol. 17:176-180; Davies et al. (2001) Biotechnol. Bioeng. 74:288-294; Shields et al. (2002) J. Biol. Chem. 277:26733-26740; Shinkawa et al. (2003) J. Biol. Chem. 278:3466-3473) U.S. Pat. No. 6,602,684; U.S. patent application Ser. No. 10/277,370; U.S. patent application Ser. No. 10/113,929; International Patent Application Publications WO 00/61739A1; WO 01/292246A1; WO 02/311140A1; WO 02/30954A1; POTILLEGENT™ technology (Biowa, Inc. Princeton, N.J.); GLYCOMAB™ glycosylation engineering technology (GLYCART biotechnology AG, Zurich, Switzerland); each of which is incorporated herein by reference in its entirety. See, e.g., International Patent Application Publication WO 00/061739; EA01229125; U.S. Patent Application Publication No. 2003/0115614; Okazaki et al. (2004) JMB, 336:1239-49, each of which is incorporated herein by reference in its entirety.

Multivalent Binding Agents

As those skilled in the art are aware, a multivalent binding agent is a molecular entity or complex that includes binding components that bind specifically to two or more targets (e.g., epitopes). Such multivalent binding agents find a variety of uses in the art, including therapeutic uses. To give but one example, as those skilled in the art are aware, multivalent binding agents have been engineered to facilitate killing of tumor cells by directing (or recruiting) cytotoxic T cells to a tumor site. Examples of tumor antigens include, but are not limited to, alpha fetoprotein (AFP), CA15-3, CA27-29, CA19-9, CA-125, calretinin, carcinoembryonic antigen, CD34, CD99, CD117, chromogranin, cytokeratin, desmin, epithelial membrane protein (EMA), Factor VIII, CD31 FL1, glial fibrillary acidic protein (GFAP), gross cystic disease fluid protein (GCDFP-15), HMB-45, human chorionic gonadotropin (hCG), inhibin, keratin, CD45, a lymphocyte marker, MART-1 (Melan-A), Myo D1, muscle-specific actin (MSA), neurofilament, neuron-specific enolase (NSE), placental alkaline phosphatase (PLAP), prostate-specific antigen, S100 protein, smooth muscle actin (SMA), synaptophysin, thyroglobulin, thyroid transcription factor-1, tumor M2-PK, and vimentin.

The potential efficacy of multispecific binding agents that engage T cells lies in the ability of these agents to direct T cells to a tumor site for T-cell mediated killing. T cells are the most potent effector cells in the immune system at killing aberrant cells and are not capable of Fc-mediated antibody dependent cellular cytotoxicity (ADCC). The mechanism by which such multivalent binding agents direct T cells to a tumor site is through binding of a tumor antigen on the surface of a tumor and a co-receptor on the surface of T cells, CD3. CD3 is a complex of three chains (γ, δ, and ε) expressed on the surface of all mature T cells. Expression of CD3 is almost exclusively restricted to T cells. The anti-CD3 component of a bispecific binding agent can transform a previously unstimulated and uncomitted nonclonal T cell to become potent serial killer of tumor cells (Wolf et al. (2005) Drug Discov. Today 10:1237-1244). Binding agents of this type have demonstrated efficacy in animal xenograft studies of solid tumors expressing the epithelial cell adhesion molecule (EpCAM) antigens in addition to other targets (Bargou et al. (2008) Science 321:974-977; Brischwein et al. (2006) Mol. Immunol. 43:1129-1143; Baeuerle and Reinhardt (2009) Cancer Res. 69:4941-4944).

In some embodiments, multivalent binding agents for use in accordance with the present invention are bispecific binding agents. In many embodiments, such bispecific binding agents are capable of binding to T cells. In many embodiments, such bispecific binding agents are capable of binding to CD3 on T cells.

In some embodiments, multivalent or bispecific binding agents for use in accordance with the present invention are or comprise antibody components. A variety of technologies are known in the art for designing, constructing, and/or producing multispecific or bispecific binding agents comprising antibody components.

For example, bispecific binding agents have been constructed that either utilize the full immunoglobulin framework (e.g., IgG), single chain variable fragment (scFv), or combinations thereof. Bispecific binding agents composed of two scFv units in tandem has been shown to be one of the most clinically successful bispecific antibody formats. In the case of anti-tumor immunotherapy, bispecific binding agents that comprise two single chain variable fragments (scFvs) in tandem have been designed such that an scFv that binds a tumor antigen is linked with an scFv that engages T cells by binding CD3. In this way, T cells are recruited to a tumor site in the hope that they can mediate killing of the tumor cells making up the tumor by the cytotoxic properties that certain T cells have. An example of such a bispecific binding agent has been made that targets CD19 and CD3 for lymphoma (termed Bispecific T cell Engaging, or BiTE; e.g., see Dreier et al. (2003) J. Immunol. 170:4397-4402; Bargou et al. (2008) Science 321:974-977), which has been successful in preventing tumor growth in animal xenograft studies. In human studies, this bispecific binding agent demonstrated objective tumor response, including five partial and two complete remissions.

Bispecific binding agents (e.g., bispecific antibodies) of the present invention are based on the particular insight that certain formats may be more beneficial for certain targets (e.g., a tumor antigen) when engaging T cells via CD3. For example, bispecific antibodies provided herein utilize a combination of a full IgG and an scFv. Such bispecific antibodies demonstrate bivalent binding via the IgG component (e.g., anti-CSPG4) and monovalent binding via the scFv component (e.g., anti-CD3). As described herein, bispecific antibodies having this format demonstrate a very high potency to kill tumor cells (i.e., have a very low $EC_{50}$).

This high potency is due, in part, to the increased avidity resulting from the combination of bivalent and monovalent binding components into a single molecule and results in enhanced targeting of T cells to tumor cells. Moreover, by employing monovalent binding for the anti-CD3 component, overstimulation of T cells in the absence of tumors is avoided, thereby eliminating cytokine storm, which is a tremendous safety concern for patients and very common side effect for bispecific agents that target CD3 on T cells.

Exemplary bispecific binding agents include those with a first antibody component specific for a tumor antigen and a second antibody component specific for a cytotoxic marker, e.g., an Fc receptor (e.g., FcγRI, FcγRII, FcγRIII, etc.) or a T cell marker (e.g., CD3, CD28, etc.). Further, the second antibody component can be substituted with an antibody component having a different desired specificity. For example, a bispecific binding agent with a first antibody component specific for a tumor antigen and a second antibody component specific for a toxin can be paired so as to deliver a toxin (e.g., saporin, vinca alkaloid, etc.) to a tumor cell. Other exemplary bispecific binding agents include those with a first antibody component specific for an activating receptor (e.g., B cell receptor, FcγRI, FcγRIIA, FcγRIIIA, FcγRI, T cell receptor, etc.) and a second antibody component specific for an inhibitory receptor (e.g., FcγRIIB, CD5, CD22, CD72, CD300a, etc.). Yet another example includes a second antibody component specific to a different antigen on the same cell type for which a first antibody component is specific, for example, CD20, CD19, CD21, CD23, CD46, CD80, HLA-DR, CD74, MUC1, and CD22 on B-cells. Such bispecific binding agents can be constructed for therapeutic conditions associated with cell activation (e.g. allergy and asthma). Bispecific binding agents can be made, for example, by combining heavy chains and/or light chains that recognize different epitopes of the same or different antigen. In some embodiments, by molecular function, a bispecific binding agent binds one antigen (or epitope) on one of its two binding arms (one $V_H/V_L$ pair), and binds a different antigen (or epitope) on its second arm (a different $V_H/V_L$ pair). By this definition, a bispecific binding agent has two distinct antigen binding arms (in both specificity and CDR sequences), and is monovalent for each antigen to which it binds.

In some embodiments, bispecific binding agents of the present invention are characterized by the ability to can bind simultaneously to two targets which are of different structure. In some embodiments, bispecific binding agents of the present invention have at least one component that specifically binds to, for example, a B-cell, T-cell, myeloid, plasma, or a mast cell antigen or epitope and at least one other component that specifically binds to a targetable conjugate that bears a therapeutic or diagnostic agent.

The tumor antigen CSPG4 is highly expressed in several melanomas, and there have been no successful humanized antibodies nor bispecific humanized antibodies based on the murine 763 antibody. Humanized 763 antibodies as described herein demonstrate high affinity to CSPG4 and bind to a non-carbohydrate (peptide) epitope and usually low $k_{off}$ rates as measured by Biacore. Also, bispecific binding proteins employing humanized 763 antibodies as described herein are capable of bivalent binding to CSPG4 and monovalent binding to CD3 which results in enhanced potency for killing CSPG4$^+$ tumors and increased safety from a lack of overstimulation of CD3. As such, the strategy for employing the format of the bispecific binding proteins as described represents a unique approach for enhanced tumor killing, reduced adverse effects, and demonstrates a potent therapeutic for the treatment of several CSPG4-positive cancers.

Targets

Among other things, the present invention encompasses the recognition that multispecific binding agents, and particularly bispecific binding agents such as bispecific antibodies, are particularly useful and/or effective to facilitate cell killing. In particular, the present invention demonstrates that activity of multivalent binding agents that bind specifically to both a target-cell-associated epitope (e.g., a melanoma-associated tumor antigen) and a lymphocyte-associated epitope (e.g., a T cell surface protein) can be an effective immunotherapy for melanoma-associated cancers.

For example, in some embodiments of the present invention, a multivalent binding agent binds specifically to a tumor-cell-associated epitope and a T-cell epitope. In accordance with such embodiments, the multivalent binding agent can facilitate binding of the agent to one or both of its target epitopes and/or can enhance killing of the target tumor cell as mediated by the target T cell.

In some embodiments, target cells to be killed include, for example, cells that express a tumor antigen (e.g., a melanoma-associated tumor antigen). Those of ordinary skill in the art will be aware of appropriate target epitopes on such cells to which multivalent binding agents as described herein desirably bind.

In some embodiments, lymphocyte cells that can mediate killing of target cells as described herein include T cells (e.g., $CD8^+$ T cells), natural killer (NK) cells, macrophages, granulocytes and antibody-dependent cytotoxic cells. Those of ordinary skill in the art will be aware of appropriate target epitopes on such lymphocytes to which multivalent binding agents as described herein desirably bind. Representative such epitopes can be found on antigens such as, for example, Fc receptor of IgG (e.g., FcγRIIB), CD Id, CD3, CD4, CD7, CD8, CD13, CD14, CD16, CD31, CD38, CD56, CD68, MAC-1/MAC-3, IL-2Ra, OX40, Ly49, and CD94.

Nucleic Acid Construction and Expression

Humanized antibodies and multispecific binding agents (e.g., bispecific antibodies) as described herein may be produced from nucleic acid molecules using molecular biological methods known to the art. Nucleic acid molecules are inserted into a vector that is able to express the fusion proteins in when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the fusion proteins of the present invention under control of transcriptional/translational control signals. These methods may include in vitro recombinant DNA and synthetic techniques and in vivo recombination (See Sambrook et al. Molecular Cloning, A Laboratory Manual, Cold Spring Harbor Laboratory; Current Protocols in Molecular Biology, Eds. Ausubel, et al, Greene Publ. Assoc., Wiley-Interscience, NY).

Expression of nucleic acid molecules in accordance with the present invention may be regulated by a second nucleic acid sequence so that the molecule is expressed in a host transformed with the recombinant DNA molecule. For example, expression of the nucleic acid molecules of the invention may be controlled by a promoter and/or enhancer element, which are known in the art.

Nucleic acid constructs include regions that encode multispecific binding proteins generated from antibodies and/or antibody components. Typically, such multispecific binding proteins will be generated from $V_H$ and/or $V_L$ regions. After identification and selection of antibodies exhibiting desired binding and/or functional properties, variable regions of each antibody are isolated, amplified, cloned and sequenced. Modifications may be made to the $V_H$ and $V_L$ nucleotide sequences, including additions of nucleotide sequences encoding amino acids and/or carrying restriction sites, deletions of nucleotide sequences encoding amino acids, or substitutions of nucleotide sequences encoding amino acids. The antibodies and/or antibody components may be generated from human, humanized or chimeric antibodies.

Nucleic acid constructs of the present invention are inserted into an expression vector or viral vector by methods known to the art, and nucleic acid molecules are operatively linked to an expression control sequence.

Where appropriate, nucleic acid sequences that encode humanized antibodies and multispecific binding agents as described herein may be modified to include codons that are optimized for expression in a particular cell type or organism (e.g., see U.S. Pat. Nos. 5,670,356 and 5,874,304). Codon optimized sequences are synthetic sequences, and preferably encode the identical polypeptide (or a biologically active fragment of a full length polypeptide which has substantially the same activity as the full length polypeptide) encoded by the non-codon optimized parent polynucleotide. In some embodiments, the coding region of the genetic material encoding antibody components, in whole or in part, may include an altered sequence to optimize codon usage for a particular cell type (e.g., a eukaryotic or prokaryotic cell). For example, the coding sequence for a humanized heavy (or light) chain variable region as described herein may be optimized for expression in a bacterial cells. Alternatively, the coding sequence may be optimized for expression in a mammalian cell (e.g., a CHO). Such a sequence may be described as a codon-optimized sequence.

An expression vector containing a nucleic acid molecule is transformed into a suitable host cell to allow for production of the protein encoded by the nucleic acid constructs. Exemplary host cells include prokaryotes (e.g., *E. coli*) and eukaryotes (e.g., a COS or CHO cell). Host cells transformed with an expression vector are grown under conditions permitting production of a humanized antibody or multispecific binding agent of the present invention followed by recovery of the humanized antibody or multispecific binding agent.

Humanized antibodies and/or multispecific binding agents of the present invention may be purified by any technique, which allows for the subsequent formation of a stable antibody or binding agent molecule. For example, not wishing to be bound by theory, antibodies and/or multispecific binding agents may be recovered from cells either as soluble polypeptides or as inclusion bodies, from which they may be extracted quantitatively by 8M guanidinium hydrochloride and dialysis. In order to further purify antibodies and/or multispecific binding agents of the present invention, conventional ion exchange chromatography, hydrophobic interaction chromatography, reverse phase chromatography or gel filtration may be used. Humanized antibodies and/or multispecific binding agents of the present invention may also be recovered from conditioned media following secretion from eukaryotic or prokaryotic cells.

Screening and Detection Methods

Humanized antibodies and/or multispecific binding agents of the present invention may also be used in in vitro or in vivo screening methods where it is desirable to detect and/or measure one or more activities of a cell or cells (e.g., apoptosis or cell growth). Screening methods are well known to the art and include cell-free, cell-based, and animal assays. In vitro assays can be either solid state or soluble target molecule detection may be achieved in a number of ways known to the art, including the use of a label or detectable group capable of identifying a humanized antibody or a multispecific binding agent which is bound to a target molecule (e.g., cell surface antigen). Detectable labels may be used in conjunction with assays using humanized antibodies or multispecific binding agents of the present invention.

Therapeutic Methods

The ability of humanized antibodies and/or multispecific binding agents of the present invention to exhibit high affinity binding for one of the target antigens makes them therapeutically useful for efficiently targeting cells expressing the target antigen. Thus, it some embodiments, it may be desirable to increase the affinity of a humanized antibody or multispecific binding agent for one target antigen and not the other target antigen that is also bound by the multispecific binding agent (or an Fc receptor in the case of a humanized antibody). For example, in the context of tumor killing, certain conditions may benefit from an increase in affinity to a tumor antigen but not to an antigen on the surface of a cell capable of mediating killing of the tumor (e.g., a T cell). Thus, it may be beneficial to increase the binding affinity of a humanized antibody or multispecific binding agent to a tumor antigen in a patient having a tumor that expresses the tumor antigen through the use of a humanized antibody or multispecific binding agent as described herein.

The present invention provides a humanized antibody and/or multispecific binding agent as described herein as a therapeutic for the treatment of patients having a tumor that expresses an antigen that is capable of being bound by such a multispecific binding agent. Such humanized antibodies and/or multispecific binding agents may be used in a method of treatment of the human or animal body, or in a method of diagnosis.

Administration

The present invention provides methods of administering an effective amount of a therapeutic active described herein (e.g., a humanized antibody or multispecific binding agent) to a subject in need of treatment.

Humanized antibodies or multispecific binding agents as described herein may be administered through various methods known in the art for the therapeutic delivery of agents, such as proteins or nucleic acids can be used for the therapeutic delivery of a humanized antibody or multispecific binding agent or a nucleic acid encoding a humanized antibody or multispecific binding agent of the present invention for killing or inhibiting growth of target cells in a subject, e.g., cellular transfection, gene therapy, direct administration with a delivery vehicle or pharmaceutically acceptable carrier, indirect delivery by providing recombinant cells comprising a nucleic acid encoding a multispecific binding agent of the present invention.

Various delivery systems are known and can be used to administer a humanized antibody or multispecific binding agent of the present invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Routes of administration can be enteral or parenteral and include, but are not limited to, intravenous, subcutaneous, intramuscular, parenteral, transdermal, or transmucosal (e.g., oral or nasal). In some embodiments, multispecific binding agents of the present invention are administered intravenously. In some embodiments, multispecific binding agents of the present invention are administered subcutaneously. In some embodiments, multispecific binding agents are administered together with other biologically active agents.

Pharmaceutical Compositions

The present invention further provides pharmaceutical compositions comprising humanized antibodies or multispecific binding agents of the present invention and a pharmaceutically acceptable carrier or excipient. The composition, if desired, can also contain one or more additional therapeutically active substances.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation.

Formulations of the pharmaceutical compositions described herein may be prepared by any method known or hereafter developed in the art of pharmacology. In general, such preparatory methods include the step of bringing the active ingredient into association with a diluent or another excipient and/or one or more other accessory ingredients, and then, if necessary and/or desirable, shaping and/or packaging the product into a desired single- or multi-dose unit.

A pharmaceutical composition in accordance with the present invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient that would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition in accordance with the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. Remington's The Science and Practice of Pharmacy, 21st Edition, A. R. Gennaro (Lippincott, Williams & Wilkins, Baltimore, Md., 2006; incorporated herein by reference) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, a pharmaceutically acceptable excipient is at least 95%, at least 96%, at least 97%, at least 98%, at least 99%, or 100% pure. In some embodiments, an excipient is approved for use in humans and for veterinary use. In some embodiments, an excipient is approved by the United States Food and Drug Administration. In some embodiments, an excipient is pharmaceutical grade. In some embodiments, an excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in pharmaceutical formulations. Excipients such as cocoa butter and suppository waxes, coloring agents, coating agents, sweetening, flavoring, and/or perfuming agents can be present in the composition, according to the judgment of the formulator.

General considerations in the formulation and/or manufacture of pharmaceutical agents may be found, for example, in Remington: The Science and Practice of Pharmacy 21st ed., Lippincott Williams & Wilkins, 2005 (incorporated herein by reference).

Kits

The present invention further provides a pharmaceutical pack or kit comprising one or more containers filled with at least one humanized antibody or multispecific binding agent (e.g., a bispecific antibody) as described herein. Kits may be used in any applicable method, including, for example, diagnostically. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Other features of the invention will become apparent in the course of the following descriptions of exemplary embodiments, which are given for illustration of the invention and are not intended to be limiting thereof.

EXAMPLES

The following examples are provided so as to describe to those of ordinary skill in the art how to make and use methods and compositions of the invention, and are not intended to limit the scope of what the inventors regard as their invention. Unless indicated otherwise, temperature is indicated in Celsius, and pressure is at or near atmospheric.

Example 1. Selection of Murine 763 as Anti-CSPG4 Antibody of Interest

Among other things, the present invention encompasses the insight that the murine anti-CSPG4 known as 763 (as an abbreviation for clone 763.74) was of particular interest for humanization. Without wishing to be bound by any particular theory, present inventors proposed that high affinity (particularly single digit nanomolecular affinity) and slow $k_{off}$ (desirably $10^{-5}$ or slower) would be particularly desirable for an antibody to be humanized, and/or to be incorporated into a multispecific format.

We tested four candidate anti-CSPG4 antibodies with nonoverlapping epitope specificities for their leaking after binding to CSPG4+ tumor cell line M14. As shown in Table 6 and FIG. 1, 763 was found to have the slowest $k_{off}$ rate, based on the binding kinetics as determined using a BIO-CORE T-100 machine. The slow $k_{off}$ of antibodies translated into a slower wash-off when antibodies were reacted with CSPG4+ M14 tumor cells and then washed multiple times in wash buffer. With each wash, the remaining antibodies on the cell surface were detected using a secondary FITC-labeled goat anti-mouse antibody and mean fluorescent intensity determined by flow cytometry. Based on MFI, 763 and 225.28s had stronger reactivity compared to D2.8.5 or 9.2.27.

We also defined as a selection parameter that a desirable mouse antibody for humanization would not have excessive affinity (e.g., 9.2.27) since a 0.03 nM affinity could lead to affinity barrier issues (Weinstein et al. (1992) Cancer Res. 52:2747s-2751s).

Still further, we defined as a selection parameter that a desirable mouse antibody for humanization would bind to a peptide epitope (and particularly to a conformational epitope), rather than to carbohydrate (9.2.27; Hwang et al. (1985) Cancer Res. 45:4150-4155) or linear peptide (225.28s) epitope. We note that previous reports of peptide mimics that reacted with 763 had homology (position 289-294) with CSPG4 but very low affinity (Geiser et al. Cancer Res. 59:905, 1999), and therefore not the cognate epitope recognized by 763.

TABLE 6

| Antibody | Parental Ab isotype/ format | $K_{on}$ | $K_{off}$ | $K_d$ | Epitope |
|---|---|---|---|---|---|
| 763.74 | mouse IgG1 | 2.96E+04 | 3.81E-05 | 1.3 | Conformation epitope 1289-1760 (D2.8.11) |
| 225.28s | mouse IgG2a | 1.20E-04 | 1.44E-04 | 1.2 | Linear epitope 1705-1712[5,6] |
| 9.2.27 | mouse IgG2a | — | — | 0.03 | Carbohydrate epitope[7] |
| D2.8.5 | scFv | 1.32E+05 | 3.50E-04 | 2.65 | peptide (D2.8.5) |

Example 2. Humanization of Murine Anti-CSPG4 Antibody 763

CSPG4 (Chondroitin sulfate proteoglycan 4) or HMW-MAA (high molecular weight melanoma associated antigen) is an established melanoma associated tumor antigen. In fresh melanoma tissues, it is homogeneously and strongly expressed and yet highly restricted in normal human tissues. More recently, CSPG4 was found to be overexpressed in triple negative breast cancer stem cells (Wang et al., JNCI 102:1496-1512). CSPG4 has been successfully targeted using monoclonal antibodies carrying α-emitting isotopes in patients with melanoma (Raja, C. et al. (2007) Cancer Biol. Ther. 6:846-852). The present Example describes production of humanized antibodies based on murine antibody 763, which is specific for chondroitin sulfate proteoglycan 4 (CSPG4). Although murine 763 antibody has been previously described, it has not been used as a basis for the construction of chimeric or humanized antibodies. The data presented herein describes the successful production of several humanized 763 antibodies in multiple formats such as, for example, a humanized 763 IgG1, a humanized 763 IgG4 and a humanized IgG1n (a special glycoform) that was expressed in an engineered CHO cell.

Additional Examples presented herein demonstrate that all humanized 763 antibody formats showed antigen binding comparable to murine 763, kept favorable $K_D$ and unusually $K_{off}$, mediate antibody-dependent cell-mediated cytotoxicity (ADCC) with high potency to melanoma cells (e.g., humanized 763-IgG1n), and are able to engage T cells to specifically target CSPG4+ tumor cells when in the context of bispecific antibodies.

Briefly, humanized formats of murine 763 antibody (humanized 763-IgG1, humanized 763-IgG4, and humanized 763-IgG1n) were constructed. Sequence design was based on human IgG homology calculations while conserving critical mouse amino acid residues. The CDRs of the heavy and light chains of murine 763 were grafted onto human IgG1 frameworks based on their homology with human frameworks IgGHV3-33 and IGLKV3-15, respectively, and of the allotypes Km3 and G1m3, respectively. Two different heavy chain and two different light chain sequences were expressed as full IgGs and tested for binding and stability. The most stable combination (H2/L2), without forming aggregates by HPLC on repeat freeze/thaw cycles, was chosen for the final form of humanized 763 for the rest of the experiments. Additional constructs were made using a human IgG4 framework. In addition a chimeric 763 antibody was made using human $C_L$ of kappa (κ) light chain and human $C_H1$-$C_H2$-$C_H3$ of gamma1 heavy chain constant regions. Exemplary antibodies made in accordance with this Example are set forth in Table 7.

Figure 2A:
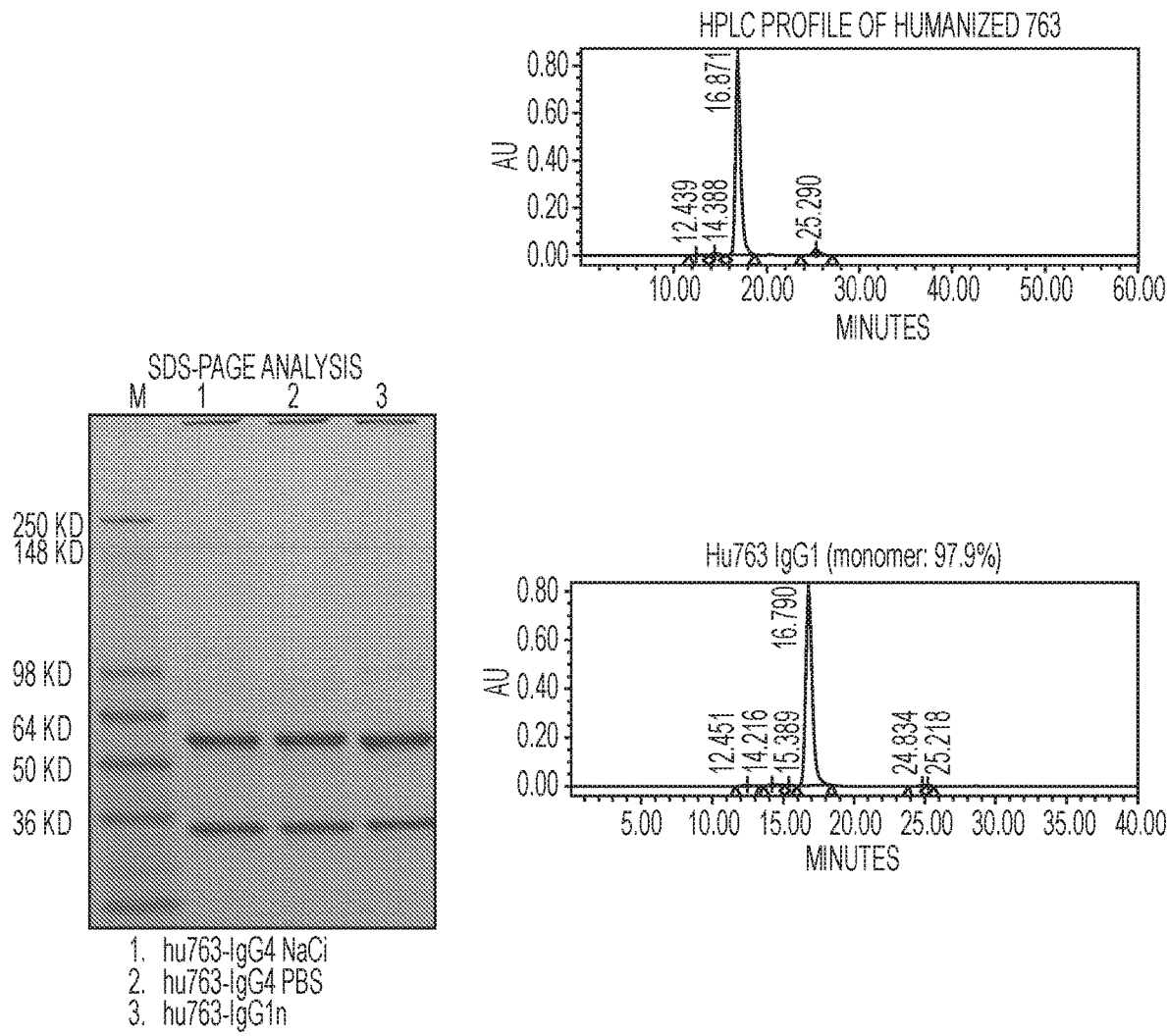
FIG. 2 shows exemplary biochemical analysis of humanized 763 antibodies by reduced SDS-PAGE (A) and SE-HPLC chromatography (B). The major peak (around 16.7 min) in SE-HPLC is the main peak of IgG1 and IgG4. Twenty-five minutes corresponds to the salt buffer peak.
Figure 2B:
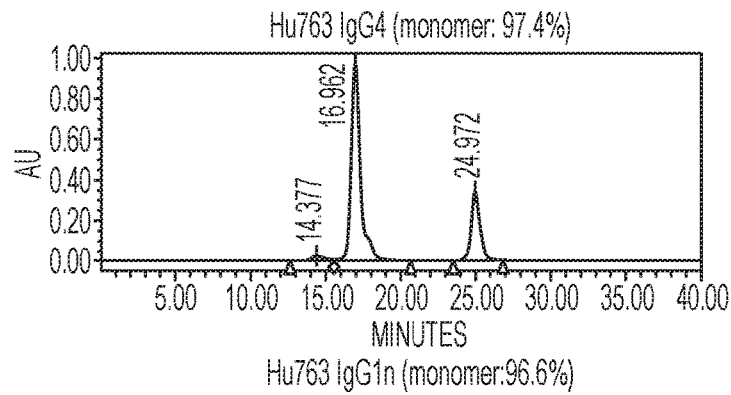

Humanized 763 antibodies were packaged in a single vector (for balanced heavy chain and light chain secretion) and transduced into CHO-DG44 cells using bluescript vectors. Hu763-IgG1n is a humanized 763 IgG1 antibody glycoform expressed in CHO cells with variant glycosylation from a GnT1 deficiency (Jefferis, R. (2009) Nat Rev Drug Discov 8:226-234; Idusogie, E. E. et al. (2000) J. Immunol. 164:4178-4184). Humanized 763 IgG1, humanized 763 IgG4 and humanized 763 IgG1n were purified using standard protein A affinity chromatography. Sugar analysis confirmed that humanized 763 IgG1n had 78.3% (Mol %) Mannose, 20.5% (Mol %) N-Acetyl Glucosamine and 1.2% (Mol %) Glucose. On SDS gel, humanized 763 migrated as IgG with the appropriate size heavy and light chains; and by HPLC, they all eluted as whole IgG with <5% aggregate formation (FIG. 2).

TABLE 7

| Name | Description |
| --- | --- |
| hu763IgG1 H1-L1 | humanized 763 H1 and L1 in IgG1 format |
| hu763IgG1 H2-L2 | humanized 763 H2 and L2 in IgG1 format |
| hu763IgG4 H1-L1 | humanized 763 H1 and L1 in IgG4 format |
| hu763IgG4 H2-L2 | humanized 763 H2 and L2 in IgG4 format |
| hu763IgG1n H2-L2 | humanized 763 H2 and L2 in IgG1 format with variant glycosylation |
| ch763IgG1 | chimeric 763 HC and LC in IgG1 format |

Example 3. Antigen Binding Kinetics of Humanized 763 Antibodies

This Example illustrates the effect of humanization made in accordance with Example 1 on the functional affinity to CSPG4. In some cases, humanized 763 antibodies may bind to CSPG4 for short periods of time (e.g., poor retention due to size). In this example, humanized 763 antibodies demonstrate favorable $K_D$ and unusually slow $k_{off}$ rates.

Figure 3A:
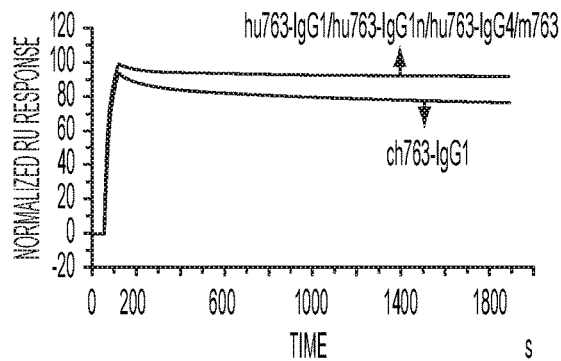
FIG. 3 shows exemplary antigen binding of chimeric and humanized 763 antibodies. A-C, Composite sensograms showing the binding of chimeric and humanized 763 antibodies on antigen D2.8.11-coated chips (A) or on anti-763 idiotype antibody MK2-23 coated chips (B and C), which were measured by surface plasmon resonance (Biacore T-100). D-E, Tumor antigen binding of humanized 763 antibodies. D, FACS analysis of humanized or mouse 763 antibodies to M14 cells. Hu763-IgG1 was also subjected to five cycles of a freeze and thaw process. For humanized 763 IgG1, binding was detected with a FITC conjugated goat anti-human secondary antibody. For mouse 763, binding was detected with a FITC conjugated goat anti-mouse secondary antibody. Antigen binding was expressed as % of MFI of maximum binding at 5 μg. E, ELISA analysis of hu763-IgG1 and hu763-IgG1n on M14 cells coated plates. Binding was detected with HRP conjugated goat anti-human secondary antibody. Hu763-IgG1n was subjected to five cycles of a freeze and thaw process.
Figure 3B:
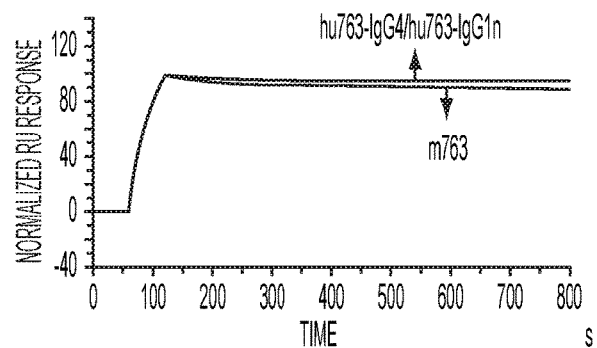
Figure 3C:
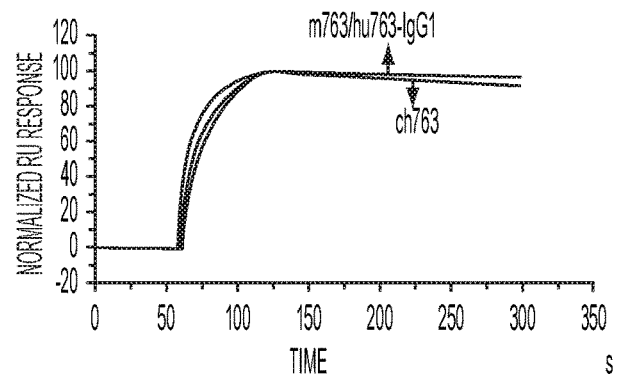

Briefly, antigen (D2.8.11, a peptide epitope for murine 763) or anti-763 idiotype antibody MK2-23 was immobilized onto CM5 chips, kinetics of antibody binding ($k_{on}$, $k_{off}$ and $K_D$) were compared by surface plasma resonance (SPR) using Biacore T-100 (FIG. 3A). For binding to D2.8.11, humanized 763 antibodies including humanized IgG1 and IgG4 demonstrated slower $k_{off}$ than murine 763, and better $K_D$ than murine 763 (see Table 8; 1.34 pM for mouse 763, 1.29 pM for hu763-IgG1, 1.15 pM for hu763-IgG1n and 1.22 pM for hu763-IgG4). Similarly, for binding to MK2-23, both chimeric 763 and humanized 763 antibodies showed comparable binding to murine 763 (FIGS. 3B and 3C), as well as slightly better $K_D$ (Tables 9 and 10).

Figure 3D:
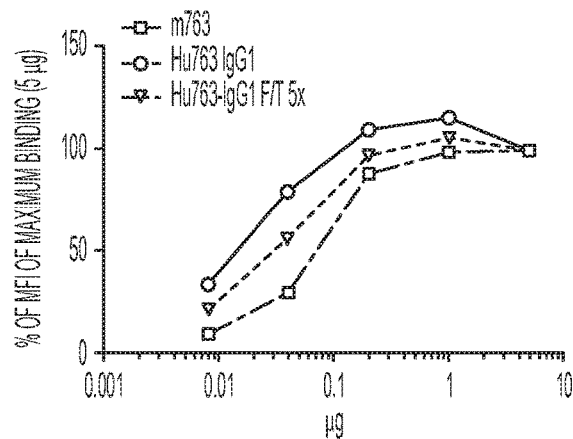

Antigen binding was also analyzed by FACS analysis using CSPG4 positive melanoma M14 cells. For humanized 763 antibodies, cell binding was determined using a FITC-labeled goat anti-human secondary antibody. For murine 763, a FITC-labeled goat anti-mouse secondary antibody was used (FIG. 3D). Data were expressed as mean fluorescent intensity determined by flow cytometry and normalized as percentage of binding of the highest concentration of antibody used (5 μg/$10^6$ cells). Hu763-IgG1 showed better $EC_{50}$ (0.02 μg/1 million cells) than that of murine 763 (0.07 μg/1 million cells). Hu763-IgG1 is quite stable, its $EC_{50}$ of antigen binding is 0.03 μg/1 million cells after subjected to five cycles of freezing and thawing process.

Figure 3E:
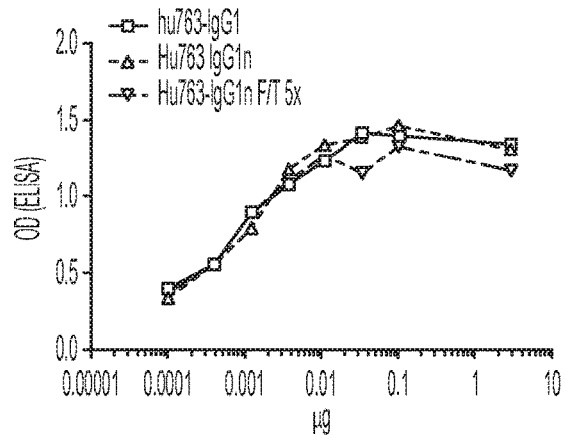

An ELISA method using coated M14 as antigen was also used to assay hu763-IgG1 and hu763-IgG1n binding (FIG. 3E). Both hu763-IgG1 and hu763-IgG1 showed comparable binding to M14 cells. Hu763-IgG1n still bound to M14 cells well after subjected to five cycles of freezing and thawing process.

TABLE 8

Biacore analysis of antigen binding on peptide D2.8.11

| Antibody | $k_{on}$ (1/Ms) | $k_{off}$ (1/s) | $K_D = k_{off}/k_{on}$ (M) |
| --- | --- | --- | --- |
| murine 763 | 2.90E+04 | 3.89E−05 | 1.34E−09 |
| ch763-IgG1 | 3.51E+04 | 2.95E−03 | 8.40E−08 |
| hu763-IgG1 | 2.96E+04 | 3.81E−05 | 1.29E−09 |
| hu763-IgG1n | 2.85E+04 | 3.28E−05 | 1.15E−09 |
| hu763-IgG4 | 2.87E+04 | 3.50E−05 | 1.22E−09 |

TABLE 9

Biacore analysis of antigen binding on anti-idiotype MK2-23

| Antibody | $k_{on}$ (1/Ms) | $k_{off}$ (1/s) | $K_D = k_{off}/k_{on}$ (M) |
| --- | --- | --- | --- |
| murine 763 | 1.46E+05 | 8.50E−05 | 5.82E−10 |
| hu763-IgG1n | 1.68E+05 | 7.54E−05 | 4.49E−10 |
| hu763-IgG4 | 1.67E+05 | 8.01E−05 | 4.80E−10 |

TABLE 10

Biacore analysis of antigen binding on anti-idiotype MK2-23

| Antibody | $k_{on}$ (1/Ms) | $k_{off}$ (1/s) | $K_D = k_{off}/k_{on}$ (M) |
| --- | --- | --- | --- |
| murine 763 | 7.82E+04 | 1.63E−04 | 2.09E−09 |
| hu763-IgG1 | 1.03E+05 | 1.81E−04 | 1.75E−09 |
| ch763-IgG1 | 1.79E+05 | 3.39E−04 | 1.89E−09 |

Example 4. Antibody-Dependent Cell-Mediated Cytotoxicity (ADCC) with Humanized 763 Antibodies This Example demonstrates the enhanced ability of humanized 763 antibodies to mediate ADCC via NK cells on target cells. Further, the data described in the present Example illustrates the benefit of humanizing the murine 763 is not solely to reduce immunogenicity.

Mouse 763 antibody is a mouse IgG1, which does not mediate ADCC due to a lack of binding to human Fc receptor. To determine the ADCC potential of humanized 763 antibodies, a CD16-transduced NK92Mi cell line was first generated. This NK92 cell was transduced with both IL-2 and human CD16 (FcγRIIIA), an activating Fc receptor. The human CD16 used contained a high-affinity polymorphism (F158V), which leads to an enhancement in ADCC and clinical response to IgG1-based immunotherapy. ADCC of humanized 763 was evaluated using the NK92Mi cell line described above. The specific lysis of target cells by NK cells activated by humanized 763 antibodies is shown in FIG. 4.

Figure 4A:
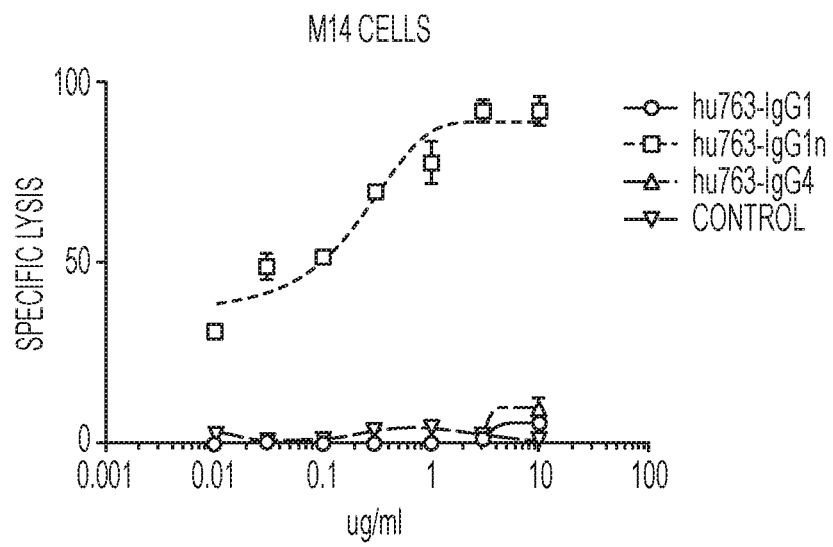
FIG. 4 shows exemplary antibody-dependent cell-mediated cytotoxicity (ADCC) of NK92Mi(CD16) in the presence of humanized 763 antibodies. A, Specific lysis of M14 cells. B, Specific lysis of U2OS cells. E:T ratio was 20:1.
Figure 4B:
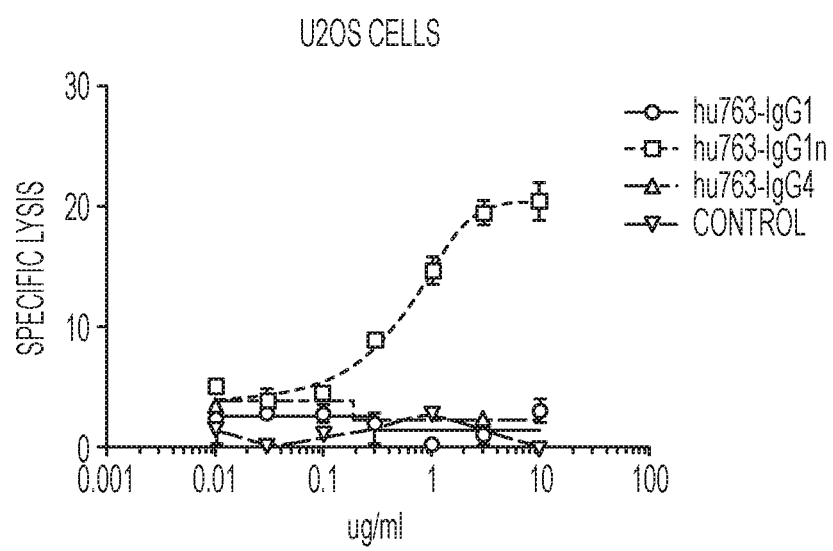

As shown in FIG. 4, only hu763-IgG1n was able to mediated ADCC. $EC_{50}$ for M14 cells was 0.1 μg/mL, while $EC_{50}$ for U2OS cells was 0.65 μg/mL. When toxicity was tested on hepatocytes and cardiac myocytes, neither hu763-IgG4 nor hu763-IgG1n triggered ADCC or CMC in the presence of PBMC or NK92Mi (CD16) cells at antibody concentrations from 1 ng/mL to 10 μg/mL.

Example 5. Biodistribution of Humanized 763 Antibodies in Mice Bearing Tumor Xenografts The humanized 763 antibodies described in the prior Examples were tested for their in vivo efficacy. Biodistribution of radioiodinated antibody in mice implanted with SKMEL-28 tumor cells was determined.

Hu763-IgG1, hu763-IgG4 and hu763-IgG1n were radiolabeled with $^{131}I$ or $^{124}I$. All demonstrated comparable immunoreactivity of ~80-90%. Biodistributions of humanized 763 antibodies at 48 hours were analyzed using mice bearing subcutaneous SKMEL-28 xenografts. Tumor uptake was measured by % ID/gm. Treatment with mouse 763 antibody resulted in 27.4%, hu763-IgG1 in 13.55%, hu763-IgG4 in 10.24%, and hu763-IgG1n in 10.38% (FIG. 5). Tumor to non-tumor ratios were comparable among the tested antibodies.

Example 6. Design, Construction and Expression of Bispecific Antibodies Based on Humanized 763

This Example describes production of bispecific antibodies composed of a first antigen-binding site based on a humanized 763 antibody and a second antigen-binding site that binds to T cells. The data presented herein describes the successful production of bispecific antibodies (termed hu763-BsAbs) to retargeting T cells to melanoma cells. As described herein, an anti-CD3 single chain Fv fragment (ScFv) based on a humanized OKT3 antibody was linked to the carboxyl end of a humanized 763 heavy chain (hu763-HC-OKT3) or linked to the carboxyl end of light chain (hu763-LC-OKT3). A major drawback in the development of T-cell engaging bispecific antibodies has been overstimulation of T cells resulting from CD3 engagement. Such engagement can lead to excessive release of cytokines (known as cytokine storm), which results in serious adverse effects in patients. Therefore, the inventors have introduced an N297A substitution in the Fc region to remove glycosylation and, therefore, eliminating Fc-receptor binding, which also reduces complement activation thereby reducing cytokine storm. As demonstrated below, hu763-BsAbs described herein effectively redirected T cells to lyse CSPG4+ tumor cells in vitro and significantly inhibited tumor growth in murine melanoma xenografts. Such hu763-BsAbs provide both Fc-dependent and T cell-dependent immunotherapeutic possibilities for metastatic tumors such as melanoma.

Figure 6:
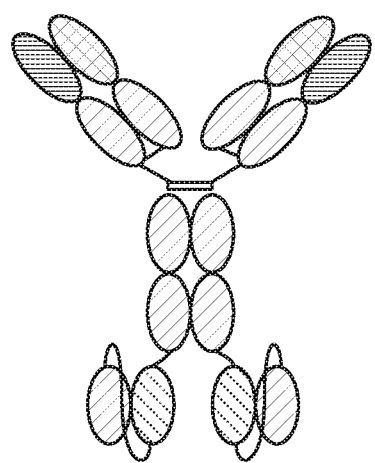
FIG. 6 shows a schematic illustration, not to scale, of humanized bispecific antibody formats (e.g., IgG-scFv) that employ humanized 763 antibodies described herein.
Figure 6:
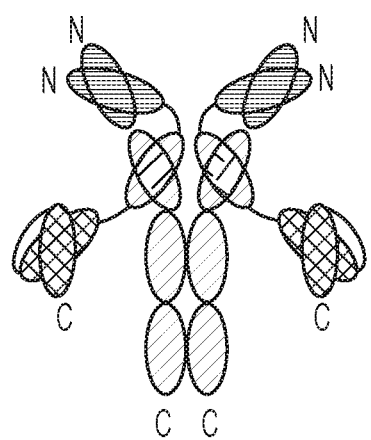

The inventors have designed hu763-BsAbs using the IgG-scFv format set forth in FIG. 6. For the hu763-HC-OKT3 format, the light chain was identical to that of a hu763-IgG1, the heavy chain was constructed by extending a hu763 IgG1 heavy chain with a C-terminal $(G_4S)_3$ linker followed by huOKT3 scFv; for hu763-LC-OKT3 format, the heavy chain was identical to that of a hu763 IgG1, the light chain was constructed by extending a hu763 light chain with a C-terminal $(G_4S)_3$ linker followed by huOKT3 scFv. For both formats, a N297A mutation was introduced to hIgG1 Fc region to remove glycosylation (as described above). The DNA encoding both heavy chain and light chain was inserted into a mammalian expression vector, transfected into CHO-S cells, and stable clones of highest expression were selected. Supernatants were collected from shaker flasks and purified on protein A affinity chromatography. Proteins were further purified to >90% monomer by size exclusion chromatography.

Figure 7A:
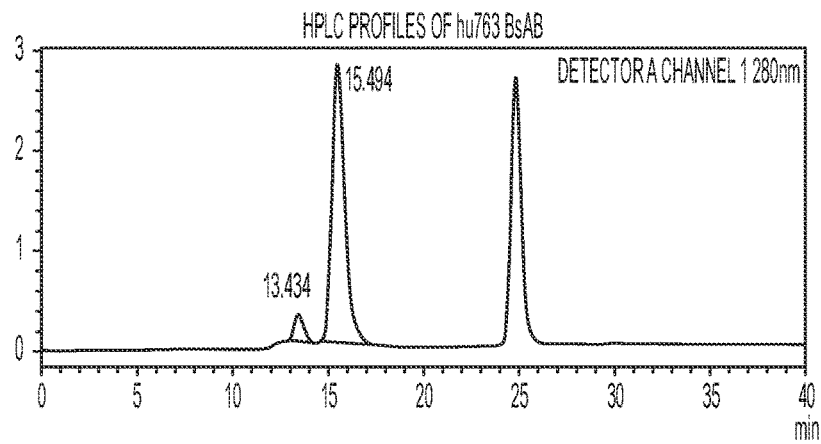
FIG. 7 shows exemplary biochemical analysis of humanized 763 bispecific antibodies (hu763-BsAb) by SE-HPLC chromatography (A) and reduced SDS-PAGE (B). Major peaks for the hu763-HC (15.494 min) and hu763-LC (15.912 min) formats are indicated. Twenty-five minutes is the salt buffer peak.
Figure 7A:
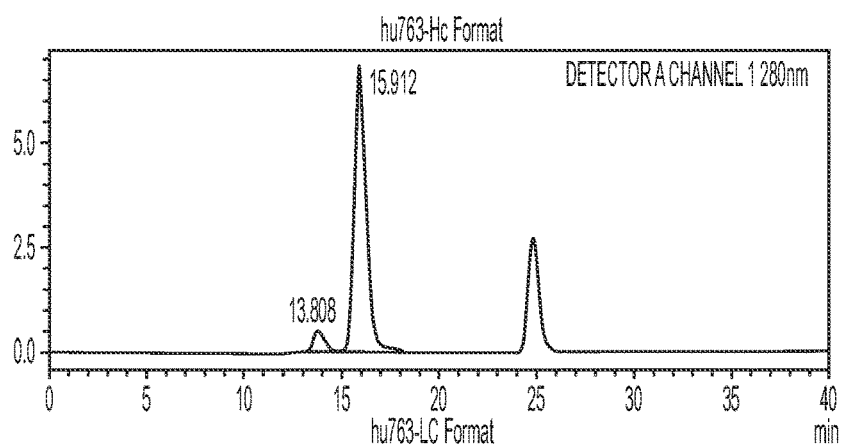
Figure 7B:
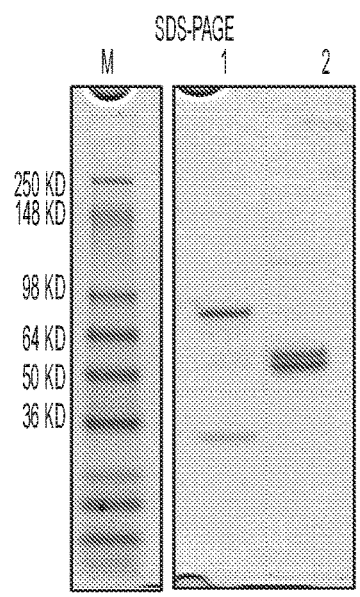

Biochemical purity analysis of the BsAb is shown in FIG. 7. Under reducing SDS-PAGE conditions, Hu763-HC-OKT3 format gave rise to two bands (~75 KDa and ~25 KDa; the huOKT3 scFv fusion to hu763 heavy chain increases the molecular weight to ~75 KDa). Hu763-LC-OKT3 format gave rise to two bands at around 50 KDa (the huOKT3 scFv fusion to hu763 light chain increases the molecular weight to ~50 KDa). SEC-HPLC showed a major peak (97% by UV analysis) with an approximate molecular weight of 210 KDa for both formats, as well as a minor peak of multimers removable by gel filtration.

Example 7. Bispecific Antibodies Based on Humanized 763 Bind to Tumor Cells and T Cells This Example demonstrates bispecific antibodies as described herein are characterized by binding to tumor cells and T cells thereby directing effector T cells to kill target tumor cells. The data presented in this Example confirms that such bispecific antibodies are useful for killing and/or inhibiting the growth of tumor cells.

Figure 8A:
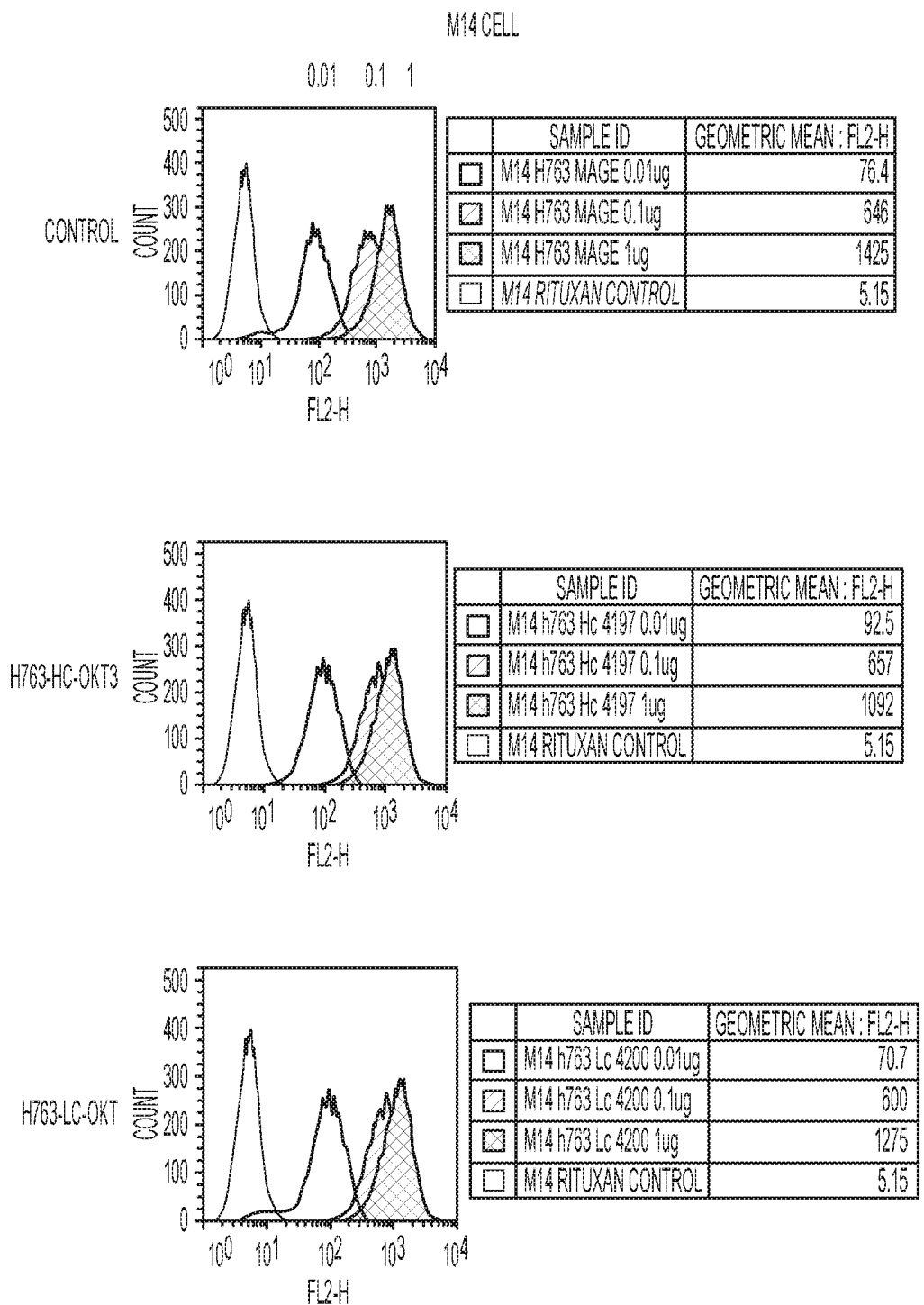
FIG. 8 shows exemplary antigen binding of humanized 763 bispecific antibodies to M14 cells (A) and T cells (B). Control antibody: monospecific antibody that does not bind CSPG4 or T cells. A phycoerythrin conjugated goat anti-human antibody was used as secondary antibody and binding was analyzed by FACS analysis.
Figure 8B:
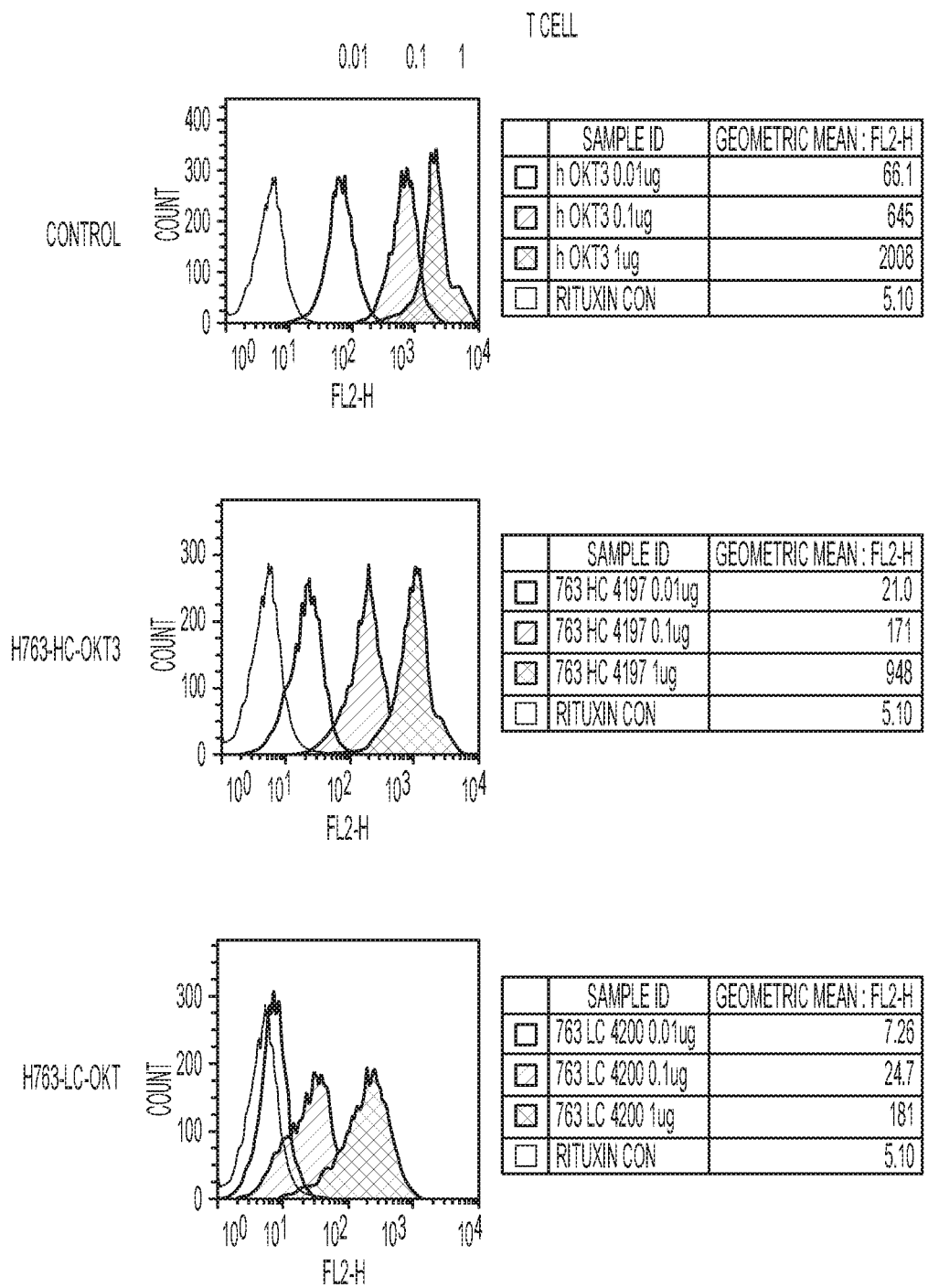

The binding of hu763-BsAbs to both target cells and effector cells was tested by FACS immunostaining. As shown in FIG. 8A, hu763-BsAbs both bound to CSPG4+ breast carcinoma cell M14 as good as parental hu763. Further, as shown in FIG. 8B, hu763-BsAbs bound to CD3+ T cells as well, however, hu763-HC-OKT3 bound slightly worse than humanized OKT3 IgG1 and hu763-LC-OKT3 bound 20-30 fold weaker than parental hu763 or hu763-HC-OKT3. These data are consistent with our observation that light chain anchored scFvs have lower avidity for T cells than regular humanized OKT3 IgG1, which are purposely designed to minimize cytokine release in the absence of target tumor cells.

The lower avidity of hu763-BsAb for T cells was further confirmed by binding affinity analysis by Biacore as previously described (Table 11; Cheung, N. K. et al. (2012) Oncolmmunology 1:477-486; Law, C. L. et al. (2002) Int. Immunol. 14:389-400). For CD3 antigen, hu763-HC-OKT3 had a $k_{on}$ at $3.02 \times 10^5$ $M^{-1}S^{-1}$, a $k_{off}$ at $6.96 \times 10^{-2}$ $s^{-1}$, and overall $K_D$ at 231 nm, which is comparable to parental humanized OKT3 IgG1-aGlyco at $k_{off}$ (1.05×10⁻¹ s⁻¹), but less at $k_m$, (1.71×10⁶ M⁻¹S⁻¹) and overall $K_D$ (61.7 nM). Hu763-LC-OKT3 had a $k_m$, at 1.75×10⁵ M⁻¹S⁻¹, a $k_{off}$ at 9.01×10⁻² s⁻¹, and overall $K_D$ at 515 nm. Taken together, hu763-BsAbs, in particular, hu763-LC-OKT3, had much lower $k_{on}$ than parental humanized OKT3-aGlyco and larger overall $K_D$, which suggests that hu763BsAbs have much lower avidity to binding CD3 and, therefore, are less likely to bind and activate T cells under same conditions. Under these circumstances, hu763BsAbs yield hence less cytokine release and would provide an improved safety benefit to patients.

TABLE 11

CD3 binding of hu763 BsAbs measured by surface plasma resonance

| Two State Reaction | $k_{on}$ (1/Ms) | $k_{off}$ (1/s) | $K_D = k_{off}/k_{on}$ |
|---|---|---|---|
| huOKT3-aGlyco | 1.71E+06 | 1.05E−01 | 6.17E−08 |
| hu763-HC-OKT3 | 3.02E+05 | 6.96E−02 | 2.31E−07 |
| hu763-LC-OKT3 | 1.75E+05 | 9.01E−02 | 5.15E−07 |

Example 8. Humanized 763 Bispecific Antibody-Directed T Cell Killing of Human Tumor Cell Lines This Example demonstrates the enhanced ability of bispecific antibodies based on humanized 763 to initiate tumor cell killing mediated through T cells. Typically, bispecific binding proteins that engage T cells are able to direct T cell to a tumor site for T cell mediated killing of the tumor. In this example, exemplary bispecific antibodies are shown to effectively mediate T cell killing of tumor cells more effectively as compared to control bispecific antibodies.

Figure 9:
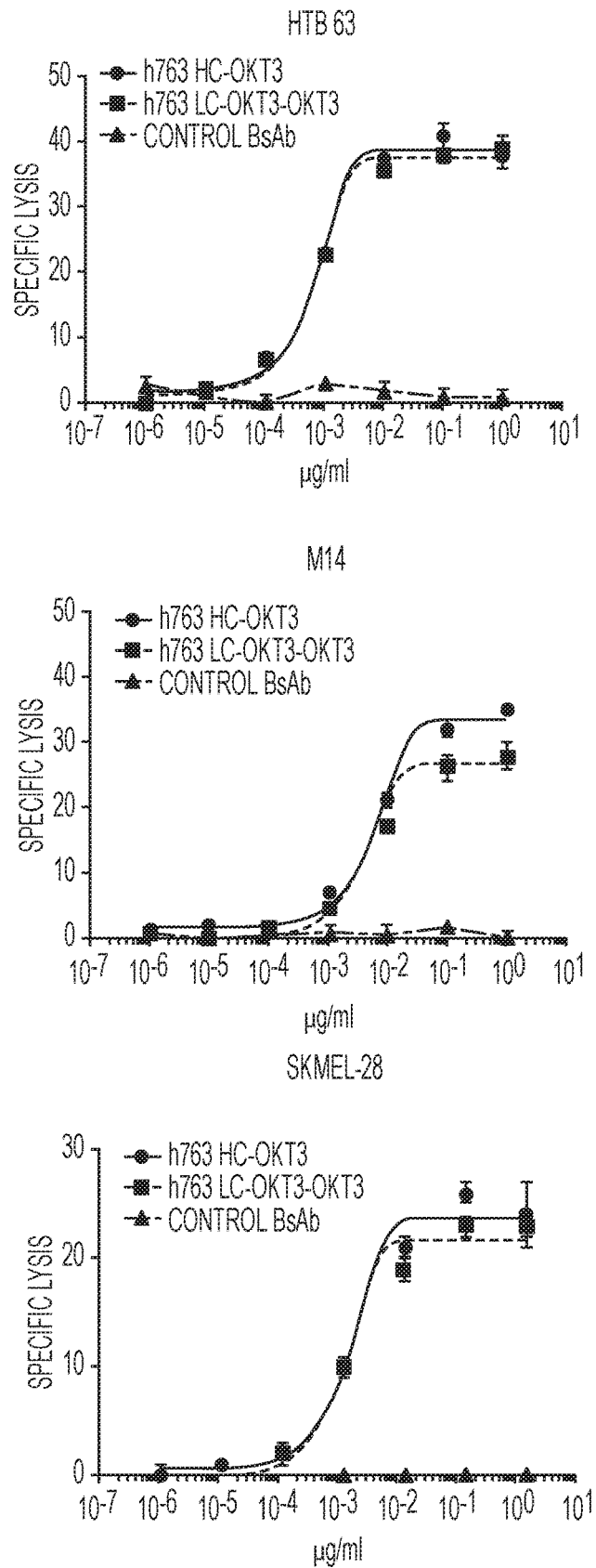
FIG. 9 shows exemplary redirected T cell killing of CSPG4 positive tumor cells by humanized 763 bispecific antibodies. Activated T cells (ATC) were incubated with target cells labeled with $^{51}$Cr (E:T at 10:1) in the presence of different concentration of bispecific antibodies. Cytotoxicity was measured by release of $^{51}$Cr in the supernatant counted by a γ-counter. Control BsAb: control bispecific antibody that binds CSPG4 and an organic compound.

Briefly, to evaluate whether hu763-BsAbs could redirect T cells to kill tumor cells, T cell cytotoxicity on CSPG4⁺ cancer cell lines (M14, HTB-63 and SKMEL-28) was tested in a 4-hour ⁵¹Cr release assay. Exemplary results are presented in FIG. 9.

Compared to a control BsAb (one antigen-binding domain specific to CSPG4 and one antigen-binding domain specific to an organic compound), both hu763-HC-OKT3 and hu763-LC-OKT3 were able to mediated substantial killing of all three types of tumor cells in the presence of T cells.

This Example just confirms, among other things, that bispecific antibodies based on humanized 763 that also bind to T cells can effectively mediate T cell killing of multiple tumor cells that express CSPG4.

Example 9. In Vivo Efficacy of CSPG4 Bispecific Antibodies

This Example illustrates the in vivo efficacy of humanized 763 bispecific antibodies described in the prior Examples.

Briefly, BALB-Rag2-KO-IL-2R-γc-KO mice were used to evaluate the in vivo effect of humanized 763 bispecific antibodies. M14-Luciferase cells were inoculated intravenously to mimic a metastatic model. Treatment with humanized 763 bispecific antibody (hu763-HC-OKT3) was initiated four days post implantation and at two doses per week for a total of two weeks. Effector cells ATC were intravenously administered on day six at one dose (5×10⁶ cells) per week for two weeks. Tumor luciferin bioluminescence signal was recorded and quantified weekly. Exemplary results are presented in FIG. 10.

Figure 10A:
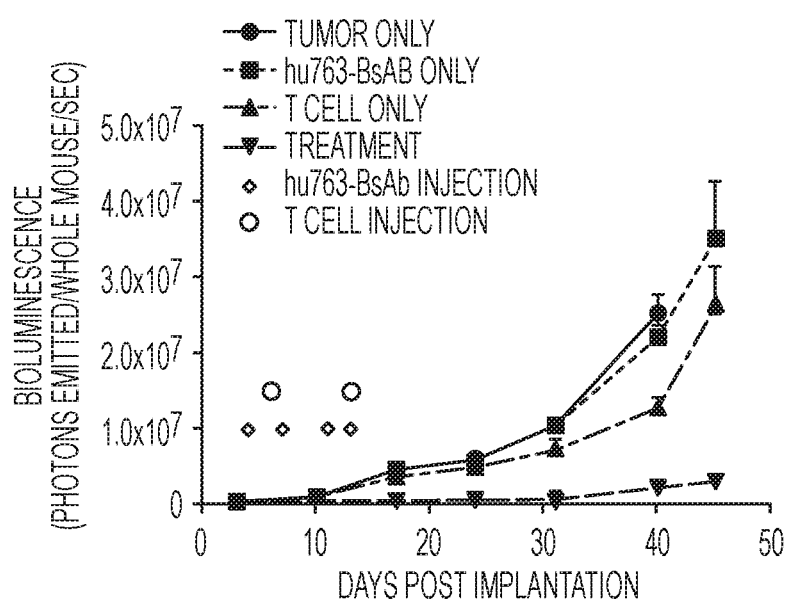
FIG. 10 shows exemplary tumor growths in a melanoma xenograft model using humanized 763 bispecific antibodies. BALBRag2−/−IL-2R-rC-KO (DKO) mice were implanted with 1×10$^6$ M14 (melanoma) cells. Treatment was initiated on day 4 and schedules are indicated (A). Tumor growth was assessed by bioluminescence once a week starting on day 4. A, Bioluminescence quantitation of luciferin for different treatment groups. B, Fluorescent imaging of mice in different treatment groups on day 24.
Figure 10B:
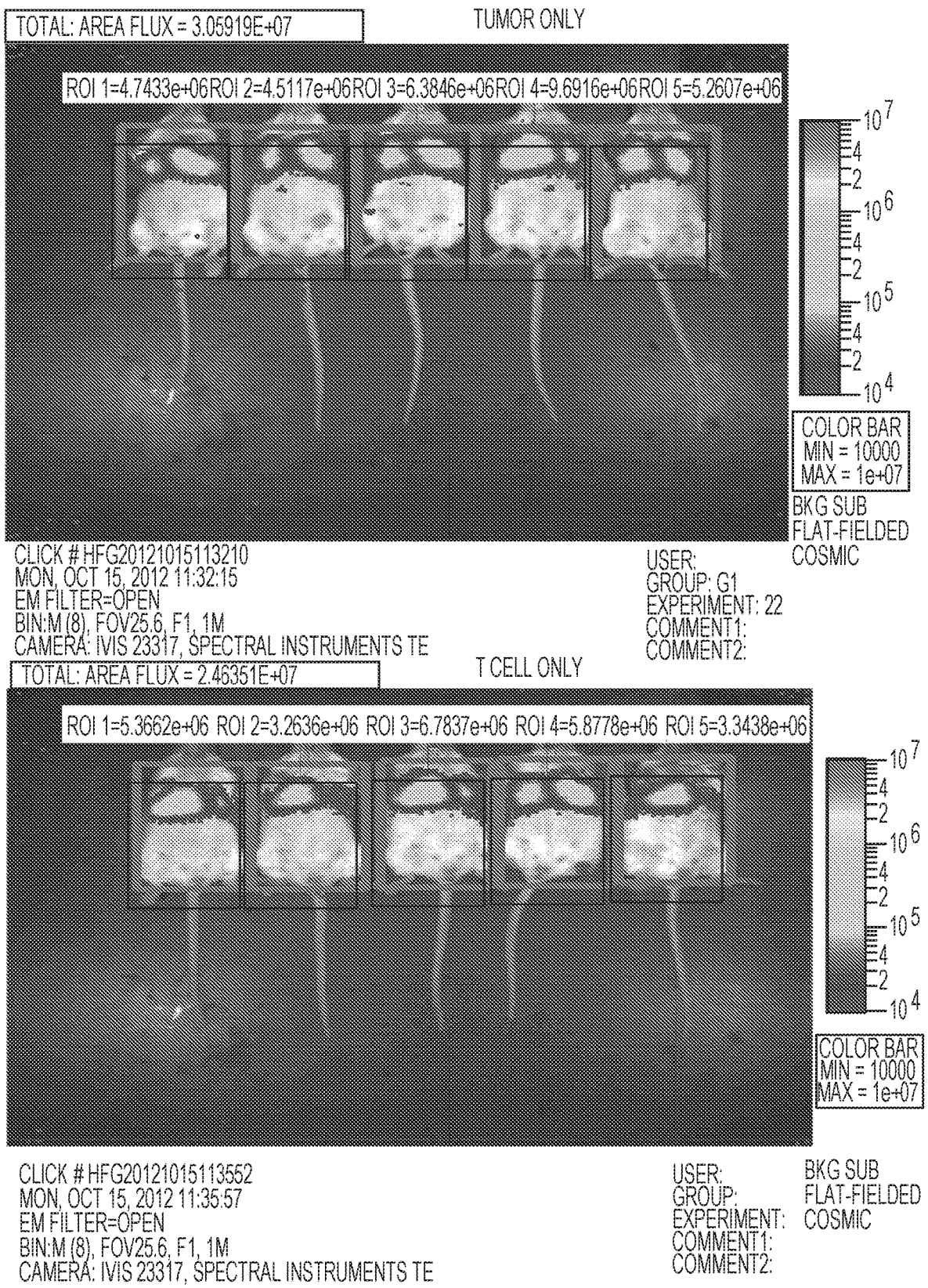
Figure 10B:

As shown in FIG. 10, mice treated with hu763-BsAb alone demonstrated tumor growth equivalent to control treated mice. ATC only (T cell only) had a moderate effect on tumor growth. When ATC and hu763-HC-huOKT3 were combined, substantial suppression of tumor growth was recorded. On day 24, treatment with hu763-HC-huOKT3 demonstrated near complete eradication of tumor cells.

Materials and Methods for Examples

Construction of the Hu763-IgG1, Hu763-IgG4, Hu763-IgG1n Antibody Producer Lines

Based on human homologues of murine 763, CDR sequences of both heavy and light chains of humanized 763 were grafted into the human IgG1 framework and optimized. The humanized 763 genes were synthesized for CHO cells (Blue Heron Biotechnology, Bothhell, Wash. or Genscript, Piscataway, N.Y.). Using the bluescript vector (Eureka, Calif.), the heavy and light chain genes of humanized 763 were transfected into DG44 cells and selected with G418 (Invitrogen, CA). Similarly, human $V_H$ and $V_L$ sequences were grafted onto IgG4 frameworks to make humanized 763-IgG4 recombinant antibodies.

Purification of Humanized 763

Humanized 763 producer lines were cultured in Opticho serum free medium (Invitrogen, CA) and the mature supernatant harvested. Protein A affinity column was preequilibrated with 25 mM sodium citrate buffer with 0.15 M NaCl, pH 8.2. Bound humanized 763 was eluted with 0.1 M citric acid/sodium citrate buffer, pH 3.9 and alkalinized (1:10 v/v ratio) in 25 mM sodium citrate, pH 8.5. It was passed through a Sartobind-Q membrane and concentrated to 5-10 mg/mL in 25 mM sodium citrate, 0.15 M NaCl, pH 8.2. 2 µg each of the proteins was analyzed by SDS-PAGE under non-reducing or reducing conditions using 4-15% Tris-Glycine Ready Gel System (Bio-Rad, Hercules, Calif.). Invitrogen SeeBlue Plus2 Pre-Stained Standard was used as the protein molecular weight marker. After electrophoresis, the gel was stained using PIERCE's GelCode Blue Stain Reagent. The gel was scanned using Bio-Rad Fluor-S Multimager (Bio-Rad), and the band intensity quantified with Quantity One software (Bio-Rad).

Humanized 763 Bispecific Antibody Design, Production, and Purification Analyses

The humanized 763 bispecific antibody format was designed as a humanized OKT3 scFv fusion to the C-terminus of the heavy chain (hu763-Hc-OKT3) or C-terminus of the light chain (hu763-Lc-OKT3) of a humanized 763-IgG1. For the hu763-Hc-OKT3 format, the $V_L$ was identical to that of humanized 763 IgG1, while the heavy chain is constructed as $V_H$-Cκ-(G₄S)₃-(huOKT3) scFv including an N297A mutation in a wild-type IgG1 Fc region. For the hu763-Lc-OKT3 format, the $V_H$ was identical to that of humanized 763 IgG1 except an N297A mutation in a wild-type human IgG1 Fc region, while the light chain is constructed as $V_L$-CK-(G₄S)₃-(huOKT3) scFv. Nucleotide sequences encoding $V_H$ and $V_L$ domains from humanized 763, and the humanized OKT3 scFv were synthesized by GenScript with appropriate flanking restriction enzyme sites, and were subcloned into a standard mammalian expression vector. Linearized plasmid DNA was used to transfect CHO-S cells (Invitrogen) for stable production of bispecific antibody. 2×10⁶ cells were transfected with 5 µg of plasmid DNA by Nucleofection (Lonza) and then recovered in CD OptiCHO medium supplemented with 8 mM L-glutamine (Invitrogen) for two days at 37° C. in 6-well culture plates. Stable pools were selected with 500 µg/mL hygromycin for approximately two weeks and single clones were then selected out with limited dilution. Humanized 763 bispecific antibody titer was determined by CSPG4+ M14 cell and CD3+ Jurkat cell ELISA, respectively, and stable clones with highest expression were selected. The bispecific antibody producer line was cultured in OptiCHO medium and the mature supernatant harvested. A protein A affinity column (GE Healthcare) was pre-equilibrated with 25 mM sodium citrate buffer with 0.15 M NaCl, pH 8.2. Bound bispecific antibody was eluted with 0.1 M citric acid/sodium citrate buffer, pH 3.9 and neutralized with 25 mM sodium citrate, pH 8.5 (1:10 v/v ratio). For storage, bispecific antibody was dialyzed into 25 mM sodium citrate, 0.15 M NaCl, pH 8.2 and frozen in aliquots at −80° C. Two micrograms of the protein was analyzed by SDS-PAGE under reducing conditions using 4-15% Tris-Glycine Ready Gel System (Bio-Rad). The purity of humanized 763 bispecific antibody was also evaluated by size-exclusion high-performance liquid chromatography (SE-HPLC). Approximately 20 µg of protein was injected into a TSK-GEL G3000SWXL 7.8 mm×30 cm, 5 µm column (TOSOH Bioscience) with 0.4 M $NaClO_4$, 0.05 M $NaH_2PO_4$, pH 6.0 buffer at flow rate of 0.5 mL/min, and UV detection at 280 nm. Ten microliters of gel-filtration standard (Bio-Rad) was analyzed in parallel for MW markers.

In Vitro Binding Kinetics by Biacore T-100 Biosensor

CM5 sensor chip (Research grade) and related reagents were purchased from Biacore USA (Piscataway, N.J.). Antigen D2.8.11 or anti-763 idiotype antibody MK2-23 was directly immobilized onto the CM5 sensor chip via hydrophobic interaction. The system first run 20× cycles of buffer only to get stable baseline levels. Purified antibodies (murine 763, humanized 763-IgG1, humanized 763-IgG1n, humanized 763-IgG4) were diluted in HBS-E buffer containing 250 mM NaCl at varying concentrations (41.7~666.7 nM) prior to analysis. Samples (60 µL) were injected over the sensor surface at a flow rate of 30 µL/min over 2 min. Association time was set for one minute; dissociation time was set for from five minutes to 30 minutes. Following completion of the association phase, dissociation was monitored in HBS-E buffer containing 250 mM NaCl at the same flow rate. At the end of each cycle, the surface was regenerated using 50 µL 20 mM NaOH at a flow rate of 50 µL/min over one minute and 100 µL 4M $MgCl_2$ at a flow rate of 50 µL/min over two minutes. The data were analyzed by the bivalent analyte model (for antigen D2.8.11 binding) or monovalent analyte model (for anti-763 idiotype antibody MK2-23 binding) and default parameter setting for the rate constants using the Biacore T-100 (Biacore AB of GE Healthcare, Uppsala, Sweden) evaluation software, and the apparent association on rate constant ($k_{on}$), dissociation off rate constant ($k_{off}$) and equilibrium dissociation constant ($K_D=k_{off}/k_{on}$) were calculated.

FACS Analyses

Cells were incubated with different concentration of primary antibody (humanized 763-IgG1, hu763-Hc-OKT3, hu763-Lc-OKT3 and humanized OKT3) for thirty minutes at 4° C. in PBS, and a secondary phycoerythrin-labeled antibody specific for human Fc was used after wash of excess primary antibody. Cells were fixed with 1% paraformaldehyde (PFA) prior to analysis on FACS Calibur cytometer (BD biosciences). Controls were cells with control human IgG1 antibody (non-specific for CSPG4 or T cells), for which the mean fluorescent intensity (MFI) was set to five.

$^{51}$Chromium Release Assay

For Antibody-Dependent cell-mediated cytotoxicity (ADCC), effector cells were NK-92MI cells stably transfected with human CD16 Fc receptor. E:T ratio was 20:1. For T cell cytotoxicity assay, effector T cells cultured in vitro in the presence of anti-CD3 and anti-CD28 for about 14 days, and used at E:T ratio of 10:1. All target tumor cells were harvested with 2 mM EDTA in PBS, labeled with $^{51}$Cr (Amersham, Arlington Height, Ill.) at 100 µCi/$10^6$ cells at 37° C. for one hour. 5000 target cells/well were mixed with 50,000 effector cells and bispecific antibodies in 96-well polystyrene round-bottom plates (BD Biosciences) to a final volume of 250 µL/well. The plates were incubated at 37° C. for four hours. The released $^{51}$Cr in supernatant was counted in a γ-counter (Packed Instrument, Downers Grove, Ill.). Percentage of specific release was calculated using the formula: (experimental cpm−background cpm)/(total cpm−background cpm)×100%, where cpm represented counts per minute of $^{51}$Cr released. Total release was assessed by lysis with 10% SDS (Sigma, St Louis, Mo.), and background release was measured in the absence of effector cells. EC50 was calculated using Sigmaplot software.

Immunohistochemistry (IHC)

Stage 4 melanoma tumors and normal tissues were obtained at Memorial Sloan-Kettering Cancer Center with institutional review board approval. Five- to seven-micrometer sections of snap-frozen tissues were fixed in acetone for 30 min at −20° C. Endogenous biotin-binding activity was blocked by sequential treatment with avidin and biotin (Vector avidin-biotin blocking kit; Invitrogen) for 20 minutes each followed by blocked with 10% horse serum for one hour at room temperature. Sections were then sequentially reacted with primary antibody, biotinylated horse anti-mouse IgG (H+L) (Vector Laboratories) and Avidin-Biotin Complex (Vectastain ABC kit) for 60 minutes respectively at room temperature, and washed between each reaction. Subsequently, sections were stained with dye (DAB Peroxidase substrate kit) for two minutes, washed, counterstained with Myer's hematoxylin, washed, dehydrated in 95% ethyl alcohol.

Animals and In Vivo Assays

For in vivo studies, BALB-Rag2-KO-IL-2R-γc-KO (DKO) mice (derived from colony of Dr. Mamoru Ito, CIEA, Kawasaki, Japan; Koo G C, et al. (2009) Expert Rev. Vaccines 8:113-120; Andrade, D. et al. (2011) Arthritis Rheum. 63:2764-2773; Cheng, M. et al. (2014) Int. J. Cancer). M14 cells expressing luciferase were administered to DKO mice intravenously. Four days post administration, mice were treated with 20 µg of hu763-Hc-OKT3 with intravenous administration ATC for 1×$10^6$. Tumor growth was assessed by luciferin bioluminescence once a week. Bioluminescence imaging was conducted using the Xenogen In Vivo Imaging System (IVIS) 200 (Caliper LifeSciences). Briefly, mice were injected intravenously with 0.1 mL solution of D-luciferin (Gold Biotechnology, 30 mg/mL stock in PBS). Images were collected 1-2 min post injection using the following parameters: a 10-60 seconds exposure time, medium binning, and an 8 f/stop. Bioluminescence image analysis was performed using Living Image 2.6 (Caliper LifeSciences).

Antibody Biodistribution in Xenografted Mice

Female athymic nude mice were purchased from Harlan Sprague Dawley, Inc. All procedures were carried out in accordance with the protocols approved by the Memorial Sloan-Kettering Cancer Center Institutional Animal Care and Use Committee and institutional guidelines for the proper and humane use of animals in research. SKME1-28 tumor cells were harvested and resuspended in Matrigel (BD Biosciences). Cells (2~10×10$^6$) were implanted subcutaneously (sc) to the flank of the mice in 0.1 mL volume using 22-gauge needles. Tumors were allowed to grow to the size of ~200 mm$^3$ before initiating treatment. Mice with established tumors were randomly separated into treatment groups. 100 µCi of radioiodinated antibody per mouse was injected intravenously and animals sacrificed usually at 48 hours, and their organs removed and counted in a gamma counter (Packard Instruments, Perkin Elmer). These organs included skin, liver, spleen, kidney, adrenal, stomach, small intestine, large intestine, bladder, femur, muscle, tumor, heart, lung, spine, and brain. Based on the µCi accumulated in the organ and the organ weight, % injected dose (ID)/gm of mouse was calculated. Tumor to non-tumor ratios of % ID/gm was also calculated.

Having thus described several aspects of at least one embodiment of this invention, it is to be appreciated that various alterations, modifications, and improvements will readily be apparent to those skilled in the art. Such alterations, modifications, and improvements are intended to be part of this disclosure, and are intended to be within the spirit and scope of the invention. Accordingly, the foregoing description and drawings are by way of example only and the invention is described in detail by the claims that follow.

EQUIVALENTS

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The publications, websites and other reference materials referenced herein to describe the background of the invention and to provide additional detail regarding its practice are hereby incorporated by reference.

REFERENCES

Andrade D, Redecha P B, Vukelic M, et al. (2011) Engraftment of peripheral blood mononuclear cells from systemic lupus erythematosus and anti-phospholipid syndrome patient donors into BALB-RAG-2−/− IL-2Rgamma−/− mice: a promising model for studying human disease. Arthritis Rheum. 63:2764-2673.

Barritt D S, Pearn M T, Zisch A H, et al. (2000) The multi-PDZ domain protein MUPP1 is a cytoplasmic ligand for the membrane-spanning proteoglycan NG2. J. Cell Biochem. 79:213-224.

Bluemel C, Hausmann S, Fluhr P, et al. (2010) Epitope distance to the target cell membrane and antigen size determine the potency of T cell-mediated lysis by BiTE antibodies specific for a large melanoma surface antigen. Cancer Immunol. Immunother. 59:1197-1209.

Bradbury E J, Moon L D, Popat R J, et al. (2002) Chondroitinase ABC promotes functional recovery after spinal cord injury. Nature 416:636-640.

Bruland O S, Hoifodt H, Saeter G, et al. (2005) Hematogenous micrometastases in osteosarcoma patients. Clin. Cancer Res. 11:4666-4673.

Burns W R, Zhao Y, Frankel T L, et al. (2010) A high molecular weight melanoma associated antigen-specific chimeric antigen receptor redirects lymphocytes to target human melanomas. Cancer Res. 70:3027-3033.

Campoli M R, Chang C C, Kageshita T, et al. (2004) Human high molecular weight-melanoma-associated antigen (HMW-MAA): a melanoma cell surface chondroitin sulfate proteoglycan (MSCP) with biological and clinical significance. Crit. Rev. Immunol. 24:267-296.

Campoli M, Ferrone S, Wang X (2010) Functional and clinical relevance of chondroitin sulfate proteoglycan 4. Adv. Cancer. Res. 109:73-121.

Chang C C, Campoli M, Luo W, et al. (2004) Immunotherapy of melanoma targeting human high molecular weight melanoma-associated antigen: potential role of nonimmunological mechanisms. Ann. N. Y. Acad. Sci. 1028:340-350.

Chatterjee N, Stegmuller J, Schatzle P, et al. (2008) Interaction of syntenin-1 and the NG2 proteoglycan in migratory oligodendrocyte precursor cells. J. Biol. Chem. 283:8310-8317.

Cheng M, Ahmed M, Xu H, et al. (2014) Structural design of disialoganglioside GD2 and CD3-bispecific antibodies to redirect T cells for tumor therapy. Int. J. Cancer.

Cheung N K, Lazarus H, Miraldi F D, et al. (1987) Ganglioside GD2 specific monoclonal antibody 3F8: a phase I study in patients with neuroblastoma and malignant melanoma. J. Clin. Oncol. 5:1430-1440.

Cheung N K, Guo H, Hu J, et al. (2012) Humanizing murine IgG3 anti-GD2 antibody m3F8 substantially improves antibody-dependent cell-mediated cytotoxicity while retaining targeting in vivo. OncoImmunol. 1:477-486.

Del Vecchio S, Reynolds J C, Carrasquillo J A, et al. (1989) Local distribution and concentration of intravenously injected 131I-9.2.27 monoclonal antibody in human malignant melanoma. Cancer Res. 49:2783-2789.

Eisenmann K M, McCarthy J B, Simpson M A, et al. (1999) Melanoma chondroitin sulphate proteoglycan regulates cell spreading through Cdc42, Ack-1 and p130cas. Nat. Cell Biol. 1:507-513.

Geiser M, Schultz D, Le Cardinal A, et al. (1999) Identification of the human melanoma-associated chondroitin sulfate proteoglycan antigen epitope recognized by the antitumor monoclonal antibody 763.74 from a peptide phage library. Cancer Res. 59:905-910.

Geldres C, Savoldo B, Hoyos V, et al. (2014) T lymphocytes redirected against the chondroitin sulfate proteoglycan-4 control the growth of multiple solid tumors both in vitro and in vivo. Clin. Cancer Res. 20:962-971.

Godal A, Kumle B, Pihl A, et al. (1992) Immunotoxins directed against the high molecular-weight melanoma-associated antigen. Identification of potent antibody-toxin combinations. Int. J. Cancer 52:631-635.

Houghton A N, Mintzer D, Cordon-Cardo C, et al. (1985) Mouse monoclonal IgG3 antibody detecting GD3 ganglioside: a phase I trial in patients with malignant melanoma. Proc. Natl. Acad. Sci. U.S.A. 82:1242-1246.

Hwang K M, Fodstad O, Oldham R K, et al. (1985) Radiolocalization of xenografted human malignant melanoma by a monoclonal antibody (9.2.27) to a melanoma-associated antigen in nude mice. Cancer Res. 45:4150-4155.

Idusogie E E, Presta L G, Gazzano-Santoro H, et al. (2000) Mapping of the Clq binding site on rituxan, a chimeric antibody with a human IgG1 Fc. J. Immunol. 164:4178-4184.

Iida J, Pei D, Kang T, et al. (2001) Melanoma chondroitin sulfate proteoglycan regulates matrix metalloproteinase-dependent human melanoma invasion into type I collagen. J. Biol. Chem. 276:18786-18794.

Jefferis R (2009) Glycosylation as a strategy to improve antibody-based therapeutics. Nat. Rev. Drug Discov. 8:226-234.

Kantor R R, Ng A K, Giacomini P, et al. (1982) Analysis of the NIH workshop monoclonal antibodies to human melanoma antigens. Hybridoma 1:473-82.

Kirsch M, Schackert G, Black P M (2004) Metastasis and angiogenesis. Cancer Treat. Res. 117:285-304.

Koo G C, Hasan A, O'Reilly R J (2009) Use of humanized severe combined immunodeficient mice for human vaccine development. Expert Rev. Vaccines 8:113-120.

Kusama M, Kageshita T, Chen Z J, et al. (1989) Characterization of syngeneic anti-idiotypic monoclonal antibodies to murine anti-human high molecular weight melanoma-associated antigen monoclonal antibodies. J. Immunol. 143:3844-3852.

Law C L, Hayden-Ledbetter M, Buckwalter S, et al. (2002) Expression and characterization of recombinant soluble human CD3 molecules: presentation of antigenic epitopes defined on the native TCR-CD3 complex. Int. Immunol. 14:389-400.

Luo W, Hsu J C, Tsao C Y, et al. (2005) Differential immunogenicity of two peptides isolated by high molecular weight-melanoma-associated antigen-specific monoclonal antibodies with different affinities. J. Immunol. 174:7104-7110.

Mayayo S L, Prestigio S, Maniscalco L, et al (2011) Chondroitin sulfate proteoglycan-4: a biomarker and a potential immunotherapeutic target for canine malignant melanoma. Vet. J. 190:e26-30.

Meier F, Busch S, Gast D, et al. (2006) The adhesion molecule L1 (CD171) promotes melanoma progression. Int. J. Cancer 119:549-555.

Mittelman A, Chen Z J, Yang H, et al. (1992) Human high molecular weight melanoma-associated antigen (HMW-MAA) mimicry by mouse anti-idiotypic monoclonal antibody MK2-23: Induction of humoral anti-HMW-MAA immunity and prolongation of survival in patients with stage IV melanoma. Proc. Natl. Acad. Sci. U.S.A 89:466-470.

Mittelman A, Chen Z J, Liu C C, et al. (1994) Kinetics of the immune response and regression of metastatic lesions following development of humoral anti-high molecular weight-melanoma associated antigen immunity in three patients with advanced malignant melanoma immunized with mouse anti-idiotypic monoclonal antibody MK2-23. Cancer Res. 54:415-421.

Mittelman A, Chen G Z, Wong G Y, et al. (1995) Human high molecular weight melanoma associated antigen mimicry by mouse anti-idiotypic monoclonal antibody MK2-23: modulation of the immunogenicity in patients with malignant melanoma. Clin. Cancer Res. 1:705-713.

Mittelman A, Tiwari R, Lucchese G, et al. (2004) Identification of monoclonal anti-HMW-MAA antibody linear peptide epitope by proteomic database mining. J. Invest. Dermatol. 123:670-675.

Natali P G, Bigotti A, Nicotra M R, et al. (1989) Analysis of the antigenic profile of uveal melanoma lesions with anti-cutaneous melanoma-associated antigen and anti-HLA monoclonal antibodies. Cancer Res. 49:1269-1274.

Novak-Hofer I (2007) The L1 cell adhesion molecule as a target for radioimmunotherapy. Cancer Biother. Radiopharm. 22:175-184.

Oldham R K, Foon K A, Morgan A C, et al. (1984) Monoclonal antibody therapy of malignant melanoma: in vivo localization in cutaneous metastasis after intravenous administration. J. Clin. Oncol. 2:1235-1244.

Raja C, Graham P, Abbas Rizvi S M, et al. (2007) Interim analysis of toxicity and response in phase 1 trial of systemic targeted alpha therapy for metastatic melanoma. Cancer Biol. Ther. 6:846-852.

Reinhold U, Liu L, Ludtke-Handjery H-C, et al. (1999) Specific lysis of melanoma cells by receptor grafted T cells is enhanced by anti-idiotypic monoclonal antibodies directed to scFv domain of the receptor. J. of Invest. Dermatol. 112:744-750.

Riccardo F, Iussich S, Maniscalco L, et al. (2014) CSPG4-Specific Immunity and Survival Prolongation in Dogs with Oral Malignant Melanoma Immunized with Human CSPG4 DNA. Clin. Cancer Res. 20:3753-3762.

Rivera Z, Ferrone S, Wang X, et al. (2012) CSPG4 as a target of antibody-based immunotherapy for malignant mesothelioma. Clin. Cancer Res. 18:5352-5363.

Stallcup W B, Huang F J. (2008) A role for the NG2 proteoglycan in glioma progression. Cell Adh. Migr. 2:192-201.

Stegmuller J, Schneider S, Hellwig A, et al. (2002) AN2, the mouse homologue of NG2, is a surface antigen on glial precursor cells implicated in control of cell migration. J. Neurocytol. 31:497-505.

Torisu-Itakura H, Schoellhammer H F, Sim M S, et al. (2011) Redirected lysis of human melanoma cells by a MCSP/CD3-bispecific BiTE antibody that engages patient-derived T cells. J. Immunother. 34:597-605.

Wagner S, Hafner C, Allwardt D, et al. (2005) Vaccination with a human high molecular weight melanoma-associated antigen mimotope induces a humoral response inhibiting melanoma cell growth in vitro. J. Immunol. 174: 976-982.

Wang X, Osada T, Wang Y, et al. (2010) CSPG4 protein as a new target for the antibody-based immunotherapy of triple-negative breast cancer. J. Natl. Cancer Inst. 102: 1496-1512.

Wang X, Wang Y, Yu L, et al. (2010) CSPG4 in cancer: multiple roles. Curr. Mol. Med. 10:419-429.

Wang X, Katayama A, Wang Y, et al. (2011) Functional characterization of an scFv-Fc antibody that immuno-therapeutically targets the common cancer cell surface proteoglycan CSPG4. Cancer Res. 71:7410-7422.

Weinstein J N, van Osdol W (1992) Early intervention in cancer using monoclonal antibodies and other biological ligands: micropharmacology and the "binding site barrier". Cancer Res. 52:2747s-2751s.

Yang J, Price M A, Neudauer C L, et al. (2004) Melanoma chondroitin sulfate proteoglycan enhances FAK and ERK activation by distinct mechanisms. J. Cell Biol. 165:881-891.

---

We claim:

1. A bispecific binding agent comprising an immunoglobulin that binds chondroitin sulfate proteoglycan 4 (CSPG4) and two scFvs that each bind a second antigen, wherein the immunoglobulin is a humanized anti-CSPG4 antibody comprising two heavy chains and two light chains, wherein:

each heavy chain comprises a humanized heavy chain variable region sequence as set forth in SEQ ID NO: 8 or 10, and each light chain comprises a humanized light chain variable region sequence as set forth in SEQ ID NO. 12 or 14, and wherein a scFv that binds the second antigen is linked to the C-terminal end of each of the two light chains of the humanized anti-CSPG4 antibody.

2. The bispecific binding agent of claim 1, wherein the immunoglobulin that binds CSPG4 is glycosylated with terminal mannose, N-acetylglucose or glucose, but no fucose.

3. The bispecific binding agent of claim 1, wherein the immunoglobulin that binds CSPG4 comprises a human IgG1 or a human IgG4.

4. The bispecific binding agent of claim 3, wherein the immunoglobulin that binds CSPG4 comprises a human IgG1 that has a variant glycosylation.

5. The bispecific binding agent of claim 4, wherein the variant glycosylation results from an amino acid substitution at residue 297 of the human IgG1 Fc.

6. A composition comprising the bispecific binding agent of claim 1.

7. The composition of claim 6, wherein the bispecific binding agent is conjugated to a cytotoxic agent.

8. A pharmaceutical composition comprising the composition of claim 6 comprising the bispecific binding agent, and further comprising a pharmaceutically acceptable carrier or diluent.

9. The bispecific binding agent of claim 1, wherein the a humanized light chain variable region of the humanized anti-CSPG4 antibody comprises a sequence as set forth in SEQ ID NO: 12, and wherein the humanized heavy chain variable region of the humanized anti-CSPG4 antibody comprises a sequence as set forth in SEQ ID NO: 8.

10. The bispecific binding agent of claim 1, wherein the two heavy chains of the humanized anti-CSPG4 antibody each comprise a sequence as set forth in SEQ ID NO: 8 and the two light chains of the humanized anti-CSPG4 antibody each comprise a sequence as set forth in SEQ ID NO: 12.

11. The bispecific binding agent of claim 1, wherein the humanized light chain variable region of the humanized anti-CSPG4 antibody comprises a sequence as set forth in SEQ ID NO: 14, and wherein the humanized heavy chain variable region of the humanized anti-CSPG4 antibody comprises a sequence as set forth in SEQ ID NO: 10.

12. The bispecific binding agent of claim 1, wherein the two heavy chains of the humanized anti-CSPG4 antibody each comprise a sequence as set forth in SEQ ID NO: 10 and the two light chains of the humanized anti-CSPG4 antibody each comprise a sequence as set forth in SEQ ID NO: 14.

13. The bispecific antibody of claim 1, wherein the second antigen-binding site binds an immune cell selected from the group consisting of a T cell, NK cell, B cell, dendritic cell, monocyte, macrophage, neutrophil, mesenchymal stem cell and neural stem cell.

14. The bispecific antibody of claim 1, wherein the second antigen-binding site binds CD3.

15. The bispecific antibody of claim 14, wherein the bispecific antibody comprises the sequence of SEQ ID NO: 22.

16. An isolated nucleic acid molecule that encodes a bispecific binding agent of claim 1.

17. The isolated nucleic acid molecule of claim 16, wherein the coding sequence is codon-optimized.

18. A recombinant vector comprising the nucleic acid molecule of claim 16.

19. A host cell comprising the recombinant vector of claim 18.

20. A method for producing a bispecific binding agent comprising: culturing the host cell according to claim 19 in a culture medium under conditions allowing the expression of the bispecific binding agent and separating the bispecific binding agent from the culture medium.

\* \* \* \* \*

SEQUENCE LISTING

```
<160> NUMBER OF SEQ ID NOS: 23

<210> SEQ ID NO 1
<211> LENGTH: 2322
<212> TYPE: PRT
<213> ORGANISM: Homo sapiens

<400> SEQUENCE: 1

Met Gln Ser Gly Pro Arg Pro Leu Pro Ala Pro Gly Leu Ala Leu
1               5                   10                  15

Ala Leu Thr Leu Thr Met Leu Ala Arg Leu Ala Ser Ala Ala Ser Phe
                20                  25                  30

Phe Gly Glu Asn His Leu Glu Val Pro Val Ala Thr Ala Leu Thr Asp
            35                  40                  45

Ile Asp Leu Gln Leu Gln Phe Ser Thr Ser Gln Pro Glu Ala Leu Leu
    50                  55                  60

Leu Leu Ala Ala Gly Pro Ala Asp His Leu Leu Leu Gln Leu Tyr Ser
65                  70                  75                  80

Gly Arg Leu Gln Val Arg Leu Val Leu Gly Gln Glu Glu Leu Arg Leu
                85                  90                  95

Gln Thr Pro Ala Glu Thr Leu Leu Ser Asp Ser Ile Pro His Thr Val
            100                 105                 110

Val Leu Thr Val Val Glu Gly Trp Ala Thr Leu Ser Val Asp Gly Phe
        115                 120                 125

Leu Asn Ala Ser Ser Ala Val Pro Gly Ala Pro Leu Glu Val Pro Tyr
    130                 135                 140

Gly Leu Phe Val Gly Gly Thr Gly Thr Leu Gly Leu Pro Tyr Leu Arg
145                 150                 155                 160

Gly Thr Ser Arg Pro Leu Arg Gly Cys Leu His Ala Ala Thr Leu Asn
                165                 170                 175

Gly Arg Ser Leu Leu Arg Pro Leu Thr Pro Asp Val His Glu Gly Cys
            180                 185                 190

Ala Glu Glu Phe Ser Ala Ser Asp Asp Val Ala Leu Gly Phe Ser Gly
        195                 200                 205

Pro His Ser Leu Ala Ala Phe Pro Ala Trp Gly Thr Gln Asp Glu Gly
    210                 215                 220

Thr Leu Glu Phe Thr Leu Thr Thr Gln Ser Arg Gln Ala Pro Leu Ala
225                 230                 235                 240

Phe Gln Ala Gly Gly Arg Arg Gly Asp Phe Ile Tyr Val Asp Ile Phe
                245                 250                 255

Glu Gly His Leu Arg Ala Val Val Glu Lys Gly Gln Gly Thr Val Leu
            260                 265                 270

Leu His Asn Ser Val Pro Val Ala Asp Gly Gln Pro His Glu Val Ser
        275                 280                 285

Val His Ile Asn Ala His Arg Leu Glu Ile Ser Val Asp Gln Tyr Pro
```

```
            290                 295                 300
Thr His Thr Ser Asn Arg Gly Val Leu Ser Tyr Leu Glu Pro Arg Gly
305                 310                 315                 320

Ser Leu Leu Leu Gly Gly Leu Asp Ala Glu Ala Ser Arg His Leu Gln
                325                 330                 335

Glu His Arg Leu Gly Leu Thr Pro Glu Ala Thr Asn Ala Ser Leu Leu
                340                 345                 350

Gly Cys Met Glu Asp Leu Ser Val Asn Gly Gln Arg Arg Gly Leu Arg
            355                 360                 365

Glu Ala Leu Leu Thr Arg Asn Met Ala Ala Gly Cys Arg Leu Glu Glu
            370                 375                 380

Glu Glu Tyr Glu Asp Asp Ala Tyr Gly His Tyr Glu Ala Phe Ser Thr
385                 390                 395                 400

Leu Ala Pro Glu Ala Trp Pro Ala Met Glu Leu Pro Glu Pro Cys Val
                405                 410                 415

Pro Glu Pro Gly Leu Pro Pro Val Phe Ala Asn Phe Thr Gln Leu Leu
                420                 425                 430

Thr Ile Ser Pro Leu Val Val Ala Glu Gly Gly Thr Ala Trp Leu Glu
            435                 440                 445

Trp Arg His Val Gln Pro Thr Leu Asp Leu Met Glu Ala Glu Leu Arg
            450                 455                 460

Lys Ser Gln Val Leu Phe Ser Val Thr Arg Gly Ala Arg His Gly Glu
465                 470                 475                 480

Leu Glu Leu Asp Ile Pro Gly Ala Gln Ala Arg Lys Met Phe Thr Leu
                485                 490                 495

Leu Asp Val Val Asn Arg Lys Ala Arg Phe Ile His Asp Gly Ser Glu
                500                 505                 510

Asp Thr Ser Asp Gln Leu Val Leu Glu Val Ser Val Thr Ala Arg Val
            515                 520                 525

Pro Met Pro Ser Cys Leu Arg Arg Gly Gln Thr Tyr Leu Leu Pro Ile
            530                 535                 540

Gln Val Asn Pro Val Asn Asp Pro Pro His Ile Ile Phe Pro His Gly
545                 550                 555                 560

Ser Leu Met Val Ile Leu Glu His Thr Gln Lys Pro Leu Gly Pro Glu
                565                 570                 575

Val Phe Gln Ala Tyr Asp Pro Asp Ser Ala Cys Glu Gly Leu Thr Phe
                580                 585                 590

Gln Val Leu Gly Thr Ser Ser Gly Leu Pro Val Glu Arg Arg Asp Gln
            595                 600                 605

Pro Gly Glu Pro Ala Thr Glu Phe Ser Cys Arg Glu Leu Glu Ala Gly
            610                 615                 620

Ser Leu Val Tyr Val His Arg Gly Gly Pro Ala Gln Asp Leu Thr Phe
625                 630                 635                 640

Arg Val Ser Asp Gly Leu Gln Ala Ser Pro Pro Ala Thr Leu Lys Val
                645                 650                 655

Val Ala Ile Arg Pro Ala Ile Gln Ile His Arg Ser Thr Gly Leu Arg
                660                 665                 670

Leu Ala Gln Gly Ser Ala Met Pro Ile Leu Pro Ala Asn Leu Ser Val
            675                 680                 685

Glu Thr Asn Ala Val Gly Gln Asp Val Ser Val Leu Phe Arg Val Thr
            690                 695                 700

Gly Ala Leu Gln Phe Gly Glu Leu Gln Lys Gln Gly Ala Gly Gly Val
705                 710                 715                 720
```

```
Glu Gly Ala Glu Trp Trp Ala Thr Gln Ala Phe His Gln Arg Asp Val
            725                 730                 735

Glu Gln Gly Arg Val Arg Tyr Leu Ser Thr Asp Pro Gln His His Ala
            740                 745                 750

Tyr Asp Thr Val Glu Asn Leu Ala Leu Glu Val Gln Val Gly Gln Glu
            755                 760                 765

Ile Leu Ser Asn Leu Ser Phe Pro Val Thr Ile Gln Arg Ala Thr Val
770                 775                 780

Trp Met Leu Arg Leu Glu Pro Leu His Thr Gln Asn Thr Gln Gln Glu
785                 790                 795                 800

Thr Leu Thr Thr Ala His Leu Glu Ala Thr Leu Glu Glu Ala Gly Pro
            805                 810                 815

Ser Pro Pro Thr Phe His Tyr Glu Val Val Gln Ala Pro Arg Lys Gly
            820                 825                 830

Asn Leu Gln Leu Gln Gly Thr Arg Leu Ser Asp Gly Gln Gly Phe Thr
            835                 840                 845

Gln Asp Asp Ile Gln Ala Gly Arg Val Thr Tyr Gly Ala Thr Ala Arg
850                 855                 860

Ala Ser Glu Ala Val Glu Asp Thr Phe Arg Phe Arg Val Thr Ala Pro
865                 870                 875                 880

Pro Tyr Phe Ser Pro Leu Tyr Thr Phe Pro Ile His Ile Gly Gly Asp
            885                 890                 895

Pro Asp Ala Pro Val Leu Thr Asn Val Leu Leu Val Val Pro Glu Gly
            900                 905                 910

Gly Glu Gly Val Leu Ser Ala Asp His Leu Phe Val Lys Ser Leu Asn
            915                 920                 925

Ser Ala Ser Tyr Leu Tyr Glu Val Met Glu Arg Pro Arg His Gly Arg
930                 935                 940

Leu Ala Trp Arg Gly Thr Gln Asp Lys Thr Thr Met Val Thr Ser Phe
945                 950                 955                 960

Thr Asn Glu Asp Leu Leu Arg Gly Arg Leu Val Tyr Gln His Asp Asp
            965                 970                 975

Ser Glu Thr Thr Glu Asp Asp Ile Pro Phe Val Ala Thr Arg Gln Gly
            980                 985                 990

Glu Ser Ser Gly Asp Met Ala Trp Glu Glu Val Arg Gly Val Phe Arg
            995                 1000                1005

Val Ala Ile Gln Pro Val Asn Asp His Ala Pro Val Gln Thr Ile
            1010                1015                1020

Ser Arg Ile Phe His Val Ala Arg Gly Gly Arg Arg Leu Leu Thr
            1025                1030                1035

Thr Asp Asp Val Ala Phe Ser Asp Ala Asp Ser Gly Phe Ala Asp
            1040                1045                1050

Ala Gln Leu Val Leu Thr Arg Lys Asp Leu Leu Phe Gly Ser Ile
            1055                1060                1065

Val Ala Val Asp Glu Pro Thr Arg Pro Ile Tyr Arg Phe Thr Gln
            1070                1075                1080

Glu Asp Leu Arg Lys Arg Arg Val Leu Phe Val His Ser Gly Ala
            1085                1090                1095

Asp Arg Gly Trp Ile Gln Leu Gln Val Ser Asp Gly Gln His Gln
            1100                1105                1110

Ala Thr Ala Leu Leu Glu Val Gln Ala Ser Glu Pro Tyr Leu Arg
            1115                1120                1125
```

```
Val Ala Asn Gly Ser Ser Leu Val Val Pro Gln Gly Gly Gln Gly
1130                1135                1140

Thr Ile Asp Thr Ala Val Leu His Leu Asp Thr Asn Leu Asp Ile
1145                1150                1155

Arg Ser Gly Asp Glu Val His Tyr His Val Thr Ala Gly Pro Arg
1160                1165                1170

Trp Gly Gln Leu Val Arg Ala Gly Gln Pro Ala Thr Ala Phe Ser
1175                1180                1185

Gln Gln Asp Leu Leu Asp Gly Ala Val Leu Tyr Ser His Asn Gly
1190                1195                1200

Ser Leu Ser Pro Arg Asp Thr Met Ala Phe Ser Val Glu Ala Gly
1205                1210                1215

Pro Val His Thr Asp Ala Thr Leu Gln Val Thr Ile Ala Leu Glu
1220                1225                1230

Gly Pro Leu Ala Pro Leu Lys Leu Val Arg His Lys Lys Ile Tyr
1235                1240                1245

Val Phe Gln Gly Glu Ala Ala Glu Ile Arg Arg Asp Gln Leu Glu
1250                1255                1260

Ala Ala Gln Glu Ala Val Pro Pro Ala Asp Ile Val Phe Ser Val
1265                1270                1275

Lys Ser Pro Pro Ser Ala Gly Tyr Leu Val Met Val Ser Arg Gly
1280                1285                1290

Ala Leu Ala Asp Glu Pro Pro Ser Leu Asp Pro Val Gln Ser Phe
1295                1300                1305

Ser Gln Glu Ala Val Asp Thr Gly Arg Val Leu Tyr Leu His Ser
1310                1315                1320

Arg Pro Glu Ala Trp Ser Asp Ala Phe Ser Leu Asp Val Ala Ser
1325                1330                1335

Gly Leu Gly Ala Pro Leu Glu Gly Val Leu Val Glu Leu Glu Val
1340                1345                1350

Leu Pro Ala Ala Ile Pro Leu Glu Ala Gln Asn Phe Ser Val Pro
1355                1360                1365

Glu Gly Gly Ser Leu Thr Leu Ala Pro Pro Leu Leu Arg Val Ser
1370                1375                1380

Gly Pro Tyr Phe Pro Thr Leu Leu Gly Leu Ser Leu Gln Val Leu
1385                1390                1395

Glu Pro Pro Gln His Gly Ala Leu Gln Lys Glu Asp Gly Pro Gln
1400                1405                1410

Ala Arg Thr Leu Ser Ala Phe Ser Trp Arg Met Val Glu Glu Gln
1415                1420                1425

Leu Ile Arg Tyr Val His Asp Gly Ser Glu Thr Leu Thr Asp Ser
1430                1435                1440

Phe Val Leu Met Ala Asn Ala Ser Glu Met Asp Arg Gln Ser His
1445                1450                1455

Pro Val Ala Phe Thr Val Thr Val Leu Pro Val Asn Asp Gln Pro
1460                1465                1470

Pro Ile Leu Thr Thr Asn Thr Gly Leu Gln Met Trp Glu Gly Ala
1475                1480                1485

Thr Ala Pro Ile Pro Ala Glu Ala Leu Arg Ser Thr Asp Gly Asp
1490                1495                1500

Ser Gly Ser Glu Asp Leu Val Tyr Thr Ile Glu Gln Pro Ser Asn
1505                1510                1515

Gly Arg Val Val Leu Arg Gly Ala Pro Gly Thr Glu Val Arg Ser
```

-continued

```
              1520                1525                1530

Phe  Thr  Gln  Ala  Gln  Leu  Asp  Gly  Gly  Leu  Val  Leu  Phe  Ser  His
              1535                1540                1545

Arg  Gly  Thr  Leu  Asp  Gly  Gly  Phe  Arg  Phe  Arg  Leu  Ser  Asp  Gly
              1550                1555                1560

Glu  His  Thr  Ser  Pro  Gly  His  Phe  Phe  Arg  Val  Thr  Ala  Gln  Lys
              1565                1570                1575

Gln  Val  Leu  Leu  Ser  Leu  Lys  Gly  Ser  Gln  Thr  Leu  Thr  Val  Cys
              1580                1585                1590

Pro  Gly  Ser  Val  Gln  Pro  Leu  Ser  Ser  Gln  Thr  Leu  Arg  Ala  Ser
              1595                1600                1605

Ser  Ser  Ala  Gly  Thr  Asp  Pro  Gln  Leu  Leu  Leu  Tyr  Arg  Val  Val
              1610                1615                1620

Arg  Gly  Pro  Gln  Leu  Gly  Arg  Leu  Phe  His  Ala  Gln  Gln  Asp  Ser
              1625                1630                1635

Thr  Gly  Glu  Ala  Leu  Val  Asn  Phe  Thr  Gln  Ala  Glu  Val  Tyr  Ala
              1640                1645                1650

Gly  Asn  Ile  Leu  Tyr  Glu  His  Glu  Met  Pro  Pro  Glu  Pro  Phe  Trp
              1655                1660                1665

Glu  Ala  His  Asp  Thr  Leu  Glu  Leu  Gln  Leu  Ser  Ser  Pro  Pro  Ala
              1670                1675                1680

Arg  Asp  Val  Ala  Ala  Thr  Leu  Ala  Val  Ala  Val  Ser  Phe  Glu  Ala
              1685                1690                1695

Ala  Cys  Pro  Gln  Arg  Pro  Ser  His  Leu  Trp  Lys  Asn  Lys  Gly  Leu
              1700                1705                1710

Trp  Val  Pro  Glu  Gly  Gln  Arg  Ala  Arg  Ile  Thr  Val  Ala  Ala  Leu
              1715                1720                1725

Asp  Ala  Ser  Asn  Leu  Leu  Ala  Ser  Val  Pro  Ser  Pro  Gln  Arg  Ser
              1730                1735                1740

Glu  His  Asp  Val  Leu  Phe  Gln  Val  Thr  Gln  Phe  Pro  Ser  Arg  Gly
              1745                1750                1755

Gln  Leu  Leu  Val  Ser  Glu  Glu  Pro  Leu  His  Ala  Gly  Gln  Pro  His
              1760                1765                1770

Phe  Leu  Gln  Ser  Gln  Leu  Ala  Ala  Gly  Gln  Leu  Val  Tyr  Ala  His
              1775                1780                1785

Gly  Gly  Gly  Gly  Thr  Gln  Gln  Asp  Gly  Phe  His  Phe  Arg  Ala  His
              1790                1795                1800

Leu  Gln  Gly  Pro  Ala  Gly  Ala  Ser  Val  Ala  Gly  Pro  Gln  Thr  Ser
              1805                1810                1815

Glu  Ala  Phe  Ala  Ile  Thr  Val  Arg  Asp  Val  Asn  Glu  Arg  Pro  Pro
              1820                1825                1830

Gln  Pro  Gln  Ala  Ser  Val  Pro  Leu  Arg  Leu  Thr  Arg  Gly  Ser  Arg
              1835                1840                1845

Ala  Pro  Ile  Ser  Arg  Ala  Gln  Leu  Ser  Val  Val  Asp  Pro  Asp  Ser
              1850                1855                1860

Ala  Pro  Gly  Glu  Ile  Glu  Tyr  Glu  Val  Gln  Arg  Ala  Pro  His  Asn
              1865                1870                1875

Gly  Phe  Leu  Ser  Leu  Val  Gly  Gly  Gly  Leu  Gly  Pro  Val  Thr  Arg
              1880                1885                1890

Phe  Thr  Gln  Ala  Asp  Val  Asp  Ser  Gly  Arg  Leu  Ala  Phe  Val  Ala
              1895                1900                1905

Asn  Gly  Ser  Ser  Val  Ala  Gly  Ile  Phe  Gln  Leu  Ser  Met  Ser  Asp
              1910                1915                1920
```

-continued

Gly Ala Ser Pro Pro Leu Pro Met Ser Leu Ala Val Asp Ile Leu
1925                1930                1935

Pro Ser Ala Ile Glu Val Gln Leu Arg Ala Pro Leu Glu Val Pro
1940                1945                1950

Gln Ala Leu Gly Arg Ser Ser Leu Ser Gln Gln Gln Leu Arg Val
1955                1960                1965

Val Ser Asp Arg Glu Glu Pro Glu Ala Ala Tyr Arg Leu Ile Gln
1970                1975                1980

Gly Pro Gln Tyr Gly His Leu Leu Val Gly Gly Arg Pro Thr Ser
1985                1990                1995

Ala Phe Ser Gln Phe Gln Ile Asp Gln Gly Glu Val Val Phe Ala
2000                2005                2010

Phe Thr Asn Phe Ser Ser Ser His Asp His Phe Arg Val Leu Ala
2015                2020                2025

Leu Ala Arg Gly Val Asn Ala Ser Ala Val Val Asn Val Thr Val
2030                2035                2040

Arg Ala Leu Leu His Val Trp Ala Gly Gly Pro Trp Pro Gln Gly
2045                2050                2055

Ala Thr Leu Arg Leu Asp Pro Thr Val Leu Asp Ala Gly Glu Leu
2060                2065                2070

Ala Asn Arg Thr Gly Ser Val Pro Arg Phe Arg Leu Leu Glu Gly
2075                2080                2085

Pro Arg His Gly Arg Val Val Arg Val Pro Arg Ala Arg Thr Glu
2090                2095                2100

Pro Gly Gly Ser Gln Leu Val Glu Gln Phe Thr Gln Gln Asp Leu
2105                2110                2115

Glu Asp Gly Arg Leu Gly Leu Glu Val Gly Arg Pro Glu Gly Arg
2120                2125                2130

Ala Pro Gly Pro Ala Gly Asp Ser Leu Thr Leu Glu Leu Trp Ala
2135                2140                2145

Gln Gly Val Pro Pro Ala Val Ala Ser Leu Asp Phe Ala Thr Glu
2150                2155                2160

Pro Tyr Asn Ala Ala Arg Pro Tyr Ser Val Ala Leu Leu Ser Val
2165                2170                2175

Pro Glu Ala Ala Arg Thr Glu Ala Gly Lys Pro Glu Ser Ser Thr
2180                2185                2190

Pro Thr Gly Glu Pro Gly Pro Met Ala Ser Ser Pro Glu Pro Ala
2195                2200                2205

Val Ala Lys Gly Gly Phe Leu Ser Phe Leu Glu Ala Asn Met Phe
2210                2215                2220

Ser Val Ile Ile Pro Met Cys Leu Val Leu Leu Leu Ala Leu
2225                2230                2235

Ile Leu Pro Leu Leu Phe Tyr Leu Arg Lys Arg Asn Lys Thr Gly
2240                2245                2250

Lys His Asp Val Gln Val Leu Thr Ala Lys Pro Arg Asn Gly Leu
2255                2260                2265

Ala Gly Asp Thr Glu Thr Phe Arg Lys Val Glu Pro Gly Gln Ala
2270                2275                2280

Ile Pro Leu Thr Ala Val Pro Gly Gln Gly Pro Pro Pro Gly Gly
2285                2290                2295

Gln Pro Asp Pro Glu Leu Leu Gln Phe Cys Arg Thr Pro Asn Pro
2300                2305                2310

```
Ala Leu Lys Asn Gly Gln Tyr Trp Val
    2315                2320
```

<210> SEQ ID NO 2
<211> LENGTH: 2327
<212> TYPE: PRT
<213> ORGANISM: Mus musculus

<400> SEQUENCE: 2

```
Met Leu Leu Gly Pro Gly His Pro Leu Ser Ala Pro Ala Leu Ala Leu
1               5                   10                  15

Ala Leu Thr Leu Ala Leu Leu Val Arg Ser Thr Ala Pro Ala Ser Phe
            20                  25                  30

Phe Gly Glu Asn His Leu Glu Val Pro Val Pro Ser Ala Leu Thr Arg
        35                  40                  45

Val Asp Leu Leu Leu Gln Phe Ser Thr Ser Gln Pro Glu Ala Leu Leu
    50                  55                  60

Leu Leu Ala Ala Gly Gln Asp Asp His Leu Leu Gln Leu His Ser
65                  70                  75                  80

Gly Cys Leu Gln Val Arg Leu Ala Leu Gly Gln Lys Glu Leu Lys Leu
                85                  90                  95

Gln Thr Pro Ala Asp Thr Val Leu Ser Asp Ser Ala Pro His Thr Val
            100                 105                 110

Val Leu Thr Val Ser Asp Ser Trp Ala Val Leu Ser Val Asp Gly Val
        115                 120                 125

Leu Asn Thr Ser Ala Pro Ile Pro Arg Ala Ser His Leu Lys Ala Thr
    130                 135                 140

Tyr Gly Leu Phe Val Gly Ser Ser Gly Ser Leu Asp Leu Pro Tyr Leu
145                 150                 155                 160

Lys Gly Ile Ser Arg Pro Leu Arg Gly Cys Leu His Ser Ala Ile Leu
                165                 170                 175

Asn Gly Arg Asn Leu Leu Arg Pro Leu Thr Ser Asp Val His Glu Gly
            180                 185                 190

Cys Ala Glu Glu Phe Ser Ala Gly Asp Glu Val Gly Leu Gly Phe Ser
        195                 200                 205

Gly Pro His Ser Leu Ala Ala Phe Pro Ala Trp Ser Thr Arg Glu Glu
    210                 215                 220

Gly Thr Leu Glu Phe Thr Leu Thr Thr Arg Ser Gln Gln Ala Pro Leu
225                 230                 235                 240

Ala Phe Gln Ala Gly Asp Lys Arg Gly Asn Phe Ile Tyr Val Asp Ile
                245                 250                 255

Phe Glu Gly His Leu Arg Ala Val Val Glu Lys Gly Gln Gly Thr Met
            260                 265                 270

Leu Leu Arg Asn Ser Val Pro Val Ala Asp Gly Gln Pro His Glu Val
        275                 280                 285

Ser Val His Ile Asp Val His Arg Leu Glu Ile Ser Val Asp Gln Tyr
    290                 295                 300

Pro Thr Arg Thr Phe Asn Arg Gly Val Leu Ser Tyr Leu Glu Pro Arg
305                 310                 315                 320

Gly Ser Leu Leu Leu Gly Gly Leu Asp Thr Glu Ala Ser Arg His Leu
                325                 330                 335

Gln Glu His Arg Leu Gly Leu Ala Pro Gly Ala Ala Asn Ile Ser Leu
            340                 345                 350

Val Gly Cys Ile Glu Asp Phe Ser Val Asn Gly Arg Arg Gln Gly Leu
        355                 360                 365
```

-continued

Arg Asp Ala Trp Leu Thr Arg Asp Met Ser Ala Gly Cys Arg Pro Glu
370                 375                 380

Glu Asp Glu Tyr Glu Glu Val Tyr Gly Pro Tyr Glu Thr Phe Ser
385                 390                 395                 400

Thr Leu Ala Pro Glu Ala Trp Pro Ala Met Glu Leu Pro Glu Pro Cys
                405                 410                 415

Ile Pro Glu Pro Gly Leu Pro Ala Val Phe Ala Asn Phe Thr Gln Leu
            420                 425                 430

Leu Thr Ile Ser Pro Leu Val Ala Glu Gly Gly Thr Ala Trp Leu
            435                 440                 445

Glu Trp Arg His Val Gln Pro Thr Leu Asp Leu Thr Glu Ala Glu Leu
450                 455                 460

Arg Lys Ser Gln Val Leu Phe Ser Val Ser Gln Ser Ala Arg His Gly
465                 470                 475                 480

Asp Leu Glu Leu Asp Ile Leu Gly Ala Gln Thr Arg Lys Met Phe Thr
            485                 490                 495

Leu Leu Asp Val Val Asn Arg Lys Ala Arg Phe Val His Asp Gly Ser
            500                 505                 510

Glu Asp Thr Ser Asp Gln Leu Met Leu Glu Val Ser Val Thr Ala Arg
            515                 520                 525

Ala Pro Val Pro Ser Cys Leu Arg Arg Gly Gln Ile Tyr Ile Leu Pro
530                 535                 540

Ile Gln Val Asn Pro Val Asn Asp Pro Pro Arg Ile Ile Phe Pro His
545                 550                 555                 560

Gly Ser Leu Met Val Ile Leu Glu His Thr Gln Lys Pro Leu Gly Pro
            565                 570                 575

Glu Ile Phe Gln Ala Tyr Asp Pro Asp Ser Ala Cys Glu Gly Leu Thr
            580                 585                 590

Phe Gln Leu Leu Gly Val Ser Ser Gly Val Pro Val Glu His Arg Asp
            595                 600                 605

Gln Pro Gly Glu Pro Ala Thr Glu Phe Ser Cys Arg Glu Leu Glu Val
610                 615                 620

Gly Asp Ile Val Tyr Val His Arg Gly Gly Pro Ala Gln Asp Leu Thr
625                 630                 635                 640

Phe Arg Val Ser Asp Gly Met Gln Ala Ser Ala Pro Ala Thr Leu Lys
            645                 650                 655

Val Val Ala Val Arg Pro Ala Ile Gln Ile Leu His Asn Thr Gly Leu
            660                 665                 670

His Leu Ala Gln Gly Ser Ala Ala Ile Leu Pro Ala Asn Leu Ser
            675                 680                 685

Val Glu Thr Asn Ala Val Gly Gln Asp Val Ser Val Leu Phe Arg Val
690                 695                 700

Thr Gly Thr Leu Gln Phe Gly Glu Leu Gln Lys Gln Gly Ala Gly Gly
705                 710                 715                 720

Val Glu Gly Thr Glu Trp Trp Asp Thr Leu Ala Phe His Gln Arg Asp
            725                 730                 735

Val Glu Gln Gly Arg Val Arg Tyr Leu Ser Thr Asp Pro Gln His His
            740                 745                 750

Thr Gln Asp Thr Val Glu Asp Leu Ile Leu Glu Val Gln Val Gly Gln
            755                 760                 765

Glu Thr Leu Ser Asn Leu Ser Phe Pro Val Thr Ile Gln Arg Ala Thr
770                 775                 780

```
Val Trp Met Leu Arg Leu Glu Pro Leu His Thr Gln Asn Pro His Gln
785                 790                 795                 800

Glu Thr Leu Thr Pro Ala His Leu Glu Ala Ser Leu Glu Glu Glu
            805                 810                 815

Glu Glu Gly Ser Pro Gln Pro His Thr Phe His Tyr Glu Leu Val Gln
                820                 825                 830

Ala Pro Arg Arg Gly Asn Leu Leu Gln Gly Thr Arg Leu Ser Asp
            835                 840                 845

Gly Glu Ser Phe Ser Gln Ser Asp Leu Gln Ala Gly Arg Val Thr Tyr
        850                 855                 860

Arg Ala Thr Met Arg Thr Ser Glu Ala Ala Asp Asp Ser Phe Arg Phe
865                 870                 875                 880

Arg Val Thr Ser Pro Pro His Phe Ser Pro Leu Tyr Thr Phe Pro Ile
                885                 890                 895

His Ile Gly Gly Asp Pro Asn Ala Pro Val Leu Thr Asn Val Leu Leu
            900                 905                 910

Met Val Pro Glu Gly Gly Glu Gly Val Leu Ser Ala Asp His Leu Phe
            915                 920                 925

Val Lys Ser Leu Asn Ser Ala Ser Tyr Leu Tyr Glu Val Met Glu Gln
        930                 935                 940

Pro His His Gly Lys Leu Ala Trp Arg Asp Pro Lys Gly Lys Ser Thr
945                 950                 955                 960

Pro Val Thr Ser Phe Thr Asn Glu Asp Leu Leu His Gly Arg Leu Val
                965                 970                 975

Tyr Gln His Asp Asp Ser Glu Thr Ile Glu Asp Ile Pro Phe Val
            980                 985                 990

Ala Thr Arg Gln Gly Glu Gly Ser  Gly Asp Met Ala Trp  Glu Glu Val
            995                 1000                 1005

Arg Gly  Val Phe Arg Val Ala  Ile Gln Pro Val Asn  Asp His Ala
    1010                 1015                 1020

Pro Val  Gln Thr Ile Ser Arg  Val Phe His Val Ala  Arg Gly Gly
    1025                 1030                 1035

Gln Arg  Leu Leu Thr Thr Asp  Val Ala Phe Ser  Asp Ala Asp
    1040                 1045                 1050

Ser Gly  Phe Ser Asp Ala Gln  Leu Val Leu Thr Arg  Lys Asp Leu
    1055                 1060                 1065

Leu Phe  Gly Ser Ile Val Ala  Met Glu Glu Pro Thr  Arg Pro Ile
    1070                 1075                 1080

Tyr Arg  Phe Thr Gln Glu Asp  Leu Arg Lys Lys Gln  Val Leu Phe
    1085                 1090                 1095

Val His  Ser Gly Ala Asp His  Gly Trp Leu Gln Leu  Gln Val Ser
    1100                 1105                 1110

Asp Gly  Gln His Gln Ala Thr  Ala Met Leu Glu Val  Gln Ala Ser
    1115                 1120                 1125

Glu Pro  Tyr Leu His Val Ala  Asn Ser Ser Ser Leu  Val Val Pro
    1130                 1135                 1140

Gln Gly  Gly Gln Gly Thr Ile  Asp Thr Ala Val Leu  Gln Leu Asp
    1145                 1150                 1155

Thr Asn  Leu Asp Ile Arg Ser  Gly Asn Glu Val His  Tyr His Val
    1160                 1165                 1170

Thr Ala  Gly Pro Gln Trp Gly  Gln Leu Leu Arg Asp  Gly Gln Ser
    1175                 1180                 1185

Val Thr  Ser Phe Ser Gln Arg  Asp Leu Leu Asp Gly  Ala Ile Leu
```

-continued

|  |  |  | 1190 |  |  |  | 1195 |  |  |  | 1200 |
| Tyr | Ser | His | Asn | Gly | Ser | Leu | Ser | Pro | Gln | Asp | Thr | Leu | Ala | Phe |
|  |  |  | 1205 |  |  |  | 1210 |  |  |  | 1215 |
| Ser | Val | Ala | Ala | Gly | Pro | Val | His | Thr | Asn | Thr | Phe | Leu | Gln | Val |
|  |  |  | 1220 |  |  |  | 1225 |  |  |  | 1230 |
| Thr | Ile | Ala | Leu | Glu | Gly | Pro | Leu | Ala | Pro | Leu | Gln | Leu | Val | Gln |
|  |  |  | 1235 |  |  |  | 1240 |  |  |  | 1245 |
| His | Lys | Lys | Ile | Tyr | Val | Phe | Gln | Gly | Glu | Ala | Ala | Glu | Ile | Arg |
|  |  |  | 1250 |  |  |  | 1255 |  |  |  | 1260 |
| Arg | Asp | Gln | Leu | Glu | Val | Val | Gln | Glu | Ala | Val | Leu | Pro | Ala | Asp |
|  |  |  | 1265 |  |  |  | 1270 |  |  |  | 1275 |
| Ile | Met | Phe | Ser | Leu | Arg | Ser | Pro | Pro | Asn | Ala | Gly | Tyr | Leu | Val |
|  |  |  | 1280 |  |  |  | 1285 |  |  |  | 1290 |
| Met | Val | Ser | His | Gly | Ala | Ser | Ala | Glu | Glu | Pro | Pro | Ser | Leu | Asp |
|  |  |  | 1295 |  |  |  | 1300 |  |  |  | 1305 |
| Pro | Val | Gln | Ser | Phe | Ser | Gln | Glu | Ala | Val | Asn | Ser | Gly | Arg | Val |
|  |  |  | 1310 |  |  |  | 1315 |  |  |  | 1320 |
| Leu | Tyr | Leu | His | Ser | Arg | Pro | Gly | Ala | Trp | Ser | Asp | Ser | Phe | Ser |
|  |  |  | 1325 |  |  |  | 1330 |  |  |  | 1335 |
| Leu | Asp | Val | Ala | Ser | Gly | Leu | Gly | Asp | Pro | Leu | Glu | Gly | Ile | Ser |
|  |  |  | 1340 |  |  |  | 1345 |  |  |  | 1350 |
| Val | Glu | Leu | Glu | Val | Leu | Pro | Thr | Val | Ile | Pro | Leu | Asp | Val | Gln |
|  |  |  | 1355 |  |  |  | 1360 |  |  |  | 1365 |
| Asn | Phe | Ser | Val | Pro | Glu | Gly | Gly | Thr | Arg | Thr | Leu | Ala | Pro | Pro |
|  |  |  | 1370 |  |  |  | 1375 |  |  |  | 1380 |
| Leu | Val | Gln | Ile | Thr | Gly | Pro | Tyr | Phe | Pro | Thr | Leu | Pro | Gly | Leu |
|  |  |  | 1385 |  |  |  | 1390 |  |  |  | 1395 |
| Val | Leu | Gln | Val | Leu | Glu | Pro | Pro | Gln | His | Gly | Ala | Leu | Gln | Lys |
|  |  |  | 1400 |  |  |  | 1405 |  |  |  | 1410 |
| Glu | Asp | His | Ser | Gln | Asp | Gly | Ser | Leu | Ser | Thr | Phe | Ser | Trp | Arg |
|  |  |  | 1415 |  |  |  | 1420 |  |  |  | 1425 |
| Glu | Val | Glu | Glu | Gln | Leu | Ile | Arg | Tyr | Val | His | Asp | Gly | Ser | Glu |
|  |  |  | 1430 |  |  |  | 1435 |  |  |  | 1440 |
| Thr | Gln | Thr | Asp | Ala | Phe | Val | Leu | Leu | Ala | Asn | Ala | Ser | Glu | Met |
|  |  |  | 1445 |  |  |  | 1450 |  |  |  | 1455 |
| Asp | Arg | Gln | Ser | Gln | Pro | Val | Ala | Phe | Thr | Ile | Thr | Ile | Leu | Pro |
|  |  |  | 1460 |  |  |  | 1465 |  |  |  | 1470 |
| Val | Asn | Asp | Gln | Pro | Pro | Val | Leu | Thr | Thr | Asn | Thr | Gly | Leu | Gln |
|  |  |  | 1475 |  |  |  | 1480 |  |  |  | 1485 |
| Ile | Trp | Glu | Gly | Ala | Ile | Val | Pro | Ile | Pro | Glu | Ala | Leu | Arg |
|  |  |  | 1490 |  |  |  | 1495 |  |  |  | 1500 |
| Gly | Thr | Asp | Asn | Asp | Ser | Gly | Pro | Glu | Asp | Leu | Val | Tyr | Thr | Ile |
|  |  |  | 1505 |  |  |  | 1510 |  |  |  | 1515 |
| Glu | Gln | Pro | Ser | Asn | Gly | Arg | Ile | Ala | Leu | Arg | Val | Ala | Pro | Asp |
|  |  |  | 1520 |  |  |  | 1525 |  |  |  | 1530 |
| Thr | Glu | Val | His | Arg | Phe | Thr | Gln | Ala | Gln | Leu | Asp | Ser | Gly | Leu |
|  |  |  | 1535 |  |  |  | 1540 |  |  |  | 1545 |
| Val | Leu | Phe | Ser | His | Arg | Gly | Ala | Leu | Glu | Gly | Gly | Phe | His | Phe |
|  |  |  | 1550 |  |  |  | 1555 |  |  |  | 1560 |
| Asp | Leu | Ser | Asp | Gly | Ala | His | Thr | Ser | Pro | Gly | His | Phe | Phe | Arg |
|  |  |  | 1565 |  |  |  | 1570 |  |  |  | 1575 |
| Val | Val | Ala | Gln | Lys | Gln | Ala | Leu | Leu | Ser | Leu | Glu | Gly | Thr | Arg |
|  |  |  | 1580 |  |  |  | 1585 |  |  |  | 1590 |

```
Lys Leu Thr Val Cys Pro Glu Ser Val Gln Pro Leu Ser Ser Gln
    1595                1600                1605

Ser Leu Ser Ala Ser Ser Ser Thr Gly Ala Asp Pro Arg His Leu
    1610                1615                1620

Leu Tyr Arg Val Val Arg Gly Pro Gln Leu Gly Arg Leu Leu His
    1625                1630                1635

Ala Gln Gln Gly Ser Ala Glu Glu Val Leu Val Asn Phe Thr Gln
    1640                1645                1650

Ala Glu Val Asn Ala Gly Asn Ile Leu Tyr Glu His Glu Met Ser
    1655                1660                1665

Ser Glu Pro Phe Trp Glu Ala His Asp Thr Ile Gly Leu Leu Leu
    1670                1675                1680

Ser Ser Pro Pro Ala Arg Asp Leu Ala Ala Thr Leu Ala Val Met
    1685                1690                1695

Val Ser Phe Asp Ala Ala Cys Pro Gln Arg Pro Ser Arg Leu Trp
    1700                1705                1710

Lys Asn Lys Gly Leu Trp Val Pro Glu Gly Gln Arg Ala Lys Ile
    1715                1720                1725

Thr Val Ala Ala Leu Asp Ala Ala Asn Leu Leu Ala Ser Val Pro
    1730                1735                1740

Ala Ser Gln Arg Ser Arg His Asp Val Leu Phe Gln Val Thr Gln
    1745                1750                1755

Phe Pro Thr Arg Gly Gln Leu Leu Val Ser Glu Glu Pro Leu His
    1760                1765                1770

Ala Arg Arg Pro Tyr Phe Leu Gln Ser Glu Leu Ala Ala Gly Gln
    1775                1780                1785

Leu Val Tyr Ala His Gly Gly Gly Gly Thr Gln Gln Asp Gly Phe
    1790                1795                1800

Arg Phe Arg Ala His Leu Gln Gly Pro Thr Gly Thr Ser Val Ala
    1805                1810                1815

Gly Pro Gln Thr Ser Glu Ala Phe Val Ile Thr Val Arg Asp Val
    1820                1825                1830

Asn Glu Arg Pro Pro Gln Pro Gln Ala Ser Ile Pro Leu Arg Val
    1835                1840                1845

Thr Arg Gly Ser Arg Ala Pro Val Ser Arg Ala Gln Leu Ser Val
    1850                1855                1860

Val Asp Pro Asp Ser Ala Pro Gly Glu Ile Glu Tyr Glu Val Gln
    1865                1870                1875

Arg Ala Pro His Asn Gly Phe Leu Ser Leu Ala Gly Asp Asn Thr
    1880                1885                1890

Gly Pro Val Thr His Phe Thr Gln Ala Asp Val Asp Ala Gly Arg
    1895                1900                1905

Leu Ala Phe Val Ala Asn Gly Ser Ser Val Ala Gly Val Phe Gln
    1910                1915                1920

Leu Ser Met Ser Asp Gly Ala Ser Pro Pro Ile Pro Met Ser Leu
    1925                1930                1935

Ala Val Asp Val Leu Pro Ser Thr Ile Glu Val Gln Leu Arg Ala
    1940                1945                1950

Pro Leu Glu Val Pro Gln Ala Leu Gly Arg Thr Ser Leu Ser Arg
    1955                1960                1965

Gln Gln Leu Gln Val Ile Ser Asp Arg Glu Glu Pro Asp Val Ala
    1970                1975                1980
```

Tyr Arg Leu Thr Gln Gly Pro Leu Tyr Gly Gln Leu Leu Val Gly
1985                1990                1995

Gly Gln Pro Ala Ser Ala Phe Ser Gln Leu Gln Val Asp Gln Gly
2000                2005                2010

Asp Val Val Phe Val Phe Thr Asn Phe Ser Ser Ser Gln Asp His
2015                2020                2025

Phe Lys Val Val Ala Leu Ala Arg Gly Val Asn Ala Ser Ala Thr
2030                2035                2040

Val Asn Val Thr Val Gln Ala Leu Leu His Val Trp Ala Gly Gly
2045                2050                2055

Pro Trp Pro Gln Gly Thr Thr Leu Arg Leu Asp Pro Thr Val Leu
2060                2065                2070

Asp Ala Ser Glu Leu Ala Asn Arg Thr Gly Ser Met Pro His Phe
2075                2080                2085

Arg Leu Leu Ala Gly Pro Arg Tyr Gly Arg Val Arg Val Ser
2090                2095                2100

Gln Gly Arg Thr Glu Ser Arg Ser Asn Gln Leu Val Glu His Phe
2105                2110                2115

Thr Gln Arg Asp Leu Glu Glu Gly Gln Leu Gly Leu Glu Val Gly
2120                2125                2130

Lys Pro Glu Gly Arg Ser Thr Gly Pro Ala Gly Asp Arg Leu Thr
2135                2140                2145

Leu Glu Leu Trp Ala Lys Gly Val Pro Pro Ala Val Ala Leu Leu
2150                2155                2160

Asp Phe Ala Thr Glu Pro Tyr His Ala Ala Lys Ser Tyr Ser Val
2165                2170                2175

Ala Leu Leu Ser Val Pro Glu Ala Val Arg Thr Glu Thr Glu Lys
2180                2185                2190

Pro Gly Arg Ser Val Pro Thr Gly Gln Pro Gly Gln Ala Ala Ser
2195                2200                2205

Ser Pro Val Pro Thr Ala Ala Lys Gly Gly Phe Leu Gly Phe Leu
2210                2215                2220

Glu Ala Asn Met Phe Ser Ile Ile Ile Pro Val Cys Leu Ile Leu
2225                2230                2235

Leu Leu Leu Ala Leu Ile Leu Pro Leu Leu Phe Tyr Leu Arg Lys
2240                2245                2250

Arg Asn Lys Thr Gly Lys His Asp Val Gln Val Leu Thr Ala Lys
2255                2260                2265

Pro Arg Asn Gly Leu Ala Gly Asp Thr Glu Thr Phe Arg Lys Val
2270                2275                2280

Glu Pro Gly Gln Ala Ile Pro Leu Ile Thr Val Pro Gly Gln Gly
2285                2290                2295

Pro Pro Pro Gly Gly Gln Pro Asp Pro Glu Leu Leu Gln Phe Cys
2300                2305                2310

Arg Thr Pro Asn Pro Ala Leu Arg Asn Gly Gln Tyr Trp Val
2315                2320                2325

<210> SEQ ID NO 3
<211> LENGTH: 1329
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
cagatccagt tggtgcagtc tggacctgag ctgaagaagc ctggagagac agtcaagatc    60
tcctgcaagg cttctggtta taccttcaca gactattcaa tgcactgggt gaagaagact   120
ccaggaaagg gtttaaagtg gctgggctgg ataaacactg cgactggtga gccaacatat   180
gcagatgact tcaagggacg gtttgccatc tctttggaaa cctctgccag gactgtctat   240
ttgcagatca ataatctcag aaatgaggac acggctacat atttctgttt tagttactac   300
gactactggg gccaaggcac cactctcaca gtttccgcct ccaccaaggg cccatcggtc   360
ttccccctgg cacccctcc caagagcacc tctgggggca gcggccct gggctgcctg       420 gtcaaggact acttccccga accggtgacg gtgtcgtgga actcaggcgc cctgaccagc   480
ggcgtgcaca ccttcccggc cgtcctacag tcctcaggac tctactccct cagcagcgtg   540
gtgaccgtgc cctccagcag cttgggcacc cagacctaca tctgcaacgt gaatcacaag   600
cccagcaaca ccaaggtgga caagagagtt gagcccaaat cttgtgacaa aactcacaca   660
tgcccaccgt gcccagcacc tgaactcctg gggggaccgt cagtcttcct cttccccca    720 aaacccaagg acaccctcat gatctcccgg acccctgagg tcacatgcgt ggtggtggac   780
gtgagccacg aagaccctga ggtcaagttc aactggtacg tggacggcgt ggaggtgcat   840
aatgccaaga caaagccgcg ggaggagcag tacaacagca cgtaccgtgt ggtcagcgtc   900
ctcaccgtcc tgcaccagga ctggctgaat ggcaaggagt acaagtgcaa ggtctccaac   960
aaagccctcc cagcccccat cgagaaaacc atctccaaag ccaaagggca gccccgagaa  1020
ccacaggtgt acaccctgcc cccatcccgg gatgagctga ccaagaacca ggtcagcctg  1080
acctgcctgg tcaaaggctt ctatcccagc gacatcgccg tggagtggga gagcaatggg  1140
cagccggaga acaactacaa gaccacgcct cccgtgctgg actccgacgg ctccttcttc  1200
ctctacagca agctcaccgt ggacaagagc aggtggcagc aggggaacgt cttctcatgc  1260
tccgtgatgc atgaggctct gcacaaccac tacacgcaga agagcctctc cctgtctccg  1320
ggtaaatga                                                          1329
```

<210> SEQ ID NO 4
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Lys Thr Pro Gly Lys Gly Leu Lys Trp Leu
        35                  40                  45

Gly Trp Ile Asn Thr Ala Thr Gly Glu Pro Thr Tyr Ala Asp Asp Phe
    50                  55                  60

Lys Gly Arg Phe Ala Ile Ser Leu Glu Thr Ser Ala Arg Thr Val Tyr
65                  70                  75                  80

Leu Gln Ile Asn Asn Leu Arg Asn Glu Asp Thr Ala Thr Tyr Phe Cys
                85                  90                  95

Phe Ser Tyr Tyr Asp Tyr Trp Gly Gln Gly Thr Thr Leu Thr Val Ser
            100                 105                 110
```

Ala Ser Thr Lys Gly Pro Ser Val Phe Pro Leu Ala Pro Ser Ser Lys
            115                 120                 125

Ser Thr Ser Gly Gly Thr Ala Ala Leu Gly Cys Leu Val Lys Asp Tyr
130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Leu Gly Thr Gln Thr
                180                 185                 190

Tyr Ile Cys Asn Val Asn His Lys Pro Ser Asn Thr Lys Val Asp Lys
            195                 200                 205

Arg Val Glu Pro Lys Ser Cys Asp Lys Thr His Thr Cys Pro Pro Cys
210                 215                 220

Pro Ala Pro Glu Leu Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser His Glu Asp Pro Glu Val Lys Phe Asn Trp
                260                 265                 270

Tyr Val Asp Gly Val Glu Val His Asn Ala Lys Thr Lys Pro Arg Glu
            275                 280                 285

Glu Gln Tyr Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Ala Leu Pro Ala Pro Ile Glu Lys Thr Ile Ser Lys Ala Lys Gly
                325                 330                 335

Gln Pro Arg Glu Pro Gln Val Tyr Thr Leu Pro Pro Ser Arg Asp Glu
            340                 345                 350

Leu Thr Lys Asn Gln Val Ser Leu Thr Cys Leu Val Lys Gly Phe Tyr
            355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
                405                 410                 415

Val Phe Ser Cys Ser Val Met His Glu Ala Leu His Asn His Tyr Thr
            420                 425                 430

Gln Lys Ser Leu Ser Leu Ser Pro Gly Lys
        435                 440

<210> SEQ ID NO 5
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gacatcaagc tgtcccagtc ccctccatc ctgtccgtga ccccggcga gaccgtgtcc      60 ctgtcctgcc gggcctccca gaccatctac aagaacctgc actggtacca gcagaagtcc     120
caccggtccc ccggctgct gatcaagtac ggctccgact ccatctccgg catcccctcc     180

```
cggttcaccg gctccggctc cggcaccgac tacaccctga acatcaactc cgtgaagccc    240
gaggacgagg gcatctacta ctgcctgcag ggctactcca ccccctggac cttcggcggc    300
ggcaccaagc tggagatcaa gcggaccgtg gccgccccct ccgtgttcat cttccccccc    360
tccgacgagc agctgaagtc cggcaccgcc tccgtggtgt gcctgctgaa caacttctac    420
ccccgggagg ccaaggtgca gtggaaggtg gacaacgccc tgcagtccgg caactcccag    480
gagtccgtga ccgagcagga ctccaaggac tccacctact ccctgtcctc caccctgacc    540
ctgtccaagg ccgactacga gaagcacaag gtgtacgcct gcgaggtgac ccaccagggc    600
ctgtcctccc ccgtgaccaa gtccttcaac cggggcgagt gctag                    645
```

<210> SEQ ID NO 6
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

```
Asp Ile Lys Leu Ser Gln Ser Pro Ser Ile Leu Ser Val Thr Pro Gly
1               5                  10                  15

Glu Thr Val Ser Leu Ser Cys Arg Ala Ser Gln Thr Ile Tyr Lys Asn
            20                  25                  30

Leu His Trp Tyr Gln Gln Lys Ser His Arg Ser Pro Arg Leu Leu Ile
        35                  40                  45

Lys Tyr Gly Ser Asp Ser Ile Ser Gly Ile Pro Ser Arg Phe Thr Gly
    50                  55                  60

Ser Gly Ser Gly Thr Asp Tyr Thr Leu Asn Ile Asn Ser Val Lys Pro
65                  70                  75                  80

Glu Asp Glu Gly Ile Tyr Tyr Cys Leu Gln Gly Tyr Ser Thr Pro Trp
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 7
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
cagatccagc tggtgcagtc cggccccgag gtgaagaagc ccggcgcctc cgtgaagatc    60
tcctgcaagg cctccggcta caccttcacc gactactcca tgcactgggt gaagaaggcc   120
cccggccagg gcctggagtg gctgggctgg atcaacaccg ccaccggcga gcccacctac   180
gccgacgact tcaagggccg gttcaccatc accctggaca cctccgcccg gaccgtgtac   240
ctgcagatca acaacctgcg gtccgaggac accgccacct acttctgctt ctcctactac   300
gactactggg gccagggcac cctgctgacc gtgtcctccg cctccaccaa gggcccatcg   360
gtcttccccc tggcaccctc ctccaagagc acctctgggg cacagcggcc ctgggctgc    420
ctggtcaagg actacttccc cgaaccggtg acggtgtcgt ggaactcagg cgccctgacc   480
agcggcgtgc acaccttccc ggccgtccta cagtcctcag gactctactc cctcagcagc   540
gtggtgaccg tgcctccag cagcttgggc acccagacct acatctgcaa cgtgaatcac    600
aagcccagca acaccaaggt ggacaagaga gttgagccca aatcttgtga caaaactcac   660
acatgcccac cgtgcccagc acctgaactc ctggggggac cgtcagtctt cctcttcccc   720
ccaaaaccca aggacaccct catgatctcc cggacccctg aggtcacatg cgtggtggtg   780
gacgtgagcc acgaagaccc tgaggtcaag ttcaactggt acgtggacgg cgtggaggtg   840
cataatgcca agacaaagcc gcgggaggag cagtacaaca gcacgtaccg tgtggtcagc   900
gtcctcaccg tcctgcacca ggactggctg aatggcaagg agtacaagtg caaggtctcc   960
aacaaagccc tcccagcccc catcgagaaa accatctcca agccaaaagg cagccccga   1020
gaaccacagg tgtacaccct gcccccatcc cgggatgagc tgaccaagaa ccaggtcagc  1080
ctgacctgcc tggtcaaagg cttctatccc agcgacatcg ccgtggagtg ggagagcaat  1140
gggcagccgg agaacaacta caagaccacg cctcccgtgc tggactccga cggctccttc  1200
ttcctctaca gcaagctcac cgtggacaag agcaggtggc agcaggggaa cgtcttctca  1260
tgctccgtga tgcatgaggc tctgcacaac cactacacgc agaagagcct ctccctgtct  1320
ccgggtaaat ga                                                      1332
```

<210> SEQ ID NO 8
<211> LENGTH: 443
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 8

```
Gln Ile Gln Leu Val Gln Ser Gly Pro Glu Val Lys Pro Gly Ala
1               5                   10                  15

Ser Val Lys Ile Ser Cys Lys Ala Ser Gly Tyr Thr Phe Thr Asp Tyr
                20                  25                  30

Ser Met His Trp Val Lys Lys Ala Pro Gly Gln Gly Leu Glu Trp Leu
            35                  40                  45

Gly Trp Ile Asn Thr Ala Thr Gly Glu Pro Thr Tyr Ala Asp Asp Phe
        50                  55                  60

Lys Gly Arg Phe Thr Ile Thr Leu Asp Thr Ser Ala Arg Thr Val Tyr
65                  70                  75                  80

Leu Gln Ile Asn Asn Leu Arg Ser Glu Asp Thr Ala Thr Tyr Phe Cys
                85                  90                  95

Phe Ser Tyr Tyr Asp Tyr Trp Gly Gln Gly Thr Leu Leu Thr Val Ser
                100                 105                 110
```

Ser Ala Ser Thr Lys Gly Pro Ser Val Phe Pro Leu Ala Pro Ser Ser
            115                 120                 125

Lys Ser Thr Ser Gly Gly Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Gln
            180                 185                 190

Thr Tyr Ile Cys Asn Val Asn His Lys Pro Ser Asn Thr Lys Val Asp
        195                 200                 205

Lys Arg Val Glu Pro Lys Ser Cys Asp Lys Thr His Thr Cys Pro Pro
    210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Lys Phe Asn
            260                 265                 270

Trp Tyr Val Asp Gly Val Glu Val His Asn Ala Lys Thr Lys Pro Arg
        275                 280                 285

Glu Glu Gln Tyr Asn Ser Thr Tyr Arg Val Val Ser Val Leu Thr Val
    290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
                325                 330                 335

Gly Gln Pro Arg Glu Pro Gln Val Tyr Thr Leu Pro Pro Ser Arg Asp
            340                 345                 350

Glu Leu Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 9
<211> LENGTH: 1332
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
caggtgcagc tggtgcagtc cggccccgag gtgaagaagc ccggcgcctc cgtgaagatc     60
tcctgcaagg cctccggcta caccttcacc gactactcca tgcactgggt gaagaaggcc    120

-continued

```
cccggccagg gcctgaagtg gctgggctgg atcaacaccg ccaccggcga gcccacctac      180
gccgacgact tcaagggccg gttcaccatc accctggaca cctccgcccg gaccgtgtac      240
ctggagatct cctccctgcg gtccgaggac accgccacct acttctgctt ctcctactac      300
gactactggg gccagggcac cctgctgacc gtgtcctccg cctccaccaa gggcccatcg      360
gtcttccccc tggcaccctc ctccaagagc acctctgggg cacagcggc cctgggctgc       420
ctggtcaagg actacttccc cgaaccggtg acggtgtcgt ggaactcagg cgccctgacc      480
agcggcgtgc acaccttccc ggccgtccta cagtcctcag gactctactc cctcagcagc      540
gtggtgaccg tgccctccag cagcttgggc acccagacct acatctgcaa cgtgaatcac      600
aagcccagca caccaaggt ggacaagaga gttgagccca atcttgtga caaaactcac        660
acatgcccac cgtgcccagc acctgaactc ctggggggac cgtcagtctt cctcttcccc      720
ccaaaaccca aggacaccct catgatctcc cggacccctg aggtcacatg cgtggtggtg      780
gacgtgagcc acgaagaccc tgaggtcaag ttcaactggt acgtggacgg cgtggaggtg      840
cataatgcca agacaaagcc gcgggaggag cagtacaaca gcacgtaccg tgtggtcagc      900
gtcctcaccg tcctgcacca ggactggctg aatggcaagg agtacaagtg caaggtctcc      960
aacaaagccc tcccagcccc catcgagaaa accatctcca aagccaaagg gcagccccga      1020
gaaccacagg tgtacaccct gcccccatcc cgggatgagc tgaccaagaa ccaggtcagc      1080
ctgacctgcc tggtcaaagg cttctatccc agcgacatcg ccgtggagtg ggagagcaat      1140
gggcagccgg agaacaacta caagaccacg cctcccgtgc tggactccga cggctccttc      1200
ttcctctaca gcaagctcac cgtggacaag agcaggtggc agcaggggaa cgtcttctca      1260
tgctccgtga tgcatgaggc tctgcacaac cactacacgc agaagagcct ctccctgtct      1320
ccgggtaaat ga                                                          1332
```

<210> SEQ ID NO 10
<211> LENGTH: 443
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 10

```
Gln Val Gln Leu Val Gln Ser Gly Pro Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Ser Met His Trp Val Lys Ala Pro Gly Gln Gly Leu Lys Trp Leu
        35                  40                  45

Gly Trp Ile Asn Thr Ala Thr Gly Glu Pro Thr Tyr Ala Asp Asp Phe
    50                  55                  60

Lys Gly Arg Phe Thr Ile Thr Leu Asp Thr Ser Ala Arg Thr Val Tyr
65                  70                  75                  80

Leu Glu Ile Ser Ser Leu Arg Ser Glu Asp Thr Ala Thr Tyr Phe Cys
                85                  90                  95

Phe Ser Tyr Tyr Asp Tyr Trp Gly Gln Gly Thr Leu Thr Val Ser
            100                 105                 110

Ser Ala Ser Thr Lys Gly Pro Ser Val Phe Pro Leu Ala Pro Ser Ser
        115                 120                 125

Lys Ser Thr Ser Gly Gly Thr Ala Ala Leu Gly Cys Leu Val Lys Asp
    130                 135                 140
```

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
            165                 170                 175

Ser Leu Ser Ser Val Val Thr Val Pro Ser Ser Ser Leu Gly Thr Gln
        180                 185                 190

Thr Tyr Ile Cys Asn Val Asn His Lys Pro Ser Asn Thr Lys Val Asp
    195                 200                 205

Lys Lys Val Glu Pro Lys Ser Cys Asp Lys Thr His Thr Cys Pro Pro
210                 215                 220

Cys Pro Ala Pro Glu Leu Leu Gly Gly Pro Ser Val Phe Leu Phe Pro
225                 230                 235                 240

Pro Lys Pro Lys Asp Thr Leu Met Ile Ser Arg Thr Pro Glu Val Thr
            245                 250                 255

Cys Val Val Val Asp Val Ser His Glu Asp Pro Glu Val Lys Phe Asn
        260                 265                 270

Trp Tyr Val Asp Gly Val Glu Val His Asn Ala Lys Thr Lys Pro Arg
    275                 280                 285

Glu Glu Gln Tyr Asn Ser Thr Tyr Arg Val Val Ser Val Leu Thr Val
290                 295                 300

Leu His Gln Asp Trp Leu Asn Gly Lys Glu Tyr Lys Cys Lys Val Ser
305                 310                 315                 320

Asn Lys Ala Leu Pro Ala Pro Ile Glu Lys Thr Ile Ser Lys Ala Lys
            325                 330                 335

Gly Gln Pro Arg Glu Pro Gln Val Tyr Thr Leu Pro Pro Ser Arg Glu
        340                 345                 350

Glu Met Thr Lys Asn Gln Val Ser Leu Thr Cys Leu Val Lys Gly Phe
    355                 360                 365

Tyr Pro Ser Asp Ile Ala Val Glu Trp Glu Ser Asn Gly Gln Pro Glu
370                 375                 380

Asn Asn Tyr Lys Thr Thr Pro Pro Val Leu Asp Ser Asp Gly Ser Phe
385                 390                 395                 400

Phe Leu Tyr Ser Lys Leu Thr Val Asp Lys Ser Arg Trp Gln Gln Gly
            405                 410                 415

Asn Val Phe Ser Cys Ser Val Met His Glu Ala Leu His Asn His Tyr
        420                 425                 430

Thr Gln Lys Ser Leu Ser Leu Ser Pro Gly Lys
    435                 440

<210> SEQ ID NO 11
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11
gagatcaagc tgacccagtc ccccctccatc ctgtccgtgt cccccggcga gaccgtgacc      60
ctgtcctgcc gggcctccca gaccatctac aagaacctgc actggtacca gcagaagtcc     120
caccggtccc cccggctgct gatcaagtac ggctccgact ccatctccgg catccccgcc     180
cggttctccg gctccggctc cggcaccgac tacaccctga ccatcaactc cgtgaagccc     240
gaggacgagg gcatctacta ctgcctgcag ggctactcca cccccctgga cttcggccag     300

```
ggcaccaagc tgagatcaa gcggaccgtg gccgccccct ccgtgttcat cttcccccc     360 tccgacgagc agctgaagtc cggcaccgcc tccgtggtgt gcctgctgaa caacttctac    420
ccccgggagg ccaaggtgca gtggaaggtg gacaacgccc tgcagtccgg caactcccag    480
gagtccgtga ccgagcagga ctccaaggac tccacctact ccctgtcctc caccctgacc    540
ctgtccaagg ccgactacga gaagcacaag gtgtacgcct gcgaggtgac ccaccagggc    600
ctgtcctccc ccgtgaccaa gtccttcaac cggggcgagt gctag                   645
```

```
<210> SEQ ID NO 12
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12
```

| | | | | | | | | | | | | | | | |
|---|---|---|---|---|---|---|---|---|---|---|---|---|---|---|---|
| Glu | Ile | Lys | Leu | Thr | Gln | Ser | Pro | Ser | Ile | Leu | Ser | Val | Ser | Pro | Gly |
| 1 | | | | 5 | | | | | 10 | | | | | 15 | |
| Glu | Thr | Val | Thr | Leu | Ser | Cys | Arg | Ala | Ser | Gln | Thr | Ile | Tyr | Lys | Asn |
| | | | 20 | | | | | 25 | | | | | 30 | | |
| Leu | His | Trp | Tyr | Gln | Gln | Lys | Ser | His | Arg | Ser | Pro | Arg | Leu | Leu | Ile |
| | | | 35 | | | | | 40 | | | | | 45 | | |
| Lys | Tyr | Gly | Ser | Asp | Ser | Ile | Ser | Gly | Ile | Pro | Ala | Arg | Phe | Ser | Gly |
| | 50 | | | | | 55 | | | | | 60 | | | | |
| Ser | Gly | Ser | Gly | Thr | Asp | Tyr | Thr | Leu | Thr | Ile | Asn | Ser | Val | Lys | Pro |
| 65 | | | | | 70 | | | | | 75 | | | | | 80 |
| Glu | Asp | Glu | Gly | Ile | Tyr | Tyr | Cys | Leu | Gln | Gly | Tyr | Ser | Thr | Pro | Trp |
| | | | | 85 | | | | | 90 | | | | | 95 | |
| Thr | Phe | Gly | Gln | Gly | Thr | Lys | Leu | Glu | Ile | Lys | Arg | Thr | Val | Ala | Ala |
| | | | | 100 | | | | | 105 | | | | | 110 | |
| Pro | Ser | Val | Phe | Ile | Phe | Pro | Pro | Ser | Asp | Glu | Gln | Leu | Lys | Ser | Gly |
| | | | 115 | | | | | 120 | | | | | 125 | | |
| Thr | Ala | Ser | Val | Val | Cys | Leu | Leu | Asn | Asn | Phe | Tyr | Pro | Arg | Glu | Ala |
| | 130 | | | | | 135 | | | | | 140 | | | | |
| Lys | Val | Gln | Trp | Lys | Val | Asp | Asn | Ala | Leu | Gln | Ser | Gly | Asn | Ser | Gln |
| 145 | | | | | 150 | | | | | 155 | | | | | 160 |
| Glu | Ser | Val | Thr | Glu | Gln | Asp | Ser | Lys | Asp | Ser | Thr | Tyr | Ser | Leu | Ser |
| | | | | 165 | | | | | 170 | | | | | 175 | |
| Ser | Thr | Leu | Thr | Leu | Ser | Lys | Ala | Asp | Pro | Gly | Val | Arg | Asp | Arg | Ala |
| | | | 180 | | | | | 185 | | | | | 190 | | |
| Gly | Leu | Gln | Gly | Leu | His | Leu | Pro | Ser | Ser | Thr | Leu | Thr | Leu | Ser | |
| | | | 195 | | | | | 200 | | | | | 205 | | |
| Lys | Ala | Asp | Tyr | Glu | Lys | His | Lys | Val | Tyr | Ala | Cys | Glu | Val | Thr | His |
| | 210 | | | | | 215 | | | | | 220 | | | | |
| Gln | Gly | Leu | Ser | Ser | Pro | Val | Thr | Lys | Ser | Phe | Asn | Arg | Gly | Glu | Cys |
| 225 | | | | | 230 | | | | | 235 | | | | | 240 |

```
<210> SEQ ID NO 13
<211> LENGTH: 645
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
```

```
gagatcgtgc tgacccagtc ccccgccacc ctgtccgtgt ccccggcga gaccgtgacc    60 ctgtcctgcc gggcctccca gaccatctac aagaacctgc actggtacca gcagaagtcc   120
ggcctgtccc cccggctgct gatcaagtac ggctccgact ccatctccgg catccccgcc   180
cggttctccg gctccggctc cggcaccgac tacaccctga ccatcaactc cgtggagccc   240
gaggacgagg gcatctacta ctgcctgcag ggctactcca ccccctggac cttcggccag   300
ggcaccaagc tggagatcaa gcggaccgtg gccgcccct ccgtgttcat cttccccccc   360
tccgacgagc agctgaagtc cggcaccgcc tccgtggtgt gcctgctgaa caacttctac   420
ccccgggagg ccaaggtgca gtggaaggtg gacaacgccc tgcagtccgg caactcccag   480
gagtccgtga ccgagcagga ctccaaggac tccacctact ccctgtcctc caccctgacc   540
ctgtccaagg ccgactacga aagcacaag gtgtacgcct gcgaggtgac ccaccagggc   600
ctgtcctccc ccgtgaccaa gtccttcaac cggggcgagt gctag             645
```

<210> SEQ ID NO 14
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

```
Glu Ile Val Leu Thr Gln Ser Pro Ala Thr Leu Ser Val Ser Pro Gly
1               5                   10                  15

Glu Thr Val Thr Leu Ser Cys Arg Ala Ser Gln Thr Ile Tyr Lys Asn
            20                  25                  30

Leu His Trp Tyr Gln Gln Lys Ser Gly Leu Ser Pro Arg Leu Leu Ile
        35                  40                  45

Lys Tyr Gly Ser Asp Ser Ile Ser Gly Ile Pro Ala Arg Phe Ser Gly
    50                  55                  60

Ser Gly Ser Gly Thr Asp Tyr Thr Leu Thr Ile Asn Ser Val Glu Pro
65                  70                  75                  80

Glu Asp Glu Gly Ile Tyr Tyr Cys Leu Gln Gly Tyr Ser Thr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 15
<211> LENGTH: 1320
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 15

```
cagatccagc tggtgcagtc cggcccgag gtgaagaagc cggcgcctc cgtgaagatc      60
tcctgcaagg cctccggcta caccttcacc gactactcca tgcactgggt gaagaaggcc    120
cccggccagg gcctggagtg gctgggctgg atcaacaccg ccaccggcga gcccacctac    180
gccgacgact tcaagggccg gttcaccatc accctggaca cctccgcccg gaccgtgtac    240
ctgcagatca acaacctgcg gtccgaggac accgccacct acttctgctt ctcctactac    300
gactactggg gccagggcac cctgctgacc gtgtcctccg cctccaccaa gggcccctcc    360
gtgttccccc tggcccctg ctccggtcc acctccgagt ccaccgccgc cctgggctgc      420
ctggtgaagg actacttccc cgagcccgtg accgtgtcct ggaactccgg cgccctgacc    480
tccggcgtgc acaccttccc cgccgtgctg cagtcctccg gcctgtactc cctgtcctcc    540
gtggtgaccg tgccctcctc ctccctgggc accaagacct acacctgcaa cgtggaccac    600
aagcccctcca acaccaaggt ggacaagcgg gtggagtcca agtacggccc ccctgcccc    660
tcctgccccg cccccgagtt cctgggcggc ccctccgtgt tcctgttccc ccccaagccc    720
aaggacaccc tgatgatctc ccggaccccc gaggtgacct gcgtggtggt ggacgtgtcc    780
caggaggacc ccgaggtgca gttcaactgg tacgtggacg gcgtggaggt gcacaacgcc    840
aagaccaagc ccggagga gcagttcaac tccacctacc gggtggtgtc cgtgctgacc      900
gtgctgcacc aggactggct gaacggcaag gagtacaagt gcaaggtgtc caacaagggc    960
ctgcccctcct ccatcgagaa gaccatctcc aaggccaagg gccagccccg ggagccccag  1020
gtgtacaccc tgccccctc ccaggaggag atgaccaaga accaggtgtc cctgacctgc    1080
ctggtgaagg gcttctaccc ctccgacatc gccgtggagt gggagtccaa cggccagccc   1140
gagaacaact acaagaccac ccccccgtg ctggactccg acggctcctt cttcctgtac    1200
tcccggctga ccgtggacaa gtccggtgg caggagggca acgtgttctc ctgctccgtg     1260
atgcacgagg ccctgcacaa ccactacacc cagaagtccc tgtccctgtc cctgggcaag   1320
```

<210> SEQ ID NO 16
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Gln Ile Gln Leu Val Gln Ser Gly Pro Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Ser Met His Trp Val Lys Ala Pro Gly Gln Gly Leu Glu Trp Leu
        35                  40                  45

Gly Trp Ile Asn Thr Ala Thr Gly Glu Pro Thr Tyr Ala Asp Asp Phe
    50                  55                  60

Lys Gly Arg Phe Thr Ile Thr Leu Asp Thr Ser Ala Arg Thr Val Tyr
65                  70                  75                  80

Leu Gln Ile Asn Asn Leu Arg Ser Glu Asp Thr Ala Thr Tyr Phe Cys
                85                  90                  95
```

Phe Ser Tyr Tyr Asp Tyr Trp Gly Gln Gly Thr Leu Leu Thr Val Ser
            100                 105                 110

Ser Ala Ser Thr Lys Gly Pro Ser Val Phe Pro Leu Ala Pro Cys Ser
            115                 120                 125

Arg Ser Thr Ser Glu Ser Thr Ala Ala Leu Gly Cys Leu Val Lys Asp
        130                 135                 140

Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
            180                 185                 190

Thr Tyr Thr Cys Asn Val Asp His Lys Pro Ser Asn Thr Lys Val Asp
        195                 200                 205

Lys Arg Val Glu Ser Lys Tyr Gly Pro Pro Cys Pro Ser Cys Pro Ala
210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
            260                 265                 270

Asp Gly Val Glu Val His Asn Ala Lys Thr Lys Pro Arg Glu Glu Gln
        275                 280                 285

Phe Asn Ser Thr Tyr Arg Val Val Ser Val Leu Thr Val Leu His Gln
    290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
    370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
            420                 425                 430

Ser Leu Ser Leu Ser Leu Gly Lys
        435                 440

<210> SEQ ID NO 17
<211> LENGTH: 1320
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
caggtgcagc tggtgcagtc cggccccgag gtgaagaagc ccggcgcctc cgtgaagatc      60

```
tcctgcaagg cctccggcta caccttcacc gactactcca tgcactgggt gaagaaggcc    120
cccggccagg gcctgaagtg gctgggctgg atcaacaccg ccaccggcga gcccacctac    180
gccgacgact tcaagggccg gttcaccatc accctggaca cctccgcccg gaccgtgtac    240
ctggagatct cctccctgcg gtccgaggac accgccacct acttctgctt ctcctactac    300
gactactggg gccagggcac cctgctgacc gtgtcctccg cctccaccaa gggcccctcc    360
gtgttccccc tggcccctg ctccggtcc acctccgagt ccaccgccgc cctgggctgc      420
ctggtgaagg actacttccc cgagcccgtg accgtgtcct ggaactccgg cgccctgacc    480
tccggcgtgc acaccttccc cgccgtgctg cagtcctccg gcctgtactc cctgtcctcc    540
gtggtgaccg tgccctcctc ctccctgggc accaagacct acacctgcaa cgtggaccac    600
aagccctcca acaccaaggt ggacaagcgg gtggagtcca agtacggccc ccctgcccc    660
tcctgccccg ccccgagtt cctgggcggc ccctccgtgt tcctgttccc ccccaagccc    720
aaggacaccc tgatgatctc ccggaccccc gaggtgacct gcgtggtggt ggacgtgtcc    780
caggaggacc ccgaggtgca gttcaactgg tacgtggacg gcgtggaggt gcacaacgcc    840
aagaccaagc cccgggagga gcagttcaac tccacctacc gggtggtgtc cgtgctgacc    900
gtgctgcacc aggactggct gaacggcaag gagtacaagt gcaaggtgtc caacaagggc    960
ctgcctcct ccatcgagaa gaccatctcc aaggccaagg gccagccccg ggagccccag    1020
gtgtacaccc tgcccccctc ccaggaggag atgaccaaga accaggtgtc cctgacctgc    1080
ctggtgaagg gcttctaccc ctccgacatc gccgtggagt gggagtccaa cggccagccc    1140
gagaacaact acaagaccac cccccccgtg ctggactccg acggctcctt cttcctgtac    1200
tcccggctga ccgtggacaa gtcccggtgg caggagggca acgtgttctc ctgctccgtg    1260
atgcacgagg ccctgcacaa ccactacacc cagaagtccc tgtccctgtc cctgggcaag    1320
```

<210> SEQ ID NO 18
<211> LENGTH: 440
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Val Gln Ser Gly Pro Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Ser Met His Trp Val Lys Ala Pro Gly Gln Gly Leu Lys Trp Leu
        35                  40                  45

Gly Trp Ile Asn Thr Ala Thr Gly Glu Pro Thr Tyr Ala Asp Asp Phe
    50                  55                  60

Lys Gly Arg Phe Thr Ile Thr Leu Asp Thr Ser Ala Arg Thr Val Tyr
65                  70                  75                  80

Leu Glu Ile Ser Ser Leu Arg Ser Glu Asp Thr Ala Thr Tyr Phe Cys
                85                  90                  95

Phe Ser Tyr Tyr Asp Tyr Trp Gly Gln Gly Thr Leu Leu Thr Val Ser
            100                 105                 110

Ser Ala Ser Thr Lys Gly Pro Ser Val Phe Pro Leu Ala Pro Cys Ser
        115                 120                 125

Arg Ser Thr Ser Glu Ser Thr Ala Ala Leu Gly Cys Leu Val Lys Asp

```
                130              135                 140
Tyr Phe Pro Glu Pro Val Thr Val Ser Trp Asn Ser Gly Ala Leu Thr
145                 150                 155                 160

Ser Gly Val His Thr Phe Pro Ala Val Leu Gln Ser Ser Gly Leu Tyr
                165                 170                 175

Ser Leu Ser Ser Val Val Thr Val Pro Ser Ser Ser Leu Gly Thr Lys
                180                 185                 190

Thr Tyr Thr Cys Asn Val Asp His Lys Pro Ser Asn Thr Lys Val Asp
                195                 200                 205

Lys Arg Val Glu Ser Lys Tyr Gly Pro Pro Cys Pro Ser Cys Pro Ala
            210                 215                 220

Pro Glu Phe Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser Gln Glu Asp Pro Glu Val Gln Phe Asn Trp Tyr Val
                260                 265                 270

Asp Gly Val Glu Val His Asn Ala Lys Thr Lys Pro Arg Glu Glu Gln
            275                 280                 285

Phe Asn Ser Thr Tyr Arg Val Val Ser Val Leu Thr Val Leu His Gln
290                 295                 300

Asp Trp Leu Asn Gly Lys Glu Tyr Lys Cys Lys Val Ser Asn Lys Gly
305                 310                 315                 320

Leu Pro Ser Ser Ile Glu Lys Thr Ile Ser Lys Ala Lys Gly Gln Pro
                325                 330                 335

Arg Glu Pro Gln Val Tyr Thr Leu Pro Pro Ser Gln Glu Glu Met Thr
            340                 345                 350

Lys Asn Gln Val Ser Leu Thr Cys Leu Val Lys Gly Phe Tyr Pro Ser
                355                 360                 365

Asp Ile Ala Val Glu Trp Glu Ser Asn Gly Gln Pro Glu Asn Asn Tyr
370                 375                 380

Lys Thr Thr Pro Pro Val Leu Asp Ser Asp Gly Ser Phe Phe Leu Tyr
385                 390                 395                 400

Ser Arg Leu Thr Val Asp Lys Ser Arg Trp Gln Glu Gly Asn Val Phe
                405                 410                 415

Ser Cys Ser Val Met His Glu Ala Leu His Asn His Tyr Thr Gln Lys
                420                 425                 430

Ser Leu Ser Leu Ser Leu Gly Lys
                435                 440

<210> SEQ ID NO 19
<211> LENGTH: 2129
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
caggtgcagc tggtgcagtc cggccccgag gtgaagaagc ccggcgcctc cgtgaagatc      60
tcctgcaagg cctccggcta caccttcacc gactactcca tgcactgggt gaagaaggcc     120
cccggccagg gcctgaagtg gctgggctgg atcaacaccg ccaccggcga gcccacctac     180
gccgacgact tcaagggccg gttcaccatc accctggaca cctccgcccg gaccgtgtac     240
ctggagatct cctccctgcg gtccgaggac accgccacct acttctgctt ctcctactac     300
```

-continued

```
gactactggg gccagggcac cctgctgacc gtgtcctccg cctccaccaa gggcccatcg    360
gtcttccccc tggcaccctc ctccaagagc acctctgggg cacagcggc cctgggctgc    420 ctggtcaagg actacttccc cgaaccggtg acggtgtcgt ggaactcagg cgccctgacc    480
agcggcgtgc acaccttccc ggccgtccta cagtcctcag gactctactc cctcagcagc    540
gtggtgaccg tgccctccag cagcttgggc acccagacct acatctgcaa cgtgaatcac    600
aagcccagca caccaaggt ggacaagaga gttgagccca atcttgtga caaaactcac      660 acatgcccac cgtgcccagc acctgaactc ctggggggac cgtcagtctt cctcttcccc    720
ccaaaaccca aggacaccct catgatctcc cggacccctg aggtcacatg cgtggtggtg    780
gacgtgagcc acgaagaccc tgaggtcaag ttcaactggt acgtggacgg cgtggaggtg    840
cataatgcca agacaaagcc gcgggaggag cagtacgcca gcacgtaccg tgtggtcagc    900
gtcctcaccg tcctgcacca ggactggctg aatggcaagg agtacaagtg caaggtctcc    960
aacaaagccc tcccagcccc catcgagaaa accatctcca aagccaaagg cagccccga   1020 gaaccacagg tgtacaccct gcccccatcc cgggatgagc tgaccaagaa ccaggtcagc   1080
ctgacctgcc tggtcaaagg cttctatccc agcgacatcg ccgtggagtg ggagagcaat   1140
gggcagccgg agaacaacta caagaccacg cctcccgtgc tggactccga cggctccttc   1200
ttcctctaca gcaagctcac cgtggacaag agcaggtggc agcaggggaa cgtcttctca   1260
tgctccgtga tgcatgaggc tctgcacaac cactacacgc agaagagcct ctccctgtct   1320
ccgggtaaag gatccggagg aggaggtagc ggaggaggag gttctggcgg agggggttcc   1380
caggtgcagc tggtgcagag cggaggagga gtggtgcagc aggaaggag cctgcgactg   1440 tcttgcaagg ctagtggcta caccttcaca cgatatacta tgcactgggt gaggcaggca   1500
cctggtaaag gcctggagtg gatcggctac attaacccct cgggggata caccaactat   1560 aatcagaagt tcaaagacag gttcaccatc tcacgcgata actccaagaa taccgccttc   1620
ctgcagatgg actccctgcg gcccgaagat acaggcgtgt attttgcgc tagatactat   1680 gacgatcatt actgtctgga ctattgggga caggggaccc ctgtgacagt gtccagcggt   1740
ggaggagggt caggtggagg agggagcggt ggcggagggt ctgacatcca gatgacccag   1800
tccccatcta gtctgagcgc ctctgtgggc gatagagtga ctattacctg cagtgcttca   1860
tccagcgtga gctacatgaa ctggtatcag cagacacccg gaaaggcacc taaacgctgg   1920
atctacgata ctagcaagct ggcctctggc gtgcccagtc gattcagtgg ttcaggctcc   1980
ggaaccgact ataccttcac catctctagt ctgcagcctg aggatattgc cacatactat   2040
tgtcagcagt ggtcatccaa tccattcact tttgggcagg gtaccaaact gcagattaca   2100
aggtagggat ccgagctcgg tacaaaccg                                     2129
```

<210> SEQ ID NO 20
<211> LENGTH: 701
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

```
Gln Val Gln Leu Val Gln Ser Gly Pro Glu Val Lys Lys Pro Gly Ala
1               5                   10                  15

Ser Val Lys Ile Ser Cys Lys Ala Ser Gly Tyr Thr Phe Thr Asp Tyr
            20                  25                  30
```

```
Ser Met His Trp Val Lys Lys Ala Pro Gly Gln Gly Leu Lys Trp Leu
            35                  40                  45
Gly Trp Ile Asn Thr Ala Thr Gly Glu Pro Thr Tyr Ala Asp Asp Phe
        50                  55                  60
Lys Gly Arg Phe Thr Ile Thr Leu Asp Thr Ser Ala Arg Thr Val Tyr
 65                  70                  75                  80
Leu Glu Ile Ser Ser Leu Arg Ser Glu Asp Thr Ala Thr Tyr Phe Cys
                85                  90                  95
Phe Ser Tyr Tyr Asp Tyr Trp Gly Gln Gly Thr Leu Leu Thr Val Ser
            100                 105                 110
Ser Ala Ser Thr Lys Gly Pro Ser Val Phe Pro Leu Ala Pro Ser Ser
            115                 120                 125
Lys Ser Thr Ser Gly Gly Thr Ala Ala Leu Gly Cys Leu Val Lys Asp
            130                 135                 140
Tyr Phe Pro Glu Pro Val Thr Val Ser Trp Asn Ser Gly Ala Leu Thr
145                 150                 155                 160
Ser Gly Val His Thr Phe Pro Ala Val Leu Gln Ser Ser Gly Leu Tyr
                165                 170                 175
Ser Leu Ser Ser Val Val Thr Val Pro Ser Ser Ser Leu Gly Thr Gln
            180                 185                 190
Thr Tyr Ile Cys Asn Val Asn His Lys Pro Ser Asn Thr Lys Val Asp
            195                 200                 205
Lys Arg Val Glu Pro Lys Ser Cys Asp Lys Thr His Thr Cys Pro Pro
            210                 215                 220
Cys Pro Ala Pro Glu Leu Leu Gly Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser His Glu Asp Pro Glu Val Lys Phe Asn
            260                 265                 270
Trp Tyr Val Asp Gly Val Glu Val His Asn Ala Lys Thr Lys Pro Arg
            275                 280                 285
Glu Glu Gln Tyr Ala Ser Thr Tyr Arg Val Val Ser Val Leu Thr Val
            290                 295                 300
Leu His Gln Asp Trp Leu Asn Gly Lys Glu Tyr Lys Cys Lys Val Ser
305                 310                 315                 320
Asn Lys Ala Leu Pro Ala Pro Ile Glu Lys Thr Ile Ser Lys Ala Lys
                325                 330                 335
Gly Gln Pro Arg Glu Pro Gln Val Tyr Thr Leu Pro Pro Ser Arg Asp
            340                 345                 350
Glu Leu Thr Lys Asn Gln Val Ser Leu Thr Cys Leu Val Lys Gly Phe
            355                 360                 365
Tyr Pro Ser Asp Ile Ala Val Glu Trp Glu Ser Asn Gly Gln Pro Glu
            370                 375                 380
Asn Asn Tyr Lys Thr Thr Pro Pro Val Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly Lys Gly Ser Gly Gly Gly
            435                 440                 445
```

Gly Ser Gly Gly Gly Gly Ser Gly Gly Gly Ser Gln Val Gln Leu
    450                 455                 460

Val Gln Ser Gly Gly Val Val Gln Pro Gly Arg Ser Leu Arg Leu
465                 470                 475                 480

Ser Cys Lys Ala Ser Gly Tyr Thr Phe Thr Arg Tyr Thr Met His Trp
                485                 490                 495

Val Arg Gln Ala Pro Gly Lys Gly Leu Glu Trp Ile Gly Tyr Ile Asn
                500                 505                 510

Pro Ser Arg Gly Tyr Thr Asn Tyr Asn Gln Lys Phe Lys Asp Arg Phe
            515                 520                 525

Thr Ile Ser Arg Asp Asn Ser Lys Asn Thr Ala Phe Leu Gln Met Asp
530                 535                 540

Ser Leu Arg Pro Glu Asp Thr Gly Val Tyr Phe Cys Ala Arg Tyr Tyr
545                 550                 555                 560

Asp Asp His Tyr Cys Leu Asp Tyr Trp Gly Gln Gly Thr Pro Val Thr
                565                 570                 575

Val Ser Ser Gly Gly Gly Gly Ser Gly Gly Gly Ser Gly Gly Gly
                580                 585                 590

Gly Ser Asp Ile Gln Met Thr Gln Ser Pro Ser Ser Leu Ser Ala Ser
            595                 600                 605

Val Gly Asp Arg Val Thr Ile Thr Cys Ser Ala Ser Ser Ser Val Ser
610                 615                 620

Tyr Met Asn Trp Tyr Gln Gln Thr Pro Gly Lys Ala Pro Lys Arg Trp
625                 630                 635                 640

Ile Tyr Asp Thr Ser Lys Leu Ala Ser Gly Val Pro Ser Arg Phe Ser
                645                 650                 655

Gly Ser Gly Ser Gly Thr Asp Tyr Thr Phe Thr Ile Ser Ser Leu Gln
            660                 665                 670

Pro Glu Asp Ile Ala Thr Tyr Tyr Cys Gln Gln Trp Ser Ser Asn Pro
        675                 680                 685

Phe Thr Phe Gly Gln Gly Thr Lys Leu Gln Ile Thr Arg
690                 695                 700

<210> SEQ ID NO 21
<211> LENGTH: 1465
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
gagatcgtgc tgacccagtc ccccgccacc ctgtccgtgt ccccggcga gaccgtgacc      60
ctgtcctgcc gggcctccca gaccatctac aagaacctgc actggtacca gcagaagtcc    120
ggcctgtccc ccggctgct gatcaagtac ggctccgact ccatctccgg catccccgcc    180
cggttctccg gctccggctc cggcaccgac tacacccctg accatcaactc cgtggagccc    240
gaggacgagg gcatctacta ctgcctgcag ggctactcca ccccctggac cttcggccag    300
ggcaccaagc tggagatcaa gcggaccgtg gccgccccct ccgtgttcat cttcccccc     360
tccgacgagc agctgaagtc cggcaccgcc tccgtggtgt gcctgctgaa caacttctac    420
ccccgggagg ccaaggtgca gtggaaggtg gacaacgccc tgcagtccgg caactcccag    480
gagtccgtga ccgagcagga ctccaaggac tccacctact ccctgtcctc caccctgacc    540
ctgtccaagg ccgactacga gaagcacaag gtgtacgcct gcgaggtgac ccaccagggc    600

```
ctgtcctccc ccgtgaccaa gtccttcaac cggggcgagt gcactagtgg aggaggaggt    660
agcggaggag gaggttctgg cggagggggt tcccaggtgc agctggtgca gagcggagga    720
ggagtggtgc agccaggaag gagcctgcga ctgtcttgca aggctagtgg ctacaccttc    780
acacgatata ctatgcactg ggtgaggcag gcacctggta aaggcctgga gtggatcggc    840
tacattaacc cctctagggg atacaccaac tataatcaga gttcaaaga caggttcacc     900
atctcacgcg ataactccaa gaataccgcc ttcctgcaga tggactccct gcggcccgaa    960
gatacaggcg tgtattttg cgctagatac tatgacgatc attactgtct ggactattgg   1020
ggacagggga cccctgtgac agtgtccagc ggtggaggag ggtcaggtgg aggagggagc   1080
ggtggcggag ggtctgacat ccagatgacc cagtccccat ctagtctgag cgcctctgtg   1140
ggcgatagag tgactattac ctgcagtgct tcatccagcg tgagctacat gaactggtat   1200
cagcagacac ccggaaaggc acctaaacgc tggatctacg atactagcaa gctggcctct   1260
ggcgtgccca gtcgattcag tggttcaggc tccggaaccg actataccct caccatctct   1320
agtctgcagc ctgaggatat tgccacatac tattgtcagc agtggtcatc caatccattc   1380
acttttgggc agggtaccaa actgcagatt acaaggtagt ctagagcttg cctcgagcag   1440
cgctgctcga gagatctacg ggtgg                                          1465
```

<210> SEQ ID NO 22
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Glu Ile Val Leu Thr Gln Ser Pro Ala Thr Leu Ser Val Ser Pro Gly
1               5                   10                  15

Glu Thr Val Thr Leu Ser Cys Arg Ala Ser Gln Thr Ile Tyr Lys Asn
            20                  25                  30

Leu His Trp Tyr Gln Gln Lys Ser Gly Leu Ser Pro Arg Leu Leu Ile
        35                  40                  45

Lys Tyr Gly Ser Asp Ser Ile Ser Gly Ile Pro Ala Arg Phe Ser Gly
    50                  55                  60

Ser Gly Ser Gly Thr Asp Tyr Thr Leu Thr Ile Asn Ser Val Glu Pro
65                  70                  75                  80

Glu Asp Glu Gly Ile Tyr Tyr Cys Leu Gln Gly Tyr Ser Thr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys Thr Ser Gly Gly Gly Ser Gly Gly Gly
    210             215                 220

Gly Ser Gly Gly Gly Gly Ser Gln Val Gln Leu Val Gln Ser Gly Gly
225                 230                 235                 240

Gly Val Val Gln Pro Gly Arg Ser Leu Arg Leu Ser Cys Lys Ala Ser
                245                 250                 255

Gly Tyr Thr Phe Thr Arg Tyr Thr Met His Trp Val Arg Gln Ala Pro
                260                 265                 270

Gly Lys Gly Leu Glu Trp Ile Gly Tyr Ile Asn Pro Ser Arg Gly Tyr
        275                 280                 285

Thr Asn Tyr Asn Gln Lys Phe Lys Asp Arg Phe Thr Ile Ser Arg Asp
    290                 295                 300

Asn Ser Lys Asn Thr Ala Phe Leu Gln Met Asp Ser Leu Arg Pro Glu
305                 310                 315                 320

Asp Thr Gly Val Tyr Phe Cys Ala Arg Tyr Tyr Asp Asp His Tyr Cys
                325                 330                 335

Leu Asp Tyr Trp Gly Gln Gly Thr Pro Val Thr Val Ser Ser Gly Gly
                340                 345                 350

Gly Gly Ser Gly Gly Gly Gly Ser Gly Gly Gly Gly Ser Asp Ile Gln
        355                 360                 365

Met Thr Gln Ser Pro Ser Ser Leu Ser Ala Ser Val Gly Asp Arg Val
    370                 375                 380

Thr Ile Thr Cys Ser Ala Ser Ser Ser Val Ser Tyr Met Asn Trp Tyr
385                 390                 395                 400

Gln Gln Thr Pro Gly Lys Ala Pro Lys Arg Trp Ile Tyr Asp Thr Ser
                405                 410                 415

Lys Leu Ala Ser Gly Val Pro Ser Arg Phe Ser Gly Ser Gly Ser Gly
            420                 425                 430

Thr Asp Tyr Thr Phe Thr Ile Ser Ser Leu Gln Pro Glu Asp Ile Ala
        435                 440                 445

Thr Tyr Tyr Cys Gln Gln Trp Ser Ser Asn Pro Phe Thr Phe Gly Gln
    450                 455                 460

Gly Thr Lys Leu Gln Ile Thr Arg
465                 470

<210> SEQ ID NO 23
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Gly Gly Gly Ser Gly Gly Gly Gly Ser Gly Gly Gly Gly Ser
1               5                   10                  15
```